US007893246B2

(12) United States Patent
Saito et al.

(10) Patent No.: US 7,893,246 B2
(45) Date of Patent: Feb. 22, 2011

(54) SIRNA CAPABLE OF INHIBITING THE EXPRESSION OF AN ONCOGENE INVOLVED IN CERVICAL CANCER

(75) Inventors: Akira Saito, Minato-ku (JP); Masahiko Kuroda, Suginami-ku (JP)

(73) Assignees: NEC Corporation, Tokyo (JP); Masahiko Kuroda, Tokyo (JP)

( * ) Notice: Subject to any disclaimer, the term of this patent is extended or adjusted under 35 U.S.C. 154(b) by 35 days.

(21) Appl. No.: 12/207,298

(22) Filed: Sep. 9, 2008

(65) Prior Publication Data

US 2009/0042830 A1 Feb. 12, 2009

Related U.S. Application Data

(62) Division of application No. 11/449,671, filed on Jun. 9, 2006, now Pat. No. 7,432,358, which is a division of application No. 10/758,562, filed on Jan. 16, 2004, now Pat. No. 7,358,350.

(30) Foreign Application Priority Data

Jan. 20, 2003 (JP) ............................. 2003-011478

(51) Int. Cl.
C07H 21/04 (2006.01)
C12N 15/11 (2006.01)
(52) U.S. Cl. .................................. 536/24.5; 514/44 A
(58) Field of Classification Search ................ 536/24.5; 514/44 A
See application file for complete search history.

(56) References Cited

U.S. PATENT DOCUMENTS

| 6,506,559 | B1 * | 1/2003 | Fire et al. ........................ 435/6 |
| 2004/0072154 | A1 * | 4/2004 | Morris et al. ................... 435/6 |
| 2005/0255487 | A1 * | 11/2005 | Khvorova et al. .............. 435/6 |

FOREIGN PATENT DOCUMENTS

| JP | 3091870 B2 | 7/2000 |
| JP | 2001-27888 A | 3/2001 |
| JP | 2002-524525 A | 8/2002 |
| WO | 00/42180 A1 | 7/2000 |
| WO | 00/55351 A1 | 9/2000 |
| WO | 03/008583 A2 | 1/2003 |

OTHER PUBLICATIONS

D. Melton et al., "ih21a06.x1 Human Insulinoma Home Sapiens cDNA Clone Image: 3' Similar to TR: Q92549 Q92549 Myeloblast KIAA0261, mRNA Sequence", Endocrine Pancreas Consortium, Harvard University, Howard Hughes Medical Institute, Department of Molecular and Cellular Biology, Feb. 22, 2002, Cambridge (Database XP-002297479).
"601058669F1 NIH_MGC_10 Homo Sapiens cDNA Clone Image: 3445337 5', mRNA Sequence", National Institutes of Health, Mammalian Gene Collection (MGC), Aug. 11, 2000 (Database XP-002297480).
Takahiro Nagase et al., "Prediction of the Coding Sequences of Unidentified Human Genes. VI. The Coding Sequences of 80 New Genes (KIAA0201-KIA0280) Deduced by Analysis of cDNA Clones from Cell Line KG-1 and Brain", DNA Research, Oct. 31, 1996, pp. 321-329, vol. 3, No. 5, Kazusa Dna Research Institute, Chiba, Japan (Database XP-002059454).
B.A. Kwiatkowski et al., "Homo Sapiens FOE mRNA, Complete Cds", Medical Oncology, University of Washington and VA Puget Sound Health Care System, Jan. 2, 2003 (Database XP-002297481).
Kenneth W. Dobie et al., "Identification of Chromosome Inheritance Modifiers in Drosophila Melanogaster", Genetics, Apr. 2001, pp. 1623-1637, vol. 157, No. 4, Genetics Society of America (Database XP-002297476).
Fiammetta Verni et al., "Genetic and Molecular Analysis of Wings Apart-Like (WAPL), a Gene Controlling Heterochromatin Organization in Drosophila Melanogaster", Genetics, Apr. 2000, pp. 1693-1710, vol. 154, No. 4, Genetics Society of America (Database XP-002297477).
T. Ohbayashi et al., "Homo Sapiens hWAPL mRNA for Mammalian Homolog of Wings Apart-Like Protein, Complete Cds", Jul. 2, 2003, Tokyo Medical University, Department of Pathology, Tokyo, Japan (Database XP-002297482).
K. Oikawa et al., "Mammalian Homolog of Wings Apart-Like Protein", Oct. 1, 2003 (Database XP-002297545).
Kosuke Oikawa et al., "Expression of a Novel Human Gene, Human Wings Apart-Like (hWAPL), Is Associated with Cervical Carcinogenesis and Tumor Progression", Cancer Research, May 15, 2004, pp. 3545-3549, vol. 64, No. 10 (Database XP-002297478).
Database EMBL [Online] Oct. 10, 2001, "Human mRNA for KIAA0261, partial cds." Database accession No. D87450.
Fu et al (EMBO Journal, 1996, vol. 15, pp. 4392-4401).
Brennan et al (Journal of Autoimmunity, 1989, vol. 2 suppl., pp. 177-186).
Zimmer (Cell Motility and the Cytoskeleton, 1991, vol. 20, pp. 325-337).
Eriksson et al. (Diabetologia, 1992, vol. 35, pp. 143-147).
Freshney (Culture of Animal Cells, A Manual of Basic Technique, Alan R. Liss, Inc., 1983, New York, p. 4).
Dermer (Bio/Technology, 1994, 12:320).

(Continued)

*Primary Examiner*—J. E Angell
(74) *Attorney, Agent, or Firm*—Sughrue Mion, PLLC

(57) ABSTRACT

The present invention identifies the total nucleotide sequence of a novel oncogene from human, which is directly involved in such a cancerization mechanism as for cervical cancer induced by HPV infection of cervical epithelial cell and the amino acid sequence of an oncogenic protein encoded thereby, and to provide a full-length polynucleotide encoding a peptide chain of the oncogenic protein derived from the novel oncogene, which can be used for recombinant production of the oncogenic protein, and the peptide chain of the oncogenic protein produced recombinantly therewith. Specifically, the present invention provides a novel oncogene polynucleotide from human involving development of cervical cancer, comprising a nucleotide sequence encoding an amino acid sequence of SEQ. ID. No. 1, particularly a polynucleotide of the nucleotide sequence of SEQ. ID. No. 2.

2 Claims, 10 Drawing Sheets

OTHER PUBLICATIONS

EMBL Bioinformatics Harvester entry Q92549 (as downloaded on Oct. 31, 2006).

Nagase et al. (1996, DNA Research 3:321-329).

T. Nagase et al., DNA Research vol. 3, No. 5 pp. 321-329 with supplement of pp. 341-358 (1996); published on Oct. 31, 1996.

T. Tuschl and A. Borkhardt, Molecular Interventions, vol. 2 (3) pp. 158-67 (Jun. 2002).

Human myeloblast mRNA for KIAA0261 gene, partial cds. [online]. Nov. 8, 1996. NCBI Entres Nucleotide, ACCESSION D87450 [Retrieved on May 13, 2005]. Retrieved from the internet:<URL: http://www.ncbi.nih.gov./entres/viewer.fcgi?1665788:OLDID:2861690>.

Homo sapiens FOE mRNA, complete cds. [online]. Jan. 1, 2003. NCBI Entres Nucleotide, ACCESSION AF479418 [Retrieved on May 13, 2005]. Retrieved from the internet:<URL: http://www.ncbi.nih.gov./entres/viewer.fcgi?27450619:NCBI:4287007>.

F. Verni et al., Genetics vol. 154, No. 4, pp. 1693-1710.

* cited by examiner

Fig.2

```
hWAPL:  623  LKCRREDKELYTVVQHVKHFNDVVEFGENQEFTDDIEYLLSGLKSTQPLNTRCLSVISLA  682
              ++  R+ K+ Y VV++VK  + + E GE QE  DD+EY+L  L+   P  TRCLS + LA
dWAPL: 1137  IRVDRKTKDYYPVVRNVKTAHQIQEIGEYQEMDDDVEYILDALQPHNPPATRCLSALQLA 1196 hWAPL:  683  TKCAMPSFRMHLRAHGMVAMVFKTLDDSQHHQNLSLCTAALMYILSRDRLNMDLDRASLD  742
              KC MP+FRMH+RAHG+V    FK L D+     +L LCT+A+MYILS++ LNMDLDR SL+
dWAPL: 1197  AKCMMPAFRMHVRAHGVVTKFFKALSDANKDLSLGLCTSAIMYILSQEGLNMDLDRDSLE 1256 hWAPL:  743  LMIRLLELEQDASSAKL--LNEKDMNKIKEKIRRLCETV----HNKHLDLENITTGHLAM  796
              LMI LLE +    S +   +      ++ K+K+R LCE +        HL+++++T G LAM
dWAPL: 1257  LMINLLEADGVGGSTETGHSDRAGYDRNKQKVRELCEEIKAQGKGTHLNVDSLTVGTLAM 1316 hWAPL:  797  ETLLSLTSKRAGDWFKEELRLLGGLDHIVDKVKE-CVDHLSRDED---EEKLVASLWGAE  852
              ETLLSLTSKRAG+WFKE+LR LGGL+HI+ + + C   ++ D +    + L+ ++
dWAPL: 1317  ETLLSLTSKRAGEWFKEDLRKLGGLEHIIKTISDFCRPVIACDTEIDWQPTLLDNMQTVA 1376 hWAPL:  853  RCLRVLESVTVHNPENQSYLIAYKDSQLIVSSAKALQHCEELIQQYNRAEDSICLADSKP  912
              RCLRVLE+VT HN NQ Y++  + +           E L Q Y      I L   S
dWAPL: 1377  RCLRVLENVTQHNETNQRYMLTSGQGKAV---------ETLCQLYRLCSRQIMLHPSD- 1425 hWAPL:  913  LPHQNVTNHVGKAVEDCMRAIIGVLLNLTND-NE----WGSTKTGEQDGLIGTALNCVLQ  967
                +   H G A+ + +   ++ VL+NLT+  NE       G+   G++    ++ T+   +L
dWAPL: 1426  -GGGSNKEHPGVAMRELLVPVLKVLINLTHTFNEAQPSLGAELLGQRGDVVETSFRLLLL 1484 hWAPL:  968  VPKYLPQEQRFDIRVLGLGLLINLVEYSARNRHCLVNMETSCSFDSSICSGEGDDSLRIG 1027
                Y+P +  F++ +L L LLINL   ++ NR L+    + +     D+
dWAPL: 1485  SANYIPDQCVFELSILVLTLLINLCMHTVPNRAALMQAAAPAEYVA--------DNPPAQ 1536 hWAPL: 1028  GQVHAVQALVQLFLERERAAQLAESKTDELIKDAPTTQHDKSGEWQETSGEIQWVSTEKT 1087
              G V A+QAL++  F + E  A+L E  TD  ++         ++K   + QE    E
dWAPL: 1537  GSVSALQALLEYFYKCEELARLVEKNTDAFLE-----SNEKGKKKQEEVEE--------- 1582 hWAPL: 1088  DGTEEKHKKEEEDEELDLNKALQHAGKHMEDCIVASYTALLLGCLCQESPINVTTVREYL 1147
                            +N +Q AG HME  +  SY A+L+G L  ++ +  +  VR  L
dWAPL: 1583  ---------------TVNNLVQRAGHHMEHTLKGSYAAILVGNLIADNELYESVVRRQL 1626 hWAPL: 1148  PEGDFSIMTEMLKKFLSFMNLTC---AVGTTGQKSISRVIE 1185
                  F  + +L+K+ +FMNLT    A     KS R+I+
dWAPL: 1627  RGNSFKEIIGVLEKYHTFMNLTSSLEAAFVAHMKSTKRIID 1667
```

>pir:T13610 [T13610] parallel sister chromatids protein - fruit fly
  Length = 1741
  Identities = 204/581 (35%), Positives = 309/581 (53%), Gaps = 68/581 (11%)

Fig. 3

```
   1 MTSRFGKTYSRKGGHGSSKFDEVFSNKRTTLSTKWGETTFMAKLGQKRPNFKPDIQEIPK
   1 MTSRFGKTYSRKGGNGSSKFDEVFSNKRTTLSTKWGETTFMAKLGQKRPNFKPDIQEIPK

61 KPKVEESTGDPFGFDSDDESLPVSSKNLAQVKGSYSESSEAAQLEEVTSVEANSKDS
  61 KPKVEEDTGDPFGFDSDDESLPVSSKNLAQCKGSYSESSEAAQLEEVTSVEANSKCS

121 HVVEDTVVSEKQFPLEGTILGKEKSTNRIVEDDASISSCRKITSDKVENPSEEHEKNS
 121 HVVGEDSFASEKQLLVEDTILGKEKSISRIPEDNAKSSCDKILTSEKVENPSEEHEKQS

181 HHISKNADDSTKKPNAETIVASEIKETN-----DTWNSQGKRRESPSEISPIKGSVRTC
 181 HHISKNADDSTKKPNAETVVASETKADETKETNDTWNSQSGKRIESPSESCLVKGSVRTC

237 DEEWDNDFEDIRSEDCILSLDSDPLLEMKDDDKK---RIENLNEAYEEDIVQSVLRFDS
 241 DEEWDNDFEDIRSEDCILSLDNESLLEMDDDJFKRIGGLENLNETEEEDIPQSVLRFSN

294 CRTYCRANKTISSQGASNFDKLMDGTSCALAKANSESSKDGLNQAKKGCVSCGTSFRGTV
 301 CRTYCRANYARSSQGASNFDKLMDGTSCSLAKANSESSKDGLNQAKKGSNSCGTSSFRGTV

354 GRTRDYTVLHPSCLSVCNVTIQDTMERSMDEFTASTPADLGEAGRLRKKADIATSRTTTR
 361 GRTRDYTVLHPSCLSVCNVTIQDTMERSMDEFTASTPADLGEAGRLRKKADIATSKTTTR

414 FRPSNTRSKKDVRLEFTGFEDHETGG-DEGGSGSSNYKIKYFGFDDLSESEDD-DDDCQV
 421 FRPSNTRSKKDVRLEFTGFEDHCETGCDEGGSGSSNYKIKYFGFDDLSESEDD-DDDCQV

473 ERKTSKKRTKTAPSPSLQPPPESNDNSQDSQSCTNNAENLDFTEDLPGVPESVKKPINKG
 481 ERKTDKKRTKTAPSPSCQPPPESSDNSQDSQSCTNNAENLDFTEDLPGVPESVKKPISKG

533 GDKSKENTRKIFSGPKRSPTKAVYNARHWNHPDSEELPGPEVVKPQSVTVRLSSKEPNQK
 541 GDKSKENTRKIFSGPKRSPTKAVYNARHWNHPDSEELPGPPILKPQRVTVRLSSKEPNQK

593 DDGVFKAPAPFSKVIKTVTIPTQPYQDIVTALKCENEDKELYTVVQHVKHFNDVVEFGEN
 601 DDGVFKAPAPHDKVIKTVTIPTQPYQEIVTALKCRAEDKELYTVVQHVKHFNDVVEFGEN

653 QEFTDDIEYLLSGLKSTQPLNTRCLSVISLATKCAMPSFRMHLRAHGMVAMVFKTLDDSC
 661 QEFTDDIEYLLSGLKSTQPLNTRCLSVISLATKCAMPSFRMHLRAHGMVAMVFKTLDDSC

713 HHQNLSLCTAALMYILSRDRLNMDLDRASLDLMIRLVELEQDASSAKLLNEKDMNKIKER
 721 HHQNLSLCTAALMYILSRDRLNMDLDRASLDLMIRLVELEQDASSAKLLNEKDMNHIKEK

773 IPRLCETVHNKHLDLENITTGHLAMSTLLSLTSKRAGDWFKEELRLLGGLDRIVDKVKEC
 781 IRRLCETVHNKHLDLENITTGHLAMSTLLSLTSKRAGDWFKEELRLLGGLDHIVDKVKEC

833 VDHLSRI-EDEEKLVASLWGAERCLRVLESVTVHNPENQSYLIAYKDSQLISSAKALQH
 841 VDHLSRIDEDEEKLVASLWGAERCLRVLESVTVHNPENQSYLIAYKDSQLISSAKALQH

892 CEEIQQYNRAECSIGVADSPLBCQNVTNHVGKAVEDCMRAIIGVLLNLTNDNEWGSTK
 901 CELNQQYHRAENSIGVADSELBCHVTNHVGKAVEDCMRAIIGVLLNLTNDNEWGSTK

952 TGECDGLIGTAVNCVLQVPKYLPQEQRFDIRVLGLGLLINLVEYSARNRHCLVNRDTSCS
 961 TGECEGLIGTAVNCVLQVPKYLPQEQRFDIRVLGLGLLINLVEYSARNRHCLVNCTSCS

1012 FDSSICSGEGDCSLRIGGQVHAVQALVQLFLEREAAQLAESKTDELIKDAPTTQHDKSG
1021 FDSSTSSGEGDCSLRLAGQVHAVQALVQLFLEREAAQLAESKTDELIKDAPTTQHDKSG

1072 EWQETSGEIQWVSTEKTDGTEEKKKEEEDEELDLKALQHAGKHMEDCIVASYTALLLG
1081 EWQETSGEIQWVSTEKTDCAEEKKKEEEDEELDLKALQHAGKHMEDCIVASYTALLLG

1132 CLCQESPINVTTVREYLPEGDFSIMTEMLRKFLSFMNLTCAVGTTGQKSISRVIEYLEHC
1141 CLCQESPINVTTVREYLPEGDFSIMTEMLRKFLSFMNLTCAVGTTGQKSISRVIEYLEHC
```

The upper and the lower rows are the sequences of the human and the mouse WAPLs, respectively. White and gray parts indicate the same and similar amino acids, respectively.
The part in the frame is a region having similarity to the Drosophila WAPL.

Fig.6
A
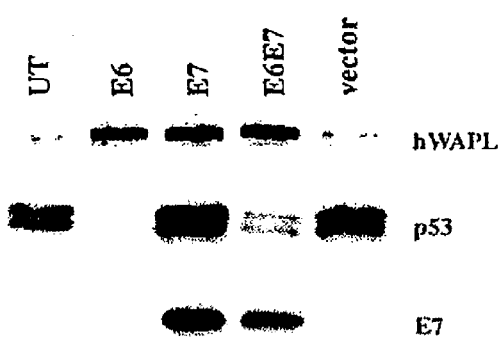
B
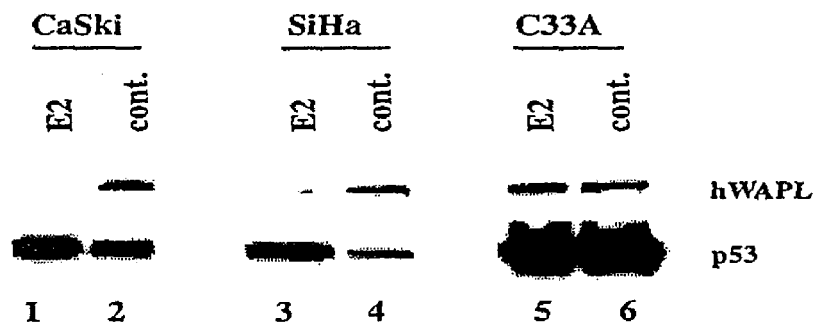

Fig. 7
A
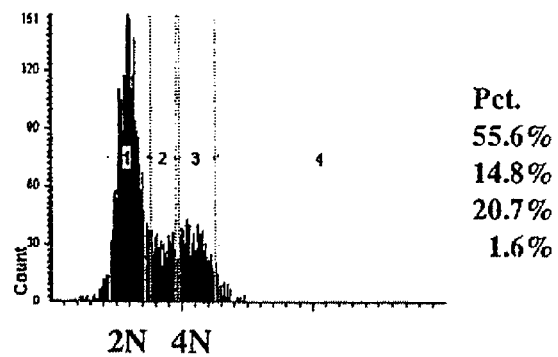
B
| micronuclei | + | − | total |
|---|---|---|---|
| GFP-hWAPL-NEGATIVE | 60 | 940 | 1000 |
| GFP-hWAPL-POSITIVE | 124 | 876 | 1000 |
$p < 0.01$
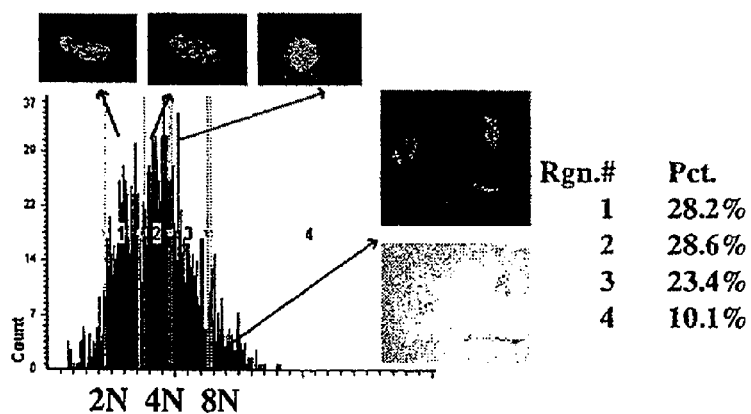

Fig.8
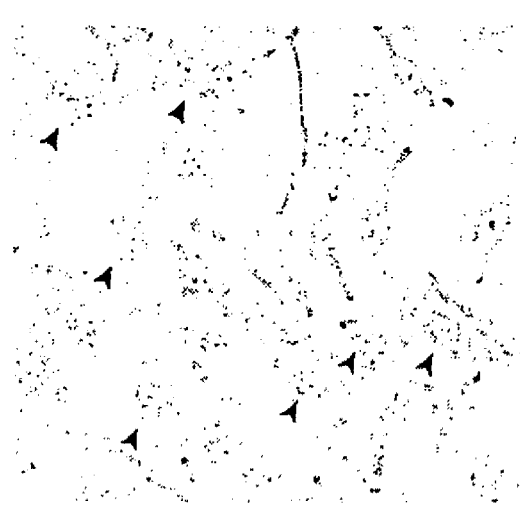 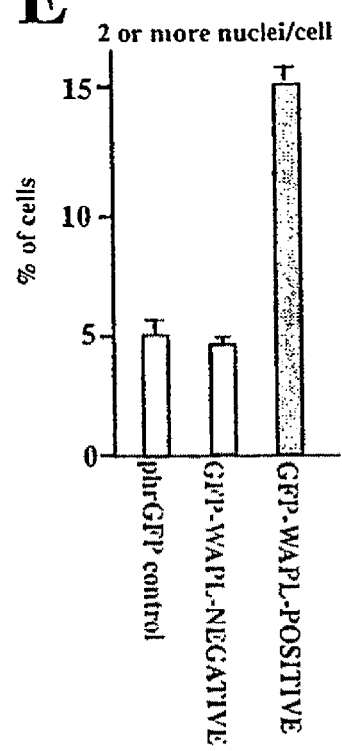

Fig.9
A
HA-WAPL 3T3    HA-3T3
B
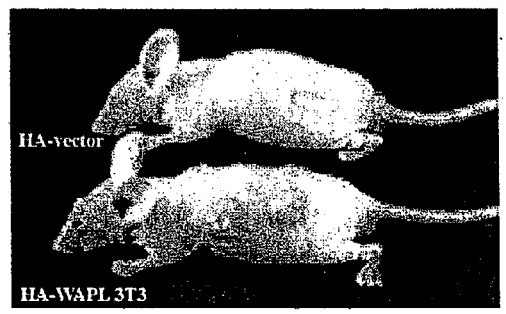
C
1    2    3    4    5    6
anti-hWAPL-C
HA
D
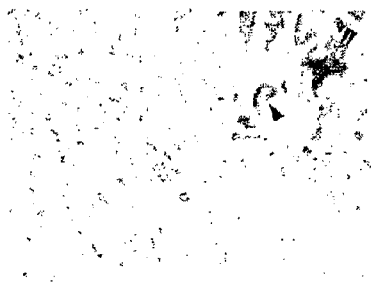

SIRNA CAPABLE OF INHIBITING THE EXPRESSION OF AN ONCOGENE INVOLVED IN CERVICAL CANCER

This is a divisional application of U.S. patent application Ser. No. 11/449,671, filed Jun. 9, 2006, now U.S. Pat. No. 7,432,358 which is a divisional application of U.S. patent application Ser. No. 10/758,562, filed Jan. 16, 2004, now U.S. Pat. No. 7,358,350 the entire disclosures of which are incorporated by reference herein.

FIELD OF THE INVENTION

The present invention relates to a novel oncogene from human, which is involved in development of human cervical cancer, a recombinant protein derived from the oncogene and uses thereof in medical applications.

BACKGROUND ART

There are many documents reporting that chromosome instability is involved in development of a cancer. In addition, it has been recently demonstrated that a defect in a molecule controlling a checkpoint during the G2/M phase in a cell cycle causes chromosome instability. However, since in many carcinoma cells, a gene defect in a molecule controlling a checkpoint in the cell is not frequently observed, a mechanism of inducing chromosome instability, which is substantially involved in onset of the cancer, remains still unclear in many aspects. types of HPV-16 or HPV-18. In a cervical cancer tissue, HPV infection has been observed at a frequency of 90% or more. In a development mechanism of cervical cancer induced by HPV infection, E6 and E7 gene products of the virus play an important role. Specifically, it is known that E6 accelerates a process for digesting p53 tumor suppressor protein, while E7 blocks canceration-inhibiting activity of pRB (retinoblastoma) tumor suppressor protein that is a Rb gene product, which two steps result in tumorigenesis. A specific oncogenic protein activated by HPV infection has not, however, been identified yet. Particularly, E6 and E7, viral gene products of HPV, induce chromosome instability and characterize a cell, but detail of its mechanism directly related there to is left substantially unknown in variety of aspects. For approaching to treatment of cervical cancer, it is, therefore, very important to identify an oncogenic protein as a target for HPV and an encoding oncogene thereof. Cervical cancer progresses from a precancerous state, i.e., dysplasia (epithelial dysplasia of cervical squamous cell) to invasive cancer. Depending on a case, the disease may remain in the dysplasia stage without progressing to cancer. On the other hand, there are considerable cases where dysplasia may rapidly progress to an advanced cancer. In view of the situation, it may be important for more accurate cancer diagnosis to identify a molecule directly involved in development of cervical cancer.

DISCLOSURE OF INVENTION

As described above, in the process where HPV infection of cervical epithelial cell induces development of an invasive cancer via a precancerous state, dysplasia, its direct origin would be considered to be a mechanism where an expression-inhibiting activity of p53 tumor suppressor protein or pRB tumor suppressor protein, which has inhibited expression of some oncogene, is damaged, and the damage leads the oncogene to a high-level expression state. Therefore, the full nucleotide sequence of the oncogene and an oncogenic protein encoded thereby must be first identified, which opens a way for developing means for inhibiting the biochemical functions of the oncogenic protein and further means for blocking a cancerization mechanism advanced by the oncogenic protein.

Furthermore, identification of the full nucleotide sequence of the oncogene and the amino acid sequence of the oncogenic protein encoded therein may allow us to produce a nucleic acid probe for detecting expression of an mRNA transcribed from the oncogene or to generate a specific antibody to the oncogenic protein with use of a recombinant oncogenic protein thereof. In other words, it may allow us to develop diagnosis means utilizing the nucleic acid probe or specific antibody, which is useful for diagnosing an early step of developing course to an invasive cancer via a precancerous state, dysplasia, that is caused by HPV infection in uterine cervix.

For solving the above problems, an aim of the present invention is to identify the full nucleotide sequence of a novel oncogene from Human and the amino acid sequence of an oncogenic protein encoded therein, which is directly involved in a cancerization mechanism in, for example, cervical cancer caused by HPV infection into cervical epithelial cell and, and also to provide a full-length polynucleotide encoding a peptide chain of the oncogenic protein, that is derived from the novel oncogene, which can be used for recombinant production of the oncogenic protein, as well as the peptide chain of the oncogenic protein recombinantly produced therewith.

We have intensely studied for solving the above problems, and finally have found and cloned a gene increasing expression in a cervical cancer cell when adding an environmental hormone thereto. We have concluded that the gene cloned is one of oncogenes, because (1) the gene is highly expressed in a carcinoma cell;
(2) cervical cancer is caused by HPV infection, and expression of E6 and E7 proteins by transducing E6 and E7 genes from HPV to the cell enhance the expression of said gene;
(3) p53 protein inhibits activity of the promoter region in said gene;
(4) lack or mutation of p53 protein is indeed involved in development of cervical cancer;
(5) expression of said gene can be inhibited by a double strand of interfering short-chain RNA (siRNA) to arrest growth of the cancer, and after further investigation, have achieved the present invention.

Thus, an oncogene polynucleotide according to the present invention is a novel oncogene polynucleotide derived from human involving development of cervical cancer, comprising a nucleotide sequence encoding an amino acid sequence of SEQ. ID. No. 1. In particular, it is the polynucleotide, wherein the nucleotide sequence encoding the amino acid sequence of SEQ. ID. No. 1 is a nucleotide sequence of SEQ. ID. No. 2.

The present invention also provides an invention of a peptide or its salts produced recombinantly, based on the above oncogene polynucleotide according to the present invention. Specifically, the recombinant peptide of the present invention is a recombinant peptide or its salts, comprising the amino acid sequence of SEQ. ID. No. 1 or a partial amino acid sequence of the amino acid sequence. In particular, it may be a recombinant oncogenic protein comprising the amino acid sequence of SEQ. ID. No. 1. The present invention also provides a recombinant vector comprising a polynucleotide encoding the recombinant peptide, which is usable for preparing said recombinant peptide therewith. For example, when aimed is the recombinant oncogenic protein of the present invention consisting of the amino acid sequence of SEQ. ID. No. 1, said recombinant vector therefor is a recombinant vector containing an oncogene polynucleotide comprising a nucleotide sequence encoding the amino acid sequence of SEQ. ID. No. 1, particularly containing a polynucleotide wherein the nucleotide sequence encoding the amino acid sequence of SEQ. ID. No. 1 is a nucleotide sequence of SEQ. ID. No. 2.

The present invention also provides a transformed cell produced by transforming a host cell using said recombinant vector; for example, a transformed cell produced by transforming a host cell with the recombinant vector targeted to said recombinant oncogenic protein of the present invention. Therefore, a process for producing the recombinant peptide or its salts of the present invention is a process for producing a recombinant peptide or its salts derived from an oncogene of the present invention comprising the steps of:

culturing the above transformed cell to allow the transformed cell to produce the recombinant peptide of the present invention; and collecting the recombinant peptide produced from the culture. In particular, it may be preferably a process for producing a recombinant oncogenic protein of the present invention comprising the steps of:

culturing said transformed cell in which the full-length gene DNA has been transformed to allow the transformed cell to produce the recombinant oncogenic protein of the present invention; and collecting the recombinant oncogenic protein produced from the culture.

With use of the above recombinant peptide of the present invention, the present invention provides an invention of an antibody that is a specific antibody generated using the recombinant peptide as an immunogen. For example, an antibody of the present invention may be an antibody exhibiting a specific reactivity to the partial amino acid sequence of 623 to 1185 region of the amino acid sequence of SEQ. ID. No. 1.

Furthermore, the present invention provides an antibody reagent kit for an antigen-antibody reaction comprising said specific antibody, available for detecting an oncogenic protein comprising the amino acid sequence of SEQ. ID. No. 1 or a peptide fragment derived from the oncogenic protein. Alternatively, the present invention provides a diagnosis kit being usable for detection of an oncogenic protein comprising the amino acid sequence of SEQ. ID. No. 1 or a peptide fragment derived from the oncogenic protein by means of an antigen-antibody reaction, comprising the specific antibody of the present invention.

The present invention also provides an antisense polynucleotide comprising a complementary nucleotide sequence to a partial nucleotide sequence of the nucleotide sequence of SEQ. ID. No. 2, which is a DNA fragment having at least a length selected from the region of 15 to 300 bases. In addition, as for a probe hybridization kit according to the present invention, it also provides a probe hybridization kit available for detecting an mRNA comprising the nucleotide sequence of SEQ. ID. No. 2, its partial nucleotide sequence therein or cDNA prepared by the mRNA, comprising the above antisense polynucleotide as the DNA probe. Alternatively, the present invention provides also a diagnosis kit available for detecting expression of mRNA comprising the nucleotide sequence of SEQ. ID. No. 2, which is translated into an oncogenic protein comprising the amino acid sequence of SEQ. ID. No. 1, by means of a probe hybridization method, comprising said antisense polynucleotide as the hybridization probe.

On the other hand, the present invention also provides a primer pair for PCR amplification of cDNA comprising the nucleotide sequence of SEQ. ID. No. 2, consisting of paired primers of:

```
a nucleotide sequence                     (SEQ ID NO: 5)
5'-TTGGATCCATGACATCCAGATTTGGGAAAACATACAGTAGG-3';
and a nucleotide sequence                     (SEQ ID NO: 4)
5'-TTGAATTCCTAGCAATGTTCCAAATATTCAATCACTCTAGA-3',
``` and also the present invention provides a primer pair for PCR amplifying a partial chain in cDNA comprising the nucleotide sequence of SEQ. ID. No. 2, consisting of paired primers of:

```
                                          (SEQ ID NO: 5)
      5'-GAATTCATAGGCACAGCGCTGAACTGTGTG-3';
      and (SEQ ID NO: 6)
      5'-TTGAATTCCTAGCAATGTTCCAAATATTCA-3'.
```

Otherwise, as for an invention of a double strand of an short-chain interfering RNA, the present invention provides a double strand of an short-chain interfering RNA capable of inhibiting expression of mRNA comprising the nucleotide sequence of SEQ. ID. No. 2 in a cervical cancer cell, wherein the double strand of the siRNA has a nucleotide sequence: CGGACTACCCTTAGCACAA (SEQ ID NO: 7). In addition, it may be also applied to a pharmaceutical composition for inhibiting expression of mRNA comprising the nucleotide sequence of SEQ. ID. No. 2 in a cervical cancer cell to arrest growth of the carcinoma cell, comprising said double strand of short-chain interfering RNA of the present invention.

BRIEF DESCRIPTION OF DRAWINGS

FIG. 2 shows an alignment of amino acids identical or similar to those in the dWAPL in a partial amino acid sequence of 623 to 1185 amino acids lying on the C-terminus side for the hWAPL of the present invention.

FIG. 3 shows very high homology between the amino acid sequences of a human WAPL protein and a mouse WAPL protein.

FIG. 6 shows (A): Western blotting for confirming expression of the hWAPL protein, which is induced by E6 and E7 recombinant proteins derived from HPV 16, and cleavage of the p53 suppressor protein thereby in HDK1 cell; and (B): Western blotting for confirming inhibition of transcription of E6 and E7 genes, increase in a p53 suppressor protein level and inhibition of expression of the hWAPL protein by BPV-derived E2.

FIG. 7 shows (A): chromosome instability and increase of polyploid; and (B): increase in a frequency of micronuclei formation induced by over-expression of a GFP-hWAPL fused protein in HeLa cell.

FIG. 8 shows chromosome instability and increase in a frequency of multinucleation induced by over-expression of a GFP-hWAPL fused protein in a HeLa cell.

FIG. 9 shows cancerization induction of NIH 3T3 fibroblast by the hWAPL protein, specifically (A): formation of a focus structure in culturing a HA-hWAPL 3T3 cell strain; (B): formation of a tumor in a site in a nude mouse, to which the HA-hWAPL 3T3 cell strain has been injected; (C): over-expression of the HA-tagged hWAPL protein in a tumor forming region; and (D): heterotypic mitosis in a cancerized cell.

BEST MODE FOR CARRYING OUT THE INVENTION

The present invention will be described in detail hereafter.

We have searched for a human-derived protein which is inducing factor for chromosome instability, assuming that chromosome instability would be considerably involved in cancerization mechanism in a cervical cancer cell. We have searched particularly for a protein having high potentiality for inducing heteroploidy or isogene formation among chromosome instability events.

We have noticed that dWAPL protein has been reported as a protein controlling a heterochromatin structure during an interkinesis in a meiosis process, among a variety of proteins derived from *Drosophila melanogaster* (fruit-fly) whose genomic genes have been most studied among animals. Specifically, we have found that when such a function that the protein exhibits for controlling the heterochromatin structure is expressed in a mitosis process in a normal cell, heteroploidy or isogene formation may be occasionally induced. We have first studied whether a protein corresponding to such a dWAPL is actually encoded on a human genomic gene. Based on the nucleotide sequence of the dWAPL gene reported (GenBank accession No. U40214), we have searched for fragments showing significant similarity from cDNA fragments registered in GenBank as gene fragments originated from human and have selected the KIAA0261 fragment as that comprising a nucleotide sequence similar to the dWAPL gene.

For identifying a full-length cDNA comprising the KIAA0261 fragment, we have searched in the EST database for a human-derived expression-tag nucleotide sequence, which may be a fragment comprising an un-translation part which is presumably an upstream nucleotide sequence lying in the 5'-side of the KIAA0261 fragment, and have selected EST clones: BE410177, BF79516 and BE257022.

We have determined an upstream nucleotide sequence lying in the 5'-side of the KIAA0261 fragment, using a 5'-RACE method with reference to the EST clones. Furthermore, since there is high probability that a protein having a function similar to the dWAPL is actually expressed in a cell having a meiosis process, we have cloned a full-length cDNA comprising the nucleotide sequence of the KIAA0261 fragment as well as the upstream nucleotide sequence determined above in the 5'-side thereof, using a commercially available cDNA library, i.e., a human testicular cDNA kit (Marathon-Ready™ cDNA Kit; Clontech Inc.) as a template.

Figure 1:
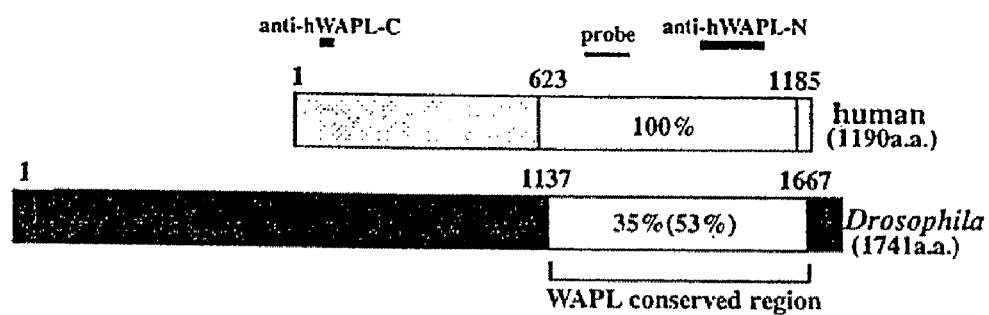
FIG. 1 shows comparison of an amino acid sequence between a dWAPL of Drosophia reported and an hWAPL of the present invention.

Practical sequencing has indicated that the coding region in the cloned full-length cDNA has 3570 base pairs, deducing an amino acid sequence with 1190 amino acids corresponding thereto. It is referred to "human WAPL (hWAPL)" as a human-derived protein similar to the dWAPL protein, and the corresponding gene is referred to as "hWAPL gene". The full-length nucleotide sequence that is corresponding to the ORF in the hWAPL gene is represented by SEQ. ID. No. 2, and the deduced amino acid sequence of the hWAPL protein is represented by SEQ. ID. No. 1. Comparison of the amino acid sequence encoded by the ORF of the hWAPL gene of the present invention, i.e., the deduced amino acid sequence of the hWAPL protein, with the amino acid sequence of the dWAPL protein indicates, as shown in FIG. 1, that there is an identity of 35% and a similarity of 53% for a partial sequence of amino acids 623 to 1185 lying in region of the C-terminus. The amino acids exhibiting such an identity and a similarity are shown in FIG. 2.

In addition, we have cloned a cDNA encoding a mouse-derived homologue thereto, a mouse WAPL protein, assuming that some mammals other than human may have also a corresponding protein. After sequencing it, the amino acid sequences encoded therein were compared. In practice, it has been confirmed that the human WAPL protein and the mouse WAPL protein shows very high homology to each other. FIG. 3 shows the result of comparative alignment. We have registered the full-length nucleotide sequence for coding region in the human WAPL gene under an accession No. AB065003 in DDBJ/EMBL/GenBank.

Figure 4:
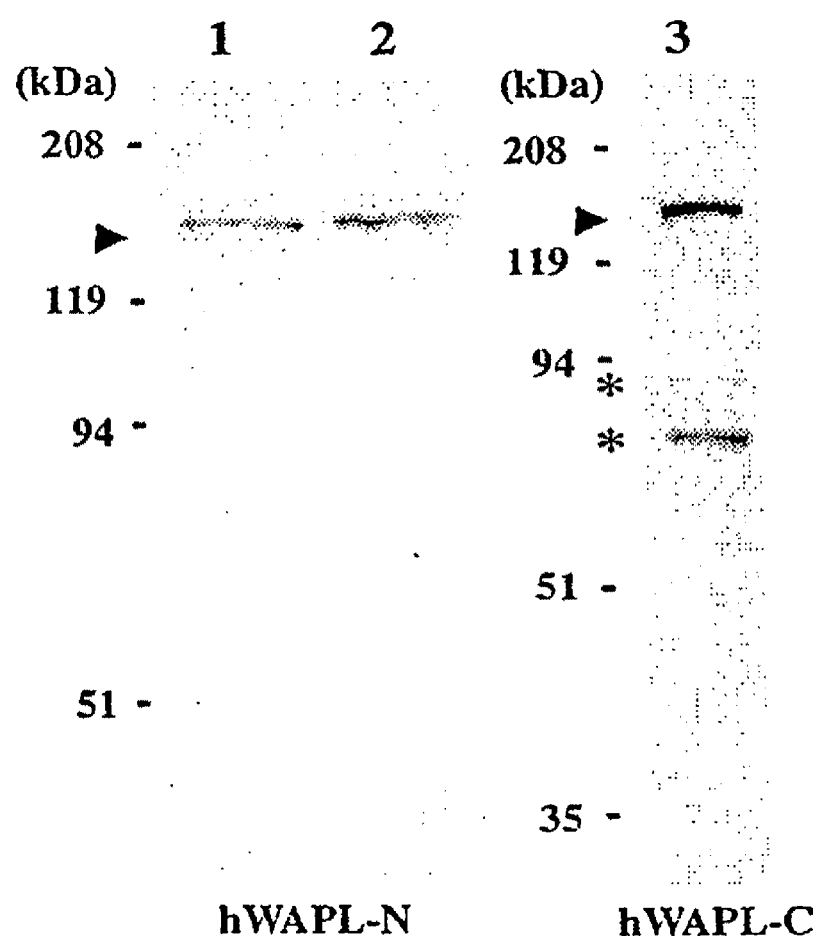
FIG. 4 shows the results of Western blotting analysis for extracts from Saos-2 cell (lanes 2, 3) and NIH3T3 cell (lane 1) by using an anti-hWAPL-N antibody and an anti-hWAPL-C antibody.

We have conducted Western blotting analysis for extracts from Saos-2 cell and NIH3T3 cell, using an anti-hWAPL-N antibody and an anti-hWAPL-C antibody, which are antibodies specific to the peptide chain in the human WAPL protein, as explained in Example 6. As shown in FIG. 4, the results have revealed a band of a protein reactive to the antibody with approximately 140 kDa. Thus, it has been confirmed that the human WAPL protein is actually present in the human-derived cell in some extent.

Furthermore, based on the following various confirmation methods:

Example 2: expression of the hWAPL gene in a human cancer tissue;

Example 3: induction of expression of the hWAPL gene by E6 and E7 derived from HPV type 16;

Example 4: inhibition of promoter activity of the hWAPL gene product by the p53 suppressor protein;

Example 7: induction of chromosome instability by the hWAPL protein;

Example 8: induction of cancerization of NIH 3T3 fibroblast by the hWAPL protein, it can be concluded that the hWAPL gene is an oncogene at least involved in a mechanism of development of cervical cancer.

The plasmid pGEMhWAPL comprising the full-length cDNA of the hWAPL gene, which is used in producing the transformant containing the full-length cDNA of the WAPL gene; *Escherichia coli* DH5 pGEMhWAPL strain that was obtained in Example 1, as described below, have been deposited on Jan. 7, 2003 as an original deposition date, in International Patent Organism Depositary (National Institute of Bioscience and Human-Technology) in National Institute of Advanced Industrial Science and Technology at Chuo $6^{th}$, 1-1-1, Higashi, Tsukuga, Ibaragi, 305-8566, under a deposit number of FERM BP-8269 in the International Depositary Authority under the Budapest Treaty.

We have also confirmed that expression of the hWAPL protein as a hWAPL gene product is inhibited by using a double strand of short-chain interfering RNA (siRNA). Specifically, a double strand of short-chain interfering RNA (siRNA) exhibiting such expression inhibition activity may include, for example, that having a nucleotide sequence: CGGACTACCCTTAGCACAA (SEQ ID NO: 7). In such a case, further growth of the carcinoma cell is also inhibited, so that development of the cancer can be arrested.

As for a protein having an amino acid sequence identical or substantially identical to the amino acid sequence of SEQ. ID. No. 1 of the present invention (hereinafter, sometimes referred to as "a protein of the present invention"), examples thereof may include an amino acid sequence having a homology of about 70% or more, preferably about 80% or more, more preferably 90% or more, most preferably about 95% or more with the amino acid sequence of SEQ. ID. No. 1.

As for the protein comprising an amino acid sequence identical or substantially identical to the amino acid sequence of the SEQ. ID. No. 1, preferred may be such a peptide that has an amino acid sequence substantially identical to the amino acid sequence of SEQ. ID. No. 1 and possesses a substantially equivalent activity to the protein having the amino acid sequence of SEQ. ID. No. 1.

The substantially equivalent activity may include, for instance, activity of the protein comprising the amino acid sequence of SEQ. ID. No. 1, such as a function for inducing cancer, enzymic activity, transcribing activity and binding activity with a binding protein therefor.

The term "substantially equivalent" as used herein means that these activities are identical in nature (for example, biochemically or pharmacologically).

Examples of the amino acid sequence being identical or substantially identical to the amino acid sequence of SEQ. ID. No. 1 include (i) the amino acid sequence of SEQ. ID. No. 1;

(ii) an amino acid sequence which has deletions of 1 to 30, preferably 1 to 20, more preferably 1 to 10 amino acids from the amino acid sequence of SEQ. ID. No. 1;

(iii) an amino acid sequence which has addition of 1 to 30, preferably 1 to 20, more preferably 1 to 10 amino acids to the amino acid sequence of SEQ. ID. No. 1;

(iv) an amino acid sequence which has insertion of 1 to 30, preferably 1 to 20, more preferably 1 to 10 amino acids into the amino acid sequence of SEQ. ID. No. 1;

(v) an amino acid sequence which has replacements of 1 to 30, preferably 1 to 20, more preferably 1 to 10 amino acids in the amino acid sequence of SEQ. ID. No. 1 with other amino acids; and (vi) an amino acid sequence which has combinational modification of two or more selected from the above (ii) to (v).

An example of a protein of the present invention may be a protein comprising the amino acid sequence of SEQ. ID. No. 1.

A partial peptide of the present invention may be any of partial peptides of the protein of the present invention described above, and generally preferred is a peptide that is consisted of at least 5 or more, preferably at least 10 or more amino acids, and further preferably has activity equivalent to a protein of the present invention.

In a protein of the present invention or its partial peptide (hereinafter, sometimes referred to as "proteins of the present invention"), the left end is N-terminus (amino terminus) while the right end is C-terminus (carboxy terminus) according to conventional notation for peptide.

In a protein of the present invention including a protein comprising amino acid sequence of the SEQ. ID. No. 1, C-terminal may be selected from carboxy (—COOH), carboxylate (—COO$^-$), amide (—CONH$_2$) and ester (—COOR).

Examples of R for the ester include $C_{1-6}$-alkyls such as methyl, ethyl, n-propyl, isopropyl and n-butyl; $C_{3-8}$-cycloalkyls such as cyclopentyl and cyclohexyl; $C_{6-12}$-aryls such as phenyl and α-naphthyl; phenyl-$C_{1-2}$-alkyls such as benzyl and phenethyl; $C_{7-14}$-aralkyls such as α-naphthyl-$C_{1-2}$-alkyls including α-naphthylmethyl; and pivaloyloxymethyl commonly used as ester for oral application.

When a protein of the present invention has a carboxy group (or carboxylate) in a position other than C-terminus, a protein in which the carboxy group is amidated or esterified is also a protein of the present invention. The ester here may be the C-terminal ester described above.

Furthermore, examples of a protein of the present invention include a protein in which an amino group in an N-terminal amino acid residue (for example, methionine residue) is protected by a protective group such as $C_{1-6}$-acyl including $C_{1-6}$-alkanoyl such as formyl and acetyl; a protein in which N-terminal glutamic acid residue formed by in vivo cleavage is converted into form of pyroglutamic acid; a protein in which a substituent on a side chain in an amino acid residue in the molecule (for example, —OH, —SH, amino, imidazole, indole and guanidino) is protected by an appropriate protective group (for example, such as $C_{1-6}$-acyls including typically $C_{1-6}$-alkanoyl such as formyl and acetyl); and a conjugated protein such as a so-called glucoprotein in which a sugar chain is linked.

A salt of a protein of the present invention may be a salt with a physiologically acceptable acid (for example, inorganic and organic acids) or base (for example, an alkali metal salt), particularly preferably a physiologically acceptable acid-addition salt. Examples of such a salt include salts with inorganic acids such as hydrochloric acid, phosphoric acid, hydrobromic acid and sulfuric acid, and with organic acids such as acetic acid, formic acid, propionic acid, fumaric acid, maleic acid, succinic acid, tartaric acid, citric acid, malic acid, oxalic acid, benzoic acid, methanesulfonic acid and benzenesulfonic acid. Hereinafter, such a salt is also included in a protein of the present invention.

A protein of the present invention or its salt may be prepared by a known process for purification of a protein from human or warm-blooded mammalian cells, or alternatively by culturing a transformant produced by transformation with a DNA encoding the protein described below.

When producing from a human or mammal tissue or cell, the human or mammal tissue or cell is homogenized and extracted with an acid. The extract is then purified by combined chromatographical procedures such as reverse phase chromatography and ion-exchange chromatography to isolate a desired product.

A polynucleotide encoding an oncogenic protein of the present invention may be any polynucleotide comprising the above nucleotide sequence encoding an oncogenic protein of the present invention (DNA or RNA, preferably DNA). The polynucleotide may be a DNA or RNA such as an mRNA encoding an oncogenic protein of the present invention, which may be single or double stranded. When being double stranded, it may be a double-stranded DNA, a double-stranded RNA or a hybrid of DNA:RNA. When being single stranded, it may be a sense chain, i.e., a coding chain, or an antisense chain, i.e., a non-coding chain.

A polynucleotide encoding a protein of the present invention may be used to quantify an mRNA of a protein of the present invention, according to a known method or its modification, for example, a method described in Experimental Medicine Extra Edition "Novel PCRs and their applications", 15(7), 1997.

A DNA encoding a protein of the present invention may be any DNA comprising the above nucleotide sequence encoding a protein of the present invention, and may be a genome DNA, a genome DNA library, the above cell/tissue-derived cDNA, the above cell/tissue-derived cDNA library or a synthetic DNA.

A vector used for a library may be a bacteriophage, plasmid, cosmid or phagemid. A preparation of a total RNA or mRNA fraction from the cell or tissue may be used for amplification by a direct Reverse Transcriptase Polymerase Chain Reaction (hereinafter, referred to as "RT-PCR").

A nucleotide sequence available for a probe DNA of the present invention may be any sequence such as a DNA sequence which comprises a nucleotide sequence hybridizable with the nucleotide sequence of SEQ. ID. No. 2 under high stringent conditions and encodes a protein having an activity substantially equivalent to that of a protein comprising the amino acid sequence of SEQ. ID. No. 1.

A nucleotide sequence hybridizable with the nucleotide sequence of SEQ. ID. No. 2 under high stringent conditions may be a nucleotide sequence having a homology of about 70% or more, preferably about 80% or more, more preferably about 90% or more, further preferably about 95% or more with the nucleotide sequence of SEQ. ID. No. 2.

Hybridization may be conducted in accordance with a known method or its modification, for example, a method described in Molecular Cloning 2nd (J. Sambrook et al., Cold Spring Harbor Lab. Press, 1989). When using a commercially available library, hybridization can be conducted in accordance with an attached manual. More preferably, it can be conducted under high stringent conditions.

High stringent conditions may include, for example, a sodium concentration of about 19 to 40 mM, preferably about 19 to 20 mM and a temperature of about 50 to 70° C., preferably about 60 to 65° C., most preferably a sodium concentration of about 19 mM and a temperature of about 65° C.

More specifically, a DNA encoding a protein comprising amino acid sequence of the SEQ. ID. No. 1 may be a DNA comprising the nucleotide sequence of SEQ. ID. No. 2.

A DNA encoding a partial peptide of the present invention may be any DNA comprising a nucleotide sequence encoding the above partial peptide of the present invention, and may be a genome DNA, a genome DNA library, the above cell/tissue-derived cDNA, the above cell/tissue-derived cDNA library or a synthetic DNA.

A DNA encoding a partial peptide of the present invention may be a DNA comprising a partial nucleotide sequence of a DNA comprising the nucleotide sequence of SEQ. ID. No. 2, or a DNA comprising a partial nucleotide sequence of a DNA which comprises a nucleotide sequence hybridizable with the nucleotide sequence of SEQ. ID. No. 2 under high stringent conditions and encodes a protein having an activity substantially equivalent to that of a protein comprising the amino acid sequence of SEQ. ID. No. 1.

The nucleotide sequence hybridizable with the nucleotide sequence of SEQ. ID. No. 2 is defined as described above.

A hybridization method and the high stringent conditions may be as described above.

A polynucleotide comprising a part of a DNA sequence encoding a protein of the present invention or its partial peptide (hereinafter, sometimes referred to as "a protein of the present invention") or a part of a nucleotide sequence complementary to the DNA may encompass a DNA as well as an RNA encoding a protein of the present invention or its partial peptide.

According to the present invention, an antisense polynucleotide (nucleic acid) capable of inhibiting replication or expression of a protein gene of the present invention designed and synthesized on the basis of nucleotide sequence data on a DNA encoding the cloned or determined protein of the present invention. Such a polynucleotide (nucleic acid) can be hybridized with an RNA of a protein gene of the present invention to inhibit synthesis or activities of the RNA, or regulate or control expression of a protein gene of the present invention via interaction with an RNA related to a protein of the present invention. A polynucleotide complementary to a selected sequence in the RNA related to a protein of the present invention and a polynucleotide specifically hybridizable with the RNA related to a protein of the present invention are useful for regulating or controlling in vivo or in vitro expression of a protein gene of the present invention, and for treatment or diagnosis of a disease. The term "corresponding to" as used herein means homology or complementation to a particular sequence of a nucleotide including a gene, a nucleotide sequence or a nucleic acid. The term "corresponding to" in terms of relationship between a nucleotide, a nucleotide sequence or a nucleic acid and a peptide (protein) generally refers to an amino acid in a protein (peptide), a command derived from a sequence of a nucleotide (nucleic acid) or its complementary sequence. Examples of a preferable target domain may include a 5'-terminal hairpin loop, a 5'-terminal 6-base pair repeat, a 5'-terminal untranslation domain, a protein translation initiating codon, a protein coding domain, an ORF translation stop codon, a 3'-terminal non-translation domain, a 3'-terminal palindrome domain and a 3'-terminal hairpin loop in a protein gene of the present invention, but any domain in a protein gene of the present invention may be selected as a target.

Relationship between a given nucleic acid a polynucleotide complementary to at least a part of a target domain and between a target and a hybridizable polynucleotide can be called "antisense". Examples of an antisense polynucleotide include a polynucleotide comprising 2-deoxy-D-ribose, a polynucleotide comprising D-ribose, other types of polynucleotides as an N-glycoside of purine or pyrimidine base and other polymers comprising a non-nucleotide structure (for example, a commercially available protein nucleic acid and a synthetic-sequence specific nucleic acid polymer) or other polymer having a special bond although the polymer comprises a nucleotide having a configuration which can accept base pairing or base attachment as observed in a DNA or RNA. These may be a double-stranded DNA, a single-stranded DNA, a double-stranded RNA, a single-stranded RNA or a DNA:RNA hybrid. They may further include unmodified polynucleotides (or unmodified oligonucleotide), those having a known modification such as a tag known in the art, a capping, methylation, replacement of at least one natural nucleotide with an analogue and an intramolecular nucleotide modification; those having a non-charged bond (for example, methylphosphonate, phosphotriester, phosphoramidate and carbamate); those having a charged bond or sulfur-containing bond (for example, phosphorothioate and phosphorodithioate); those having a side chain group including a protein (a nuclease, a nuclease inhibitor, toxine, an antibody, a signal peptide and poly-L-lysine) or a sugar (for example, a monosaccharide); those comprising an inter-current compound (for example, acridine and psoralen); those comprising a chelating compound (for example, a metal, a radioactive metal, boron and an oxidizing metal); those comprising an alkylating agent; and those comprising a modified bond (for example, an α-anomer type nucleic acid). The terms "nucleoside", "nucleotide" and "nucleic acid" as used herein may include not only those containing purine and pyrimidine bases but also those further containing another modified heterocyclic base. Such a modified substance may contain methylated purine and pyrimidine, acylated purine and pyrimidine or other heterocycles. A modified nucleoside and a modified nucleotide may be modified in a sugar moiety; for example, one or more hydroxyls may be replaced with a halogen or aliphatic group, or may be converted into another functional group such as ether and amine.

An antisense polynucleotide (nucleic acid) of the present invention is an RNA, DNA or modified nucleic acid (RNA, DNA). Examples of a modified nucleic acid include, but not limited to, a sulfur derivative or thiophosphate derivative of a nucleic acid and those resistant to decomposition by a polynucleosideamide or an oligonuclesideamide. An antisense nucleic acid of the present invention may be preferably designed, for example, such that the antisense nucleic acid is made more stable in a cell, the antisense nucleic acid has a higher permeability in a cell, it has affinity to a target sense chain, or if it is toxic, the antisense nucleic acid is made less toxic.

A variety of such modifications are well known in the art, and have been disclosed in, for example, J. Kawakami et al., Pharm Tech Japan, Vol. 8, pp. 247, 1992; Vol. 8, pp. 395, 1992; S. T. Crooke et al. ed., Antisense Research and Applications, CRC Press, 1993.

An antisense nucleic acid of the present invention may comprise a converted and/or modified sugar, base and/or bond, and thus may be provided as a special form such as a liposome and a microsphere, may be applied in gene therapy or may be provided as an adduct. Examples of such an adduct include a polycationic adduct such as polylysine acting as a neutralizer to a charge in a phosphate structure and a hydrophobic adduct such as a lipid enhancing interaction with a cell membrane or increasing an uptake of a nucleic acid (for example, a phospholipid and cholesterol). Examples of a lipid preferable for addition include cholesterol and its derivatives (for example, cholesteryl chloroformate and cholic acid). It may be attached to a 3'- or 5'-terminal in a nucleic acid via a base, sugar or intramolecular nucleoside bond. Another available group may be, for example, a capping group specifically located at a 3'- or 5'-terminal in a nucleic acid for preventing decomposition by a nuclease such as exonuclease and RNase. Examples of such a capping group include, but not limited to, those known as a hydroxyl-protecting group in the art such as glycols including polyethyleneglycol and tetraethyleneglycol.

Inhibition of activity of antisense nucleic acid can be determined using a transformant of the present invention, an in vivo or in vitro gene expression system of the present invention, or an in vivo or in vitro translation system in a protein of the present invention. The nucleic acid may be applied to a cell by any of various known methods.

A DNA encoding a protein of the present invention may be labeled by a known method; for example, isotope labeling, fluorescent labeling (for example, fluorescent labeling with fluorescein), biotinylation and enzyme labeling.

A DNA fully encoding a protein of the present invention may be cloned by amplification by a known PCR using a synthetic DNA primer comprising a partial nucleotide sequence in a protein of the present invention, or selecting a DNA integrated in an appropriate vector by hybridization with that labeled with a DNA fragment or synthetic DNA encoding a partial or full-length of a protein of the present invention. Hybridization may be conducted by, for example, a method described in Molecular Cloning 2nd, J. Sambrook et al., Cold Spring Harbor Lab. Press, 1989. When using a commercially available library, hybridization can be conducted in accordance with an attached manual.

A sequence of a DNA may be transformed using a known kit such as Mutan™-super Express Km (Takara Shuzo Co., Ltd.), Mutan™-K (Takara Shuzo Co., Ltd.), by a known method such as ODA-LA PCR, Gapped duplex method and Kunkel method or variation thereof.

Depending on an application, a DNA encoding a cloned peptide may be used as such or if desired used after digestion by a restriction enzyme or addition of a linker. The DNA may have ATG as a translation initiating codon at the 5'-terminal and TAA, TGA or TAG as a translation stop codon at the 3'-terminal. The translation initiating codon or the translation stop codon may be added using an appropriate synthetic DNA adapter.

An expression vector of a protein of the present invention may be produced by, for example, (i) excising a desired DNA fragment from a DNA encoding a protein of the present invention and (ii) ligating the DNA fragment in the downstream of a promoter in an appropriate expression vector.

Examples of a vector which can be used include plasmids derived from *E. coli* (for example, pBR322, pBR325, pUC12 and pUC13); plasmids derived from *Bacillus subtilis* (for example, pUB110, pTP5 and pC194); plasmids derived from an yeast (for example, pSH19 and pSH15); bacteriophages such as λ-phage; mammalian viruses such as retroviruses, vaccinia viruses and baculoviruses; pA1-11; pXT1; pRc/CMV; pRc/RSV; and pcDNAI/Neo.

A promoter used in the present invention may be any promoter appropriate to a host used in gene expression. For example, when using a mammalian cell as a host, an SR α-promoter, an SV40 promoter, an HIV-LTR promoter, a CMV promoter or an HSV-TK promoter may be used.

Among these, it is preferable to use a CMV (cytomegalovirus) promoter or an SR α-promoter. When a host is an *Escherichia coli*, a trp promoter, a lac promoter, a recA promoter, a λ-PL promoter, an lpp promoter and a T7 promoter are preferable; when a host is a *Bacillus*, an SPO1 promoter, an SPO2 promoter and a penP promoter are preferable; when a host is an yeast, a PHO5 promoter, aPGK promoter, a GAP promoter and an ADH promoter are preferable. When a host is an insect cell, a polyhedrin promoter and a P10 promoter are preferable.

If desired, another expression vector can be used, including those comprising an enhancer, a splicing signal, a poly-A addition signal, a selection marker and/or an SV40 replication origin (hereinafter, sometimes referred to as "SV40ori"). Examples of a selection marker include dihydrofolate reductase (hereinafter, sometimes referred to as "dhfr") gene [methotrexate (MTX) resistant], an ampicillin resistant gene (hereinafter, sometimes referred to as "Ampr") and a neomycin resistant gene (hereinafter, sometimes referred to as "Neo", G418 resistant). In particular, when using the dhfr gene as a selection marker using a dhfr gene deleted Chinese Hamster cell, integration of a desired gene may be selected using a thymidine deficient medium.

As a selection marker, a reporter gene or drug resistance gene is used (New Biochemical Experimental Lectures (Shin Seikagaku Jikken Koza) 2, nucleic acid III, 3.6 Mammalian cell expression vector, p84-103).

Examples of a combination of a drug resistance gene and a drug which can be used include:

(1) a combination of a puromycin-N-acetyltransferase gene and puromycin;

(2) a combination of an aminoglycoside phosphotransferase gene (APH) and G418;

(3) a combination of a hygromycin-B phosphotransferase gene (HPH) and hygromycin-B; and (4) a combination of xanthine-guanine phosphoribosyltransferase (XGPRT) and mycophenolate.

When a parent cell strain is a hypoxanthine-guanine phosphoribosyltransferase (HGPRT) or thymidinekinase (TK) deficient strain, a combination of these genes and HAT (hypoxanthine, aminopterin and thymidine) may be used.

Dihydrofolate reductase or ampicillin resistance gene may be used as a selection marker gene.

If necessary, a signal sequence appropriate for a host is added to the N-terminal of a protein of the present invention. When a host is an *Escherichia coli*, a PhoA signal sequence and an OmpA signal sequence may be used; when a host is a *Bacillus*, an α-amylase signal sequence and a subtilisin signal sequence may be used; when a host is an yeast, an MFα signal sequence and an SUC2 signal sequence may be used; when a host is a mammalian cell, an insulin signal sequence, an α-interferon signal sequence and an antibody-molecule signal sequence may be used.

A vector comprising a DNA encoding a protein of the present invention thus constructed may be used to produce a transformant.

A host may be, for example, an *Escherichia coli*, a *Bacillus*, an yeast, an insect cell, an insect or a mammalian cell.

Examples of an *Escherichia coli* include *Escherichia coli* K12 DH1 [Proc. Natl. Acad. Sci. USA), Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)] and C600 [Genetics, Vol. 39, 440 (1954)].

Examples of a *Bacillus* include *Bacillus subtilis* MI114 [Gene, Vol. 24, 255 (1983)] and 207-21 [Journal of Biochemistry, Vol. 95, 87 (1984)].

Examples of an yeast include *Saccharomyces cerevisiae* AH22, AH22R−, NA87-11A, DKD-5D and 20B-12; *Schizosaccharomyces pombe* NCYC1913 and NCYC2036; and *Pichia pastoris* KM71.

In terms of an insect cell, when the virus is AcNPV, an established cell derived from army worm larva (*Spodoptera frugiperda* cell; Sf cell), an MG1 cell derived from a midgut of *Trichoplusia ni*, a High Five™ cell derived from an egg of *Trichoplusia ni*, a cell derived from *Mamestra brassicae* or a cell derived from *Estigmena acrea* may be used. When the virus is BmNPV, an established cell derived from silkworm (*Bombyx mori* N cell; BmN cell) may be used. Examples of the Sf cell which can be used include an Sf9 cell (ATCC CRL1711) and an Sf21 cell, which have been described in Vaughn, J. L. et al., In Vivo, 13, 213-217 (1977)).

Examples of an insect include silkworm larvae [Maeda et al., Nature, Vol. 315, 592 (1985)].

Examples of a mammalian cell include a simian cell COS-7 (COS7), Vero, a Chinese Hamster cell CHO (hereinafter, referred to as "CHO cell"), a dhfr-gene deleted Chinese Hamster cell CHO (hereinafter, referred to "CHO(dhfr−) cell"), a murine L cell, a murine AtT-20, a murine myeloma cell, a rat GH3 and a human FL cell.

An *Escherichia coli* may be transformed in accordance with, for example, a method described in Proc. Natl. Acad. Sci. USA), Vol. 69, 2110 (1972) or Gene, Vol. 17, 107 (1982).

A *Bacillus* may be transformed in accordance with, for example, a method described in Molecular & General Genetics), Vol. 168, 111 (1979).

An yeast may be transformed in accordance with, for example, a method described in Methods in Enzymology, Vol. 194, 182-187 (1991) or Proc. Natl. Acad. Sci. USA, Vol. 75, 1929 (1978).

An insect cell or an insect may be transformed in accordance with, for example, a method described in Bio/Technology, 6, 47-55 (1988).

A mammalian cell may be transformed in accordance with, for example, a method described in Cell Technology Extra Issue 8, New Cell Technological Experiment Protocols. 263-267 (1995) (Shuju Co. Ltd.) or Virology, Vol. 52, 456 (1973).

Thus, a transformant which has been transformed with an expression vector comprising a DNA encoding a protein of the present invention can be obtained.

When culturing a transformant for which a host is an *Escherichia coli* or *Bacillus*, an appropriate medium used for culturing is a liquid medium containing a carbon source, a nitrogen source, inorganic materials and so on needed for growing the transformant. Examples of a carbon source include glucose, dextrin, soluble starch and sucrose. Examples of a nitrogen source include inorganic and organic materials such as ammonium salts, nitrates, corn steep liquor, peptone, casein, meat extract, soybean cake and potato extract. Examples of an inorganic material include calcium chloride, sodium dihydrogenphosphate and magnesium chloride. An yeast extract, vitamins and/or growth accelerating factors may be added. The medium desirably has a pH of about 5 to 8.

A preferable example of a medium for culturing an *Escherichia coli* may be an M9 medium containing glucose and casamino acid [Miller, Journal of Experiments in Molecular Genetics, 431-433, Cold Spring Harbor LaboHumanory, New York, 1972]. If necessary, an additional agent such as 3 β-indolylacrylic acid may be added for efficient promoter activity.

When a host is an *Escherichia coli*, culturing is generally conducted at about 15 to 43° C. for about 3 to 24 hours under, if necessary, aeration and/or agitation.

When a host is a *Bacillus*, culturing is generally conducted at about 30 to 40° C. for about 6 to 24 hours under, if necessary, aeration and/or agitation.

When culturing a transformant whose host is an yeast, examples of a culture medium which can be used include a Burkholder minimum medium [Bostian, K. L. et al, Proc. Natl. Acad. Sci. USA, Vol. 77, 4505 (1980)] and an SD medium containing 0.5% of casamino acid [Bitter, G. A. et al., Proc. Natl. Acad. Sci. USA, Vol. 81, 5330 (1984)]. A pH of the medium is preferably adjusted to about 5 to 8. Culturing is generally conducted at about 20 to 35° C. for about 24 to 72 hours under, if necessary, aeration and/or agitation.

When culturing a transformant in which a host is an insect cell or insect, a culture may be a Grace's Insect Medium (Grace, T. C. C., Nature, 195, 788 (1962)) containing additives such as 10% decomplemented bovine serum as appropriate. A pH of the medium is preferably adjusted to about 6.2 to 6.4. Culturing is generally conducted at about 27° C. for about 3 to 5 days under, if necessary, aeration and/or agitation.

When culturing a transformant in which a host is a mammalian cell, examples of a culture include an MEM medium containing about 5 to 10% fetal bovine serum [Science, Vol. 122, 501 (1952)], a DMEM medium [Virology, Vol. 8, 396 (1959)], an RPMI 1640 medium[the Journal of the American Medical Association, Vol. 199, 519 (1967)] and a 199 medium [Proceeding of the Society for the Biological Medicine, Vol. 73, 1 (1950)]. A pH of the medium is preferably adjusted to about 6 to 8. Culturing is generally conducted at about 30 to 40° C. for about 15 to 60 hours under, if necessary, aeration and/or agitation.

As described above, a protein of the present invention may be produced in an intracellular, cell-membrane or extracellular region of a transformant cell.

A protein of the present invention can be isolated and purified from the above culture by, for example, the following method.

A protein of the present invention can be extracted from cultured bacteria or cells by, as appropriate, a method where after culturing, the bacteria or the cells are collected by a known procedure, they are suspended in a proper buffer, the bacteria or the cells are lysed using ultrasonic, lysozyme and/or freezing and thawing, then they are centrifuged or filtrated to give a crude extract of a protein of the present invention. The buffer may contain a protein modifier such as urea and guanidine hydrochloride and a surfactant such as Triton X-100™. When a peptide is secreted into a culture medium, the bacteria or the cells are separated from the supernatant by a known method after culturing, and then the supernatant is collected.

A protein of the present invention contained in the culture supernatant or the extract thus obtained may be purified by an appropriate combination of known separation/purification methods. Examples of such known separation/purification methods include methods utilizing a solubility such as salting out and solvent precipitation; methods mainly utilizing a molecular weight difference such as dialysis, ultrafiltration, gel filtration and SDS-polyacrylamide gel electrophoresis; methods utilizing a charge difference such as ion-exchange chromatography; methods utilizing specific affinity such as affinity chromatography; method utilizing a hydrophobicity difference such as reverse phase high performance liquid chromatography; and methods an isoelectric point difference such as isoelectric focusing.

When the protein of the present invention thus obtained is a free form, it can be converted into a salt by a known method or a modification thereof. In reverse, when it is obtained as a salt, it can be converted into a free form or another salt by a known method or a modification thereof.

Before or after purification, a protein of the present invention produced by a recombinant may be attacked by an appropriate protein modifying enzyme to be modified as appropriate or to partially remove a peptide. Examples of a protein modifying enzyme include trypsin, chymotrypsin, arginyl-endopeptidase, protein kinase and glycosidase.

An antibody to a protein of the present invention (hereinafter, sometimes simply referred to as "an antibody of the present invention") may be either polyclonal or monoclonal as long as it is an antibody which can recognize an antibody to a protein of the present invention.

The antibody to a protein of the present invention can be produced by a known method for preparing an antibody or antiserum using a protein of the present invention as an antigen.

Preparation of a Monoclonal Antibody (a) Preparation of a Monoclonal Antibody Producing Cell A protein of the present invention is applied alone or in combination with a carrier and a diluent to a site in a warm-blooded animal where an antibody can be produced. For application, a Freund's complete or incomplete adjuvant may be applied for improving antibody-producing ability. It is generally applied once in 2 to 6 weeks and about 2 to 10 times in total. Examples of a warm-blooded animal include monkey, rabbit, dog, guinea pig, mouse, rat, sheep, goat and poultry, preferably mouse and rat.

For preparing a monoclonal antibody producing cell, an individual exhibiting an antibody titer from a warm-blooded animal immunized by an antigen such as mouse is selected and a spleen or lymph node is isolated 2 to 5 days after final immunization. An antibody producing cell contained in the isolated may be fused to a myeloma cell of the same or a different animal to prepare a monoclonal antibody producing hybridoma. An antibody titer in an antiserum can be determined by, for example, reacting a labeled peptide described later with the antiserum and then measuring a label activity bound to an antibody. Fusion may be conducted by a known method such as a Kaehler-Milstein method [Nature, 256, 495 (1975)]. Examples of a fusion accelerator include polyethyleneglycol (PEG) and Sendai virus, preferably PEG.

Examples of a myeloma cell include those of a warm-blooded animal such as NS-1, P3U1, SP2/0 and AP-1, preferably P3U1. A preferable number ratio of an antibody producing cell (spleen cell) to a myeloma cell is about 1:1 to 20:1, PEG (preferably PEG1000 to PEG6000) is added to a concentration of about 10 to 80%, and the cell fusion can be efficiently conducted by incubation at 20 to 40° C., preferably 30 to 37° C. for 1 to 10 min.

A monoclonal antibody producing hybridoma can be screened by any of various methods; for example, by adding a hybridoma culture supernatant to a solid phase (e.g., microplate) in which a peptide (protein) antigen has been adsorbed directly or in combination with a carrier, then adding an anti-immunoglobulin antibody (when a cell used for cell fusion is a murine cell, an anti-mouse immunoglobulin antibody is used) or protein A labeled with a radioactive agent or enzyme, and finally detecting a monoclonal antibody bound to the solid phase, or alternatively by adding a hybridoma culture supernatant to a solid phase in which an anti-immunoglobulin antibody or protein A has been adsorbed, adding a peptide labeled with a radioactive agent or enzyme, and finally detecting a monoclonal antibody bound to the solid phase.

A monoclonal antibody can be selected by a known method or its modification. It can be generally using a medium for a mammalian cell containing HAT (hypoxanthine, aminopterin and thymidine). A medium for selection and breeding may be any medium in which a hybridoma can be grown; for example, an RPMI 1640 medium containing 1 to 20%, preferably 0 to 20% fetal bovine serum, a GIT medium containing 1 to 10% fetal bovine serum (Wako Pure Chemicals Co. Ltd.) and a serum-free medium for culturing a hybridoma (SFM-101, Nissui Pharmaceutical Co., Ltd.). A culturing temperature is generally 20 to 40° C., preferably about 37° C. A culturing period is generally 5 days to 3 weeks, preferably 1 to 2 weeks. Culturing may be generally conducted under 5% gaseous carbon dioxide. An antibody titer in a hybridoma culture supernatant can be determined as described for determination of an antibody titer in the above antiserum.

(b) Purification of a Monoclonal Antibody

A monoclonal antibody can be separated and purified by a known method including separation/purification methods for an immunoglobulin such as salting out, alcohol precipitation, isoelectric precipitation, electrophoresis, an adsorption and desorption method with an ion exchanger (for example, DEAE), ultracentrifugation, gel filtration, and a specific purification in which an antibody is exclusively collected by an activated adsorbent such as an antigen-binding solid phase, protein A or protein G for dissociating the bond to obtain the antibody.

Preparation of a Polyclonal Antibody

A polyclonal antibody of the present invention can be prepared in accordance with a known method or its modification. For example, an immunogen (peptide antigen) or its complex with a carrier protein is prepared, a warm-blooded animal is immunized with it as described for a preparation process for the above monoclonal antibody, a product containing an antibody to a protein of the present invention is collected from the immunized animal, and after separation and purification, the antibody can be prepared.

In terms of a complex of an immunogen and a carrier protein for immunizing a warm-blooded animal, any type of carrier proteins and any mix ratio of the carrier to a hapten may be employed as long as an antibody can be efficiently produced to a hapten immunized by crosslinking to the carrier; for example, about 0.1 to 20 parts by weight, preferably about 1 to 5 parts by weight of bovine serum albumin, bovine thyroglobulin, hemocyanin or the like is coupled to 1 part by weight of the hapten.

Various condensing agents may be used for coupling of the hapten with the carrier, including glutaraldehyde, carbodiimide, activated maleimide ester and activated ester reagents having a thiol and/or a dithiopyridyl groups.

A condensation product is applied alone or in combination of a carrier and a diluent, to a site in a warm-blooded animal where an antibody can be produced. For application, a Freund's complete or incomplete adjuvant may be applied for improving antibody-producing ability. It is generally applied once in 2 to 6 weeks and about 3 to 10 times in total.

A polyclonal antibody can be collected from blood or ascites, preferably blood of a warm-blooded animal immunized as described above.

A polyclonal antibody titer in an antiserum can be determined as described for determination of an antibody titer in an antiserum. The polyclonal antibody can be separated and purified as described for separation and purification of the immunoglobulin in the course of separation/purification of the above monoclonal antibody.

An antisense DNA comprising a nucleotide sequence complementary or substantially complementary to a DNA encoding a protein of the present invention (hereinafter, the latter DNA is sometimes referred to as "a DNA of the present invention", and the former antisense DNA is sometimes referred to as "antisense DNA") may be any antisense DNA comprising a nucleotide sequence complementary or substantially complementary to a DNA of the present invention and capable of inhibiting expression of the DNA.

A nucleotide sequence substantially complementary to a DNA of the present invention may be, for example, a nucleotide sequence having a homology of about 70% or more, preferably about 80% or more, more preferably 90% or more, most preferably about 95% or more with the full or partial nucleotide sequence complementary to a DNA of the present invention (i.e., a complementary chain to a DNA of the present invention). Particularly preferred is an antisense DNA having a homology of about 70% or more, preferably about 80% or more, more preferably 90% or more, most preferably about 95% or more with a complementary chain to a nucleotide sequence of a domain encoding the N-terminal site of a protein of the present invention (for example, a nucleotide sequence near an initiating codon) in the full nucleotide sequence of the complementary chain to a DNA of the present invention. Such an antisense DNA can be prepared using, for example, a known DNA synthesizer.

There will be described applications of an oncogenic protein according to the present invention (partial peptide, including a salt), a DNA of the present invention, a antibody of the present invention and an antisense DNA of the present invention.

(2) Screening Method for a Compound Promoting or Inhibiting Expression of an Oncogenic Protein According to the Present Invention An oncogenic protein of the present invention, an oligonucleotide of the present invention, a transformant of the present invention or an antibody of the present invention can be used for a screening method for a compound promoting or inhibiting expression of a protein of the present invention.

Specifically, the present invention provides (i) a method for screening a compound promoting or inhibiting expression of an oncogenic protein of the present invention comprising determining and comparing the amount of expression of an oncogenic protein of the present invention or the amount of an mRNA encoding an oncogenic protein of the present invention when culturing a cell or tissue which can express an oncogenic protein of the present invention in the presence or absence of a test compound.

Examples of a cell or tissue which can express an oncogenic protein of the present invention include a human-derived cell, a warm-blooded animal (e.g., guinea pig, rat, mouse, poultry, rabbit, pig, sheep, bovine and monkey) cell (for example, neural cell, endocrine cell, neuroendocrine cell, glia cell, pancreatic β-cell, marrow cell, hepatic cell, splenic cell, mesangium cell, epidermal cell, epithelial cell, endothelial cell, fibroblast, fibrocyte, myocyte, adipocyte, immunocyte (e.g., macrophage, T-cell, B-cell, natural killer cell, mast cell, neutrophile, basophilic cell, acidophilic leucocyte, monocyte, dendritic cell), mega karyocyte, synoviocyte, cartilage cell, osteocyte, osteoblast, osteoclast, mammary glandular cell, interstitial cell and their precursor cells, stem cells and carcinoma cells, as well as all tissues where any of these cells is present such as brain, brain sites (for example, olfactory bulb, amygdaloid nucleus, basal cistern, hippocampus, optic thalamus, hypothalamus, cerebral cortex, medula oblongata, cerebellum), spinal cord, pituitary gland, stomach, pancreas, kidney, liver, genital gland, hyroid gland, gallbladder, bone marrow, adrenal gland, skin, muscle, lung, gastrointestinal tract (for example, large intestine and small intestine), blood vessel, heart, thymus gland, spleen, salivary gland, peripheral blood, prostate gland, testicle (spermary), ovary, placenta, uterus, bone, cartilage, joint and skeletal muscle. Here, an established cell or primary culture system may be used. In particular, it is desirable to use the above transformant cell of the present invention.

A method for culturing a cell which can express a protein of the present invention is as described for culturing the above transformant of the present invention.

A test compound may be, in addition to the above test compounds, a DNA library.

The amount of expression of a cancer cell of the present invention can be determined a known method such as an immunochemical method using, for example, an antibody, or alternatively an mRNA encoding an oncogenic protein of the present invention can be determined by a known method using Northern hybridization, RT-PCR or TaqMan PCR.

The amounts of expression of an mRNA can be compared by hybridization in accordance with a known method or its modification, for example, a method described in Molecular Cloning 2nd, J. Sambrook et al., Cold Spring Harbor Lab. Press, 1989.

Specifically, the amount of a mRNA encoding an oncogenic protein of the present invention is determined according to a known method, i.e., by contacting an RNA extracted from a cell with a polynucleotide of the present invention or its part or an antisense polynucleotide of the present invention and then measuring the amount of mRNA bound to a polynucleotide of the present invention or its part or an antisense polynucleotide of the present invention. A polynucleotide of the present invention or its part or an antisense polynucleotide of the present invention can be labeled with, for example, a radioisotope or dye to facilitate determination of the amount of mRNA bound to a polynucleotide of the present invention or its part or an antisense polynucleotide of the present invention. Examples of a radioisotope include $^{32}P$ and $^{3}H$, and examples of a dye include fluorochromes such as fluorescein, FAM (PE Biosystems Inc.), JOE (PE Biosystems Inc.), TAMRA (PE Biosystems Inc.), ROX (PE Biosystems Inc.), Cy5 (Amersham Inc.) and Cy3 (Amersham Inc.).

The amount of an mRNA can be determined by transforming an RNA extracted from a cell into cDNA using a reverse transcriptase and then measuring the amount of amplified cDNA by PCR using a polynucleotide of the present invention or its part or an antisense polynucleotide of the present invention as a primer.

Thus, a test compound which increases the amount of an mRNA encoding an oncogenic protein of the present invention can be selected as a compound promoting expression of an oncogenic protein of the present invention, while a test compound which reduce the amount of an mRNA encoding an oncogenic protein of the present invention can be selected a compound inhibiting expression of an oncogenic protein of the present invention.

The present invention also provides (ii) a method for screening a compound promoting or inhibiting promoter activity comprising determining and comparing a reporter activity when culturing, in the presence or absence of a test compound, a transformant obtained by transforming with a recombinant DNA in which a reporter gene is ligated to the downstream of a promoter or enhancer domain for a gene encoding an oncogenic protein of the present invention.

Examples of a reporter gene which can be used include lacZ (β-galactosidase gene), chloramphenicol acetyltransferase (CAT), luciferase, growth factors, β-glucuronidase, alkaline phosphatase, Green fluorescent protein (GFP) and β-lactamase.

By determining the amount of a reporter gene product (e.g., mRNA and protein) using a known method, a test compound which increases the amount of the reporter gene product can be selected as a compound controlling (particularly, promoting) promoter or enhancer activity of a protein of the present invention, i.e., as a compound promoting expression of a protein of the present invention. On the contrary, a test compound which reduces the amount of the reporter gene product can be selected as a compound controlling (particularly, inhibiting) promoter or enhancer activity of a protein of the present invention, i.e., as a compound inhibiting expression of a protein of the present invention.

A test compound may be as described above.

A vector comprising a reporter gene can be constructed or assayed by a known technique (For example, see Molecular Biotechnology 13, 29-43, 1999).

Since a compound inhibiting expression of an oncogenic protein of the present invention can inhibit biological activities of an oncogenic protein of the present invention, it is useful as a safe and low-toxic medical drug for inhibiting biological activities of an oncogenic protein of the present invention. Specifically, it is useful as a prophylactic or therapeutic drug for a cancer such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer, particularly cervical cancer.

A compound or its salt obtained using a screening method or screening kit of the present invention may be, for example, a compound selected from the group consisting of a peptide, a protein, a non-peptide compound, a synthetic compound, a fermentation product, a cell extract, a plant extract, an animal-tissue extract and plasma. A salt of the compound may be as described for a salt of a peptide derived from an oncogenic protein of the present invention.

When using a compound obtained using a screening method or screening kit according to the present invention as the above therapeutic or prophylactic agent, it can be used as usual. For example, as described for a medicine comprising a protein of the present invention, it can be prepared as a tablet, a capsule, an elixir, a microcapsule, a sterile solution and a suspension.

A dose of the compound or its salt depends on various factors such as its effect, a target disease, a recipient and a delivery route. For example, in oral administration of a compound inhibiting expression of a protein of the present invention for treating a cancer, its dose is about 0.1 to 100 mg, preferably about 1.0 to 50 mg, more preferably about 1.0 to 20 mg per day to a normal adult (weight: 60 kg). In parenteral administration, although a dose of the compound depends on various factors such as a recipient and a target disease, its dose is suitably about 0.01 to 30 mg, preferably about 0.1 to 20 mg, more preferably about 0.1 to 10 mg per day by intravenous injection when a compound inhibiting expression of a protein of the present invention is administered to a normal adult (weight: 60 kg) for treating a cancer. For another animal, an amount converted to a weight of 60 kg may be administered.

(3) Assay of an Oncogenic Protein of the Present Invention

An antibody of the present invention can specifically recognize an oncogenic protein of the present invention, so that it can be used for assaying the oncogenic protein of the present invention in a test solution, particularly an assay by sandwich immunity measuring method.

Thus, the present invention provides (i) a process for assaying an oncogenic protein of the present invention in a test solution comprising the steps of competitively reacting an antibody of the present invention with the test solution and a labeled protein of the present invention and then determining a proportion of the labeled protein of the present invention bound to the antibody; and (ii) a process for assaying an oncogenic protein of the present invention in a test solution comprising the steps of simultaneously or sequentially reacting the test solution with an antibody of the present invention insolubilized on a carrier and another labeled antibody of the present invention and then determining an activity of the labeling agent on the insolubilized carrier.

In the assay described in (ii), it is desirable that one antibody is an antibody recognizing the N-terminus in an oncogenic protein of the present invention, while the other antibody is an antibody reacting with the C-terminus in an oncogenic protein of the present invention.

A monoclonal antibody to an oncogenic protein of the present invention can be used for assaying an oncogenic protein of the present invention or detection using, for example, tissue staining. For these purposes, an antibody molecule itself can be used, or alternatively, an F(ab')$_2$, Fab' or Fab fraction of the antibody molecule can be used.

There are no particular restrictions to a procedure for assaying an oncogenic protein of the present invention using an antibody of the present invention, and it may be any procedure whereby the amount of an antibody, antigen or antibody-antigen complex corresponding to the amount of an antigen (for example, the amount of a peptide) in a measured solution can be detected by chemical or physical means and a desired value can be calculated using a standard curve plotted using the standard solution containing a known amount of the antigen. For example, nephelometry, a competition assay, an immunoradiometric assay and a sandwich assay are suitably used, and in terms of sensitivity and specificity, a sandwich assay described below is particularly preferable.

Examples of a labeling agent used in an assay using such a labeling material include a radioisotope, an enzyme, a fluorescent substance and a luminescent material. Examples of a radioisotope include [$^{125}$I], [$^{131}$I], [$^{3}$H] and [$^{14}$C]. Among these, a stable enzyme exhibiting a large specific activity is preferable, including β-galactosidase, β-glucuronidase, alkaline phosphatase, peroxidase and malate dehydrogenase. Examples of a fluorescent substance include fluorescamine and fluorescein isothiocyanate. Examples of a luminescent material include luminol, luminol derivatives, luciferin and lucigenin. A biotin-avidin system may be used for binding an antibody or antigen with a labeling agent.

An antigen or antibody can be insolubilized using physical adsorption, or using a chemical bond commonly used for insolubilizing or immobilizing a peptide or enzyme. Examples of a carrier include insoluble polysaccharides such as agarose, dextran and cellulose; synthetic resins such as polystyrene, polyacrylamide and silicones; and glasses.

In a sandwich assay, an insolubilized monoclonal antibody of the present invention is reacted with a test solution (first reaction), and then reacted with another labeled monoclonal antibody of the present invention (second reaction). Then, an activity of the labeling agent on the insolubilized carrier can be determined to assay the amount of a protein of the present invention in the test solution. The first and the second reactions may be conducted in the reverse order, simultaneously or sequentially. A labeling agent and an insolubilizing method may be as described above. In an immunity measuring method using a sandwich assay, it is not necessary to use only one antibody for a solid phase or for labeling, but a mixture of two or more antibodies may be used for, for instance, improving measurement sensitivity.

In determination of an oncogenic protein of the present invention by a sandwich assay according to the present invention, monoclonal antibodies of the present invention used in the first and the second reactions is preferably antibodies having a different site to which the oncogenic protein of the present invention is bound. Specifically, in terms of antibodies used in the first and the second reactions, when the antibody used in the second reaction recognizes the C-terminus in the oncogenic protein of the present invention, the antibody used in the first reaction is an antibody which recognizes a site other than the C-terminus, for example the N-terminus.

A monoclonal antibody of the present invention may be used a measurement system other than a sandwich assay, such as a competitive assay, immunometry and nephelometry.

In a competitive assay, an antigen in a test solution and a labeled antigen are competitively reacted with an antibody, the unreacted labeled antigen (F) is separated from the bound labeled antigen (B) (B/F separation) and the labeled amount of either B or F is determined to assay the antigen amount in the test solution. This reaction assay can be conducted by a liquid phase method where a soluble antibody is used as an antibody and polyethylene glycol and a secondary antibody to the above antibody are used in B/F separation, or alternatively by a solid phase method where a immobilized antibody is used as the first antibody or the first antibody is a soluble one and the second antibody is a immobilized antibody.

In immunometry, an antigen in a test solution and a immobilized antigen are competitively reacted with a given amount of a labeled antibody, the solid and the liquid phases are separated, or alternatively an antigen in a test solution is reacted with an excessive amount of a labeled antibody, a immobilized antigen is added to allow the unreacted labeled antibody to bind to the solid phase and then the solid and the liquid phases are separated. Then, the label amount in either phase is determined to assay the antigen amount in the test solution.

Nephelometry determines the amount of an insoluble precipitate resulting from an antigen-antibody reaction in a gel or solution. Even when the amount of an antigen in a test solution is small so that a small amount of precipitate is formed, laser nephelometry utilizing laser scattering is suitably used.

For applying the individual immunological measuring methods to an assay of the present invention, special conditions or operations are not necessary. A measuring system for a protein of the present invention may be constructed in the light of common conditions and operations in the individual methods with modifications known to the skilled in the art. Details in these common technical procedures will be found in various reviews and textbooks.

Such literatures may be, for example, "Radioimmunoassay", ed. by Hiroshi Irie, Kodansha, published in 1974; "Radioimmunoassay, 2$^{nd}$", ed. by Hiroshi Irie, Kodansha, published in 1979; "Enzyme Immunoassay", ed. by Eiji Ishikawa et al., Igaku-Shoin, published in 1978; "Enzyme Immunoassay, 2$^{nd}$ Edition", ed. by Eiji Ishikawa et al., Igaku-Shoin, published in 1982; "Enzyme Immunoassay, 3$^{rd}$ Edition", ed. by Eiji Ishikawa et al., Igaku-Shoin, published in 1987; "Methods in ENZYMOLOGY", Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); and ibid., Vol. 121 (Immunochemical Techniques (Part I: Hybridoma Technology and Monoclonal Antibodies)) (these have been published by Academic Press).

When reduction in a level of an oncogenic protein of the present invention is detected by assaying the level using an antibody of the present invention, for example, it leads to a diagnosis that the subject has a disease associated with insufficiency in the oncogenic protein of the present invention or will probably contract the disease in future.

When increase in a level of an oncogenic protein of the present invention is detected, for example, it leads to a diagnosis that the subject has a disease induced by over-expression of the oncogenic protein of the present invention, including cancers such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer (in particular, cervical cancer), or will probably contract the disease in future.

An antibody of the present invention may be used to detect an oncogenic protein of the present invention present in a sample such as a body fluid and a tissue. It can be also used for preparing an antibody column used for purification of an oncogenic protein of the present invention, detection of a protein of the present invention in each fraction during purification and analysis of behavior of a protein of the present invention in a test cell.

(4) Gene Diagnostic Agent

A polynucleotide or antisense polynucleotide of the present invention can be also, for example, used as a nucleic acid probe for detecting an abnormality (gene defect) in a DNA or mRNA encoding an oncogenic protein of the present invention mainly in a human. For example, it is useful as a gene diagnostic agent for injury, mutation or reduced expression in the DNA or the mRNA or over-expression of the mRNA.

The above gene diagnosis using a polynucleotide or antisense polynucleotide of the present invention can be conducted in accordance with, for example, known Northern hybridization or PCR-SSCP (See, Genomics, Vol. 5, pp. 874-879 (1989); Proceedings of the National Academy of Sciences of the United States of America, Vol. 86, pp. 2766-2770 (1989)).

For example, when reduction in expression of an mRNA is detected by Northern hybridization, it leads to a diagnosis that the subject has a disease associated with insufficiency of an oncogenic protein of the present invention or will probably contract the disease in future.

When over-expression of an mRNA is detected by Northern hybridization, for example, it leads to a diagnosis that the subject probably has a disease induced by over-expression of the oncogenic protein of the present invention, including cancers such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer (in particular, cervical cancer), or will probably contract the disease in future.

(5) Drug Containing an Antisense Polynucleotide

An antisense polynucleotide of the present invention which complementarily binds to a polynucleotide of the present invention (for example, DNA) and can inhibit expression of the polynucleotide (for example, DNA) is less toxic and can inhibit in vivo activity of the protein of the present invention or the polynucleotide of the present invention (for example, DNA). Thus, it is useful as a prophylactic or therapeutic agent for a disease induced by over-expression of the protein of the present invention, for example, a cancer such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer.

When using the antisense polynucleotide as the above prophylactic or therapeutic agent, the antisense polynucleotide can be formulated as described for the above polynucleotide of the present invention.

The formulation thus obtained is less toxic and can be orally or parenterally administered to a human or mammal (for example, rat, rabbit, sheep, pig, bovine, cat, dog and monkey).

The antisense polynucleotide can be administered as such or in combination with a physiologically acceptable carrier such as an adjuvant for promoting intake, using a gene gun or a catheter such as a hydrogel catheter.

A dose of the antisense polynucleotide varies depending on many factors such as a target disease, a recipient and a delivery route, and is, for example, about 0.1 to 100 mg per day to an adult (weight: 60 kg) when an antisense nucleotide of the present invention is locally administered to an organ (for example, liver, lung, heart and kidney) for treating a cancer.

Furthermore, the antisense polynucleotide can be used as a diagnostic nucleotide probe for determining the presence of an oncogene DNA of the present invention in a tissue or cell or its expression status.

The present invention also provides (i) a double strand RNA comprising a part of an RNA encoding a protein of the present invention or an RNA complementary thereto;

(ii) a drug comprising the double strand RNA;

when appropriate, (iii) a ribozyme comprising a part of an RNA encoding a protein of the present invention; and (iv) a drug comprising the ribozyme.

These double strand RNA (RNAi; RNA interference method) and the ribozyme can inhibit expression of a polynucleotide (for example, DNA) of the present invention as in the above antisense polynucleotide and can inhibit in vivo activities of an oncogenic protein or polynucleotide (for example, DNA) of the present invention. Thus, it is useful as a prophylactic or therapeutic agent for a disease induced by over-expression of the oncogenic protein of the present invention, for example, a cancer such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer, particularly cervical cancer.

The double strand RNA can be designed and produced on the basis of the sequence of the polynucleotide of the present invention in accordance with a known method (See, for example, Nature, Vol. 411, p. 494, 2001).

The ribozyme can be designed and produced on the basis of the polynucleotide of the present invention in accordance with a known method (See, for example, TRENDS in Molecular Medicine, Vol. 7, p. 221, 2001). For example, it can be produced by ligating a known ribozyme to a part of an RNA encoding a protein of the present invention. An example of the part of an RNA encoding a protein of the present invention is a part (RNA fragment) near a restriction site on the RNA of the present invention which can be digested by a known ribozyme.

When using the double strand RNA or the ribozyme as the above prophylactic or therapeutic agent, it can be formulated and administered as described for the antisense polynucleotide.

(6) Medical Drug Comprising an Antibody of the Present Invention

An antibody of the present invention capable of neutralizing cancerization activity of an oncogenic protein of the present invention can be used as a prophylactic or therapeutic drug for a disease induced by over-expression of the oncogenic protein of the present invention, for example, a cancer such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer, particularly cervical cancer.

The above prophylactic or therapeutic drug for the disease comprising the antibody of the present invention can be orally or parenterally administered to a human or mammal (for example, rat, rabbit, sheep, pig, bovine, cat, dog and monkey) as such, i.e., as a solution or as an appropriate dosage form of pharmaceutical composition. A dose may vary depending on various factors such as a recipient, a target disease, a symptom and a delivery route, and may be, for example, generally 0.01 to 20 mg/kg, preferably 0.1 to 10 mg/kg, more preferably 0.1 to 5 mg/kg of the antibody of the present invention for a dose, about once to five times a day, preferably one to three times a day. It can be suitably administered by intravenous injection. In another type of parenteral or oral administration, a dose similar to that described above may be employed. If a symptom is particularly severe, a dose may be further increased, depending on the symptom.

An antibody of the present invention can be administered as such or as an appropriate pharmaceutical composition. A pharmaceutical composition used for the above administration comprises the above antibody or its salt and a pharmacologically acceptable carrier, diluent or excipient. Such a composition is provided as a dosage form appropriate for oral or parenteral administration.

Specifically, examples of a composition for oral administration include solid and liquid dosage forms including tablet such as sugar-coated tablet and film-coated tablet), pill, granule, powder, capsule such as soft capsule, syrup, emulsion and suspension. Such a composition is prepared by a known process and comprises a carrier, diluent or excipient commonly used in the art of pharmacy. Examples of a carrier or excipient for tablet include lactose, starch, sucrose and magnesium stearate.

Examples of a composition for parenteral administration include an injection and a suppository. Examples of an injection include an intravenous injection, a subcutaneous injection, an intracutaneous injection, an intramuscular injection and an intravenous drip injection. Such an injection may be prepared by a known method; for example, by dissolving, suspending or emulsifying the above antibody or its salt in a sterile aqueous or oily liquid commonly used for an injection. Examples of an aqueous liquid for injection include saline and an isotonic solution containing glucose or other adjuvants, which may be combined with an appropriate solubilizing agent including alcohols such as ethanol; polyols such as propyleneglycol and polyethyleneglycol; nonionic surfactants such as polysorbate 80 and HCO-50 (polyoxyethylene (50 mol) adduct of hydrogenated castor oil). Examples of an oily liquid include sesame oil and soybean oil, which may be combined with a solubilizing agent such as benzyl benzoate and benzyl alcohol. An injection thus prepared is generally filled in an appropriate ampule. A suppository used for rectal administration is prepared by mixing the above antibody or its salt with a common suppository base.

The oral or parenteral pharmaceutical composition is conveniently prepared in a dosage form suitable for a dose of an active ingredient. Examples of such a unit dosage form include tablet, pill, capsule, injection (ampule) and suppository. Each unit dosage form preferably contains generally 5 to 500 mg of the above antibody. In particular, an injection contains 5 to 100 mg, while another dosage form contains 10 to 250 mg.

Each of the above compositions may contain other active ingredients as long as they result in undesirable interaction when being compounded with the antibody.

(7) DNA Transferred Animal

The present invention provides a non-human mammal, for example, a "knock-in" animal, having a DNA encoding a human-derived oncogenic protein of the present invention (hereinafter, referred to as "an oncogene DNA of the present invention") or its variant DNA.

Specifically, the present invention provides (1) a non-human mammal having a human-derived oncogene DNA of the present invention or its variant DNA ("knock-in" animal);

(2) the "knock-in" animal in which the non-human mammal is a rodent;

(3) the "knock-in" mouse or rat in which the rodent is mouse or rat; and (4) a recombinant vector comprising the human-derived oncogene DNA of the present invention or its variant DNA which can be expressed in the non-human mammal.

A non-human mammal having a human-derived oncogene DNA or its variant DNA of the present invention (hereinafter, referred to as "a DNA transferred animal of the present invention") can be produced by transferring a desired DNA to an unfertilized egg, a fertilized egg, a sperm or a germinal cell including their initial cells, preferably in an embryogenesis stage in development of the non-human mammal (further preferably, in a stage of a single cell or fertilized egg cell and generally up to the 8-cell phase) by an appropriate method such as a calcium phosphate method, an electrical pulse method, lipofection, aggregation, microinjection, a particle gun method and a DEAE-dextran. By the DNA transfer method, a desired foreign DNA of the present invention may be transferred to a somatic cell, living organ or tissue cell for using it in cell culture or tissue culture. Furthermore, the cell can be fused with the above germinal cell by a known cell-fusion process to produce a DNA transferred animal of the present invention.

Examples of a non-human mammal include bovine, pig, sheep, goat, rabbit, dog, cat, guinea pig, hamster, mouse and rat. Among these, preferred is a rodent, particularly mouse (for example, a pure line such as a C57BL/6 strain and a DBA2 strain, and a hybrid line such as a $B6C3F_1$ strain, a $BDF_1$ strain, a $B6D2F_1$ strain, a BALB/c strain ad an ICR strain) or rat (for example, Wistar and SD) because its ontogenesis and biological cycles are relatively shorter in the light of producing a disease animal model and it can be easily bred.

A "mammal" in terms of a recombinant vector which can be expressed in a mammal may be, in addition to the above non-human mammal, a human.

A variant DNA to an oncogene derived from a human of the present invention refers not to a DNA of a homologue to an oncogene of the present invention inherent in a non-human mammal, but an artificially mutated one.

A variant DNA of the present invention may be a human-derived oncogene DNA of the present invention whose original nucleotide sequence has been varied (for example, mutation) such as a DNA having addition of a base, deletion or substitution with another base, or an abnormal DNA.

An abnormal DNA refers to a DNA expressing a protein which is similar to a normal oncogenic protein of the present invention but has a different activity; for example, a DNA expressing a peptide in which an activity of a normal oncogenic protein of the present invention is inhibited.

For transferring an oncogene DNA of the present invention to a target non-human animal, it is generally advantageous to use the DNA as a DNA construct bound in the downstream of a promoter capable of expressing the DNA in the non-human animal cell. For example, when transferring a human-derived DNA of the present invention, a DNA construct (for example, a vector) to which a human-derived oncogene DNA of the present invention has been bound can be microinjected to a fertilized egg of a target non-human mammal, for example, a murine fertilized egg, in the downstream of any of various promoters capable of expressing a DNA derived from any of various non-human mammals exhibiting higher homology to the DNA of the present invention (for example, rabbit, dog, cat, guinea pig, hamster, rat and mouse), to produce a DNA transferred non-human mammal capable of highly expressing the oncogene DNA of the present invention.

Examples of an expression vector for an oncogenic protein of the present invention include a *E. coli* derived plasmid, a *Bacillus subtilis* derived plasmid, an yeast derived plasmid, a bacteriophage such as λ-phage, a retrovirus such as Moloney leukemia virus and a mammalian virus such as a vaccinia virus and a baculovirus, preferably a *E. coli* derived plasmid, a *Bacillus subtilis* derived plasmid and an yeast derived plasmid.

Examples of a promoter for regulating the DNA expression include (i) promoters for a DNA derived from a virus (for example, simian virus, cytomegalovirus, Moloney leukemia virus, JC virus, mammary tumor virus and poliovirus);

(ii) promoters derived from various mammals (for example, human, rabbit, dog, cat, guinea pig, hamster, rat and mouse); for example, a promoter for albumin, insulin II, uroplakin II, elastase, erythropoietin, endothelin, muscle cretine kinase, glial fibrillary acidic protein, glutathione S-transferase, platelet-derived growth factor β, keratin K1, K10 and K14, type I and II collagens, cyclic-AMP dependent protein kinase βI subunit, dystrophin, tartrate-resistant alkaline phosphatase, atrial sodium diuretic factor, endothelial receptor tyrosine kinase (generally, abbreviated as "Tie2"), sodium potassium adenosine triphosphatase (Na, K-ATPase), neurofilament light chain, metallothionine I and 10A, metalloproteinase-1 tissue inhibitor, MHC Class I antigen (H-2L), H-ras, renin, dopamin β-hydroxylase, thyroid peroxidase (TPO), peptide chain elongation factor 1α (EF-1α), β-actin, α- and β-myosin heavy chain, myosin light chain 1 and 2, myelin base protein, thyroglobulin, Thy-1, immunoglobulin, variable H-chain part (VNP), serum amyloid P component, myoglobin, troponin C, smooth muscle α-actin, preproenkephalin A and vasopressin. Among these, preferred are a cytomegalovirus promoter, a promoter of human peptide chain elongation factor 1α (EF-1α), a human and a poultry β-actin promoters capable of higher expression in an entire body.

The above vector preferably comprises a sequence which terminate transcription of a desired messenger RNA in a DNA transferred non-human mammal (generally, called "terminator"). For example, DNA sequences derived from bovine or various mammals can be used, preferably a simian virus SV40 terminator.

Furthermore, if desired, it may be possible to ligate a splicing signal for each DNA, an enhancer region or a part of a eukaryotic DNA intron in the 5'-upstream of the promoter region, between the promoter region and a translation region, or in the 3'-downstream of the translation region for higher expression of a desired oncogene DNA.

A translation region of a normal oncogenic protein of the present invention can be obtained using, as a starting material, a complementary DNA prepared as a whole or partial genome DNA from human-derived liver, kidney or thyroid gland cell, a fibroblast-derived DNA and various commercially available genome DNA libraries, or by a known process from an RNA derived from liver cell, kidney cell, thyroid gland cell or fibroblast. For producing an abnormal DNA induced by mutation, a translation region in the normal peptide obtained from the above cell or tissue can be mutated by a point mutation induction method to produce a mutant translation region.

The translation region can be produced as a DNA construct which can be expressed in a DNA transferred animal, by a common DNA engineering procedure in which it is ligated to the downstream of the promoter or if desired the upstream of a transcription termination site.

Transfer of a human-derived oncogene DNA of the present invention in a fertilized egg cell stage is conducted such that the DNA is carried in all of germinal and somatic cells in a target non-human mammal. Presence of the oncogene DNA of the present invention in germinal cells in a produced animal after DNA transfer means that all progenies of the produced animal will carry the oncogene DNA of the present invention in all of their germinal and somatic cells. Offsprings of this type of animal inheriting the oncogene DNA of the present invention carry the oncogene DNA of the present invention in all of their germinal and somatic cells.

A non-human mammal to which a human-derived oncogene DNA of the present invention has been transferred can be successively bred under common breeding circumstances as a mammal carrying the oncogene DNA, after confirming that the mammal stably carries the human-derived oncogene DNA after mating.

Transfer of a human-derived oncogene DNA of the present invention in a fertilized egg cell stage is conducted such that the DNA is carried in all of germinal and somatic cells in a target non-human mammal. Presence of the human-derived oncogene DNA of the present invention in germinal cells in a produced mammal after DNA transfer means that all offsprings of the produced mammal will successively carry the human-derived oncogene DNA of the present invention in all of their germinal and somatic cells. Offsprings of this type of animal inheriting the human-derived oncogene DNA of the present invention successively carry the human-derived oncogene DNA of the present invention in all of their germinal and somatic cells.

A homozygote animal having a transduced DNA in both of homologous chromosomes can be produced and the male and the female animals can be mated for successive breeding such that all offsprings successively carry the DNA.

In a non-human mammal having a human-derived oncogene DNA of the present invention, the normal DNA of the present invention is highly expressed, and an activity of the intrinsic normal DNA may be promoted, sometimes resulting in onset of hyperactivity of the protein of the present invention. Thus, it can be used as a model animal for the disease. For example, a normal DNA transferred animal of the present invention can be used to elucidate a mechanism of hyperactivity of the oncogenic protein of the present invention or of a disease associated with the oncogenic protein of the present invention and investigate a therapy for these diseases.

Furthermore, since a non-human mammal to which a human-derived oncogene DNA of the present invention has been transferred shows increase in the free protein of the present invention, it can be used for screening a therapeutic agent to a disease associated with the oncogenic protein of the present invention.

On the other hand, a non-human mammal having an abnormal DNA of the present invention can be successively bred under common breeding circumstances as an animal carrying the DNA, after confirming that the animal stably carries the transduced DNA after mating. Furthermore, a desired abnormal DNA can be incorporated into the above plasmid to be used as a starting material. A DNA construct with a promoter can be produced by a common DNA engineering procedure. Transfer of an abnormal DNA of the present invention in a fertilized egg cell stage is conducted such that the DNA is carried in all of germinal and somatic cells in a target mammal. Presence of the abnormal DNA of the present invention in germinal cells in a produced animal after DNA transfer means that all offsprings of the produced animal will carry the abnormal DNA of the present invention in all of their germinal and somatic cells. Offsprings of this type of animal inheriting the abnormal DNA of the present invention carry the abnormal DNA of the present invention in all of their germinal and somatic cells. A homozygote animal having a transduced DNA in both of homologous chromosomes can be produced and the male and the female animals can be mated for successive breeding such that all offsprings successively carry the DNA.

In a non-human mammal having an abnormal DNA of the present invention, the abnormal DNA of the present invention is highly expressed, and an activity of the intrinsic normal DNA may be inhibited, sometimes resulting in a deactivation type refractoriness of the protein of the present invention. Thus, it can be used as a model animal for the disease. For example, an abnormal DNA transferred animal of the present invention can be used to elucidate a mechanism of the deactivation type refractoriness of the oncogenic protein of the present invention and investigate a therapy for the disease.

As a specific application, an animal highly expressing the abnormal DNA of the present invention can be used as a model for elucidating inhibition of a normal peptide activity (dominant negative activity) by the abnormal peptide of the present invention in the deactivation type refractoriness of the protein of the present invention.

Furthermore, since a non-human mammal to which an abnormal DNA of the present invention has been transferred shows increase in the free oncogenic protein of the present invention, it can be used for screening a therapeutic agent to the oncogenic protein or its deactivation type refractoriness.

A DNA transferred animal of the present invention can be used for investigating a clinical symptom of a disease associated with an oncogenic protein of the present invention such as a deactivation type refractoriness of the protein of the present invention. Furthermore, the animal can give more specific pathologic observation in each organ in a disease model associated with the oncogenic protein of the present invention and can contribute to development of a new therapy and investigation and treatment of a secondary disease due to the above disease.

Each organ can be extracted from a DNA transferred animal of the present invention, chopped and treated with a protease such as trypsin to obtain a free DNA transferred cell. The cell can be then cultured and the cultured cell can be subjected to lineage study. Furthermore, it can be used for identifying a cell producing the oncogenic protein of the present invention and investigating association with apotosis, differentiation or growth or a signal transfer mechanism in them and abnormality in them. Thus, it can be an effective research subject for elucidating the oncogenic protein of the present invention and its activity.

Furthermore, in order to develop a therapeutic agent for a disease associated with an oncogenic protein of the present invention such as a deactivation type refractoriness of the protein of the present invention, a DNA transferred animal of the present invention can be used to provide an effective and speedy screening method for the therapeutic agent using the above test and assay processes.

A non-human mammal germinal stem cell in which a gene DNA homologue to an oncogene of the present invention is inactivated, is very useful for producing a non-human mammal model insufficiently expressing the oncogene DNA of the present invention. An on-human mammal insufficiently expressing a gene DNA homologue to the oncogene of the present invention does not have various biological activities which can be induced by the oncogenic protein of the present invention. It can be, therefore, used as a model for a disease caused by inactivation of biological activities of the oncogenic protein of the present invention. Thus, it can be useful for elucidating the cause of the disease and investigating a therapy therefor.

(8a) Method for Screening a Therapeutic or Prophylactic Compound to a Disease Caused by Deletion or Damage in an Oncogene DNA of the Present Invention A non-human mammal insufficiently expressing a DNA of the present invention can be used for screening a therapeutic or prophylactic compound to a disease caused by deletion or damage in the DNA of the present invention.

Thus, the present invention provides a method for screening a therapeutic or prophylactic compound or its salt to a disease caused by deletion or damage in a DNA of the present invention, comprising the steps of administering a test compound to a non-human mammal insufficiently expressing the DNA of the present invention and then observing and/or determining change in the animal.

A non-human mammal insufficiently expressing the DNA of the present invention used in the screening process may be as described above.

Examples of a test compound include a peptide, a protein, a non-peptide compound, a synthetic compound, a fermentation product, a cell extract, a plant extract, an animal tissue extract and plasma, which may be a novel or known compound.

(8b) Method for Screening a Compound Promoting or Inhibiting a Promoter Activity to an Oncogene DNA of the Present Invention The present invention provides a method for screening a compound or its salt promoting or inhibiting a promote activity to an oncogene DNA of the present invention, comprising the steps of administering a test compound to a non-human mammal insufficiently expressing the DNA of the present invention and then detecting expression of a reporter gene.

In the screening method, a non-human mammal insufficiently expressing the DNA of the present invention may be, among the non-human mammals insufficiently expressing the DNA of the present invention, an animal in which the DNA of the present invention is inactivated by transducing a reporter gene and the reporter gene can be expressed under the control of a promoter to the DNA of the present invention.

Examples of a test compound include a peptide, a protein, a non-peptide compound, a synthetic compound, a fermentation product, a cell extract, a plant extract, an animal tissue extract and plasma, which may be a novel or known compound.

A reporter gene which can be used may be as described above; suitably β-galactosidase gene (lacZ), soluble alkaline phosphatase gene and luciferase gene.

In the non-human mammal insufficiently expressing the DNA of the present invention in which the oncogene DNA of the present invention is replaced with the reporter gene, the reporter gene exists under the control of the promoter to the DNA of the present invention, so that a substance encoded by the reporter gene can be traced to detect an activity of the promoter.

For example, when a part of a DNA domain encoding an oncogenic protein of the present invention is substituted with an $E.\ coli$ derived β-galactosidase gene (lacZ), β-galactosidase is expressed in place of the oncogenic protein of the present invention in a tissue in which the oncogenic protein of the present invention is naturally to be expressed. Thus, for example, by staining with a reagent to be a substrate for β-galactosidase such as 5-bromo-4-chloro-3-indolyl-β-galactopyranoside (X-gal), an expression state of the oncogenic protein of the present invention in a living animal can be conveniently observed. Specifically, a mouse defective in a homologue protein to an oncogenic protein of the present invention or its tissue section is fixed by, for example, glutaraldehyde, washed with a phosphate-buffered saline (PBS) and reacted with a stain solution containing X-gal at room temperature or about 37° C. for about 30 min to 1 hour. The tissue preparation thus obtained is washed with a 1 mM EDTA/PBS solution to quench the β-galactosidase reaction and then a color can be observed. Alternatively, an mRNA encoding lacZ may be detected as usual.

A compound or its salt obtained using the above screening method is selected from the above test compounds, which can promote or inhibit a promoter activity to an oncogene DNA of the present invention.

The compound selected by the above screening method can form a salt, which may be a salt with a physiologically acceptable acid (for example, an inorganic acid) or base (for example, an organic base), preferably an acid-addition salt. Examples of such a salt include salts with an inorganic acid such as hydrochloric acid, phosphoric acid, hydrobromic acid and sulfuric acid, or with an organic acid such as acetic acid, formic acid, propionic acid, fumaric acid, maleic acid, succinic acid, tartaric acid, citric acid, malic acid, oxalic acid, benzoic acid, methanesulfonic acid and benzenesulfonic acid.

Since a compound or its salt promoting a promoter activity to an oncogene DNA of the present invention promotes the activity of the peptide, it is useful as, for example, a medical drug such as a prophylactic and a therapeutic agents for a disease associated with insufficiency of an oncogenic protein of the present invention.

On the other hand, a compound or its salt inhibiting a promoter activity to a DNA encoding an oncogenic protein of the present invention is useful as a safe and low-toxic medical drug inhibiting cancer-inducing activity of the oncogenic protein of the present invention, for example a prophylactic or therapeutic agent for a cancer such as pulmonary cancer, renal cancer, hepatic carcinoma, non-small cell pulmonary cancer, ovarian cancer, prostatic cancer, gastric cancer, bladder cancer, breast cancer, cervical cancer, colonical cancer, rectal cancer and pancreatic cancer.

A derivative of the compound selected by the above screening may be also used.

A drug comprising the compound or its salt selected by the screening method can be prepared in a dosage form suitable for delivery to a target cancerous tissue as in a drug comprising a known anticancer drug to a given cancer.

Since the formulation thus prepared is safe and low toxic, it can be administered to a human as a main subject or a mammal in which a similar pharmacological effect would be expected (for example, rat, mouse, guinea pig, rabbit, sheep, pig, bovine, horse, cat, dog and monkey).

A dose of the compound or its salt depends on various factors such as a target disease, a recipient and a delivery route. For example, in oral administration of a compound inhibiting a promoter activity to a DNA of the present invention for treating a cancer, its dose is about 0.1 to 100 mg, preferably about 1.0 to 50 mg, more preferably about 1.0 to 20 mg per day to a normal adult patient (weight: 60 kg). In parenteral administration, although a dose of the compound depends on various factors such as a recipient and a target disease, its dose is suitably about 0.01 to 30 mg, preferably about 0.1 to 20 mg, more preferably about 0.1 to 10 mg per day by intravenous injection when a compound inhibiting a promoter activity to a DNA of the present invention is administered to a normal adult patient (weight: 60 kg) for treating a cancer. For another animal, an amount converted to a weight of 60 kg may be administered.

Thus, a non-human mammal insufficiently expressing an oncogene DNA of the present invention is considerably useful for screening a compound or its salt promoting or inhibiting a promoter activity to the oncogene DNA of the present invention, and therefore, can significantly contribute to elucidating causes of a variety of diseases due to insufficient expression of the oncogene DNA of the present invention and developing prophylactic or therapeutic agents for the diseases.

Furthermore, using a DNA containing a promoter region for an oncogenic protein of the present invention, a gene encoding a given protein can be ligated to a downstream site, and the product can be injected in an animal egg cell to produce a so-called transgenic animal (an introgressant animal), so that a mechanism specifically causing in vivo expression of the oncogene while avoiding cancerization. Furthermore, a proper reporter gene can be ligated to the promoter region to establish a transformant cell strain expressing the gene, which can be used as an in vitro search system for a low molecular-weight compound specifically promoting or inhibiting an in vivo production ability of the oncogenic protein of the present invention itself.

When being used for prevention or treatment of a cancer, a compound or its salt regulating activity of an oncogenic protein of the present invention can be combined with another anticancer agent such as ifosfamide, UTF, adriamycin, peplomycin, cisplatin, cyclophosphamide, 5-FU, UFT, methotrexate, mitomycin C and mitoxantrone.

EXAMPLES

The present invention will be more specifically with reference to Examples, These examples are included in the most preferred embodiments of the present invention, but the present invention is not limited to these embodiments.

Example 1

Cloning and Sequencing of a cDNA Encoding a hWAPL from Human

PCR was conducted using a commercially available cDNA library, a human testicular cDNA kit (Marathon-Ready™ cDNA Kit; Clontech Inc.) as a template and using two primers:

```
primer 1                                   (SEQ ID NO: 8)
(sequence: TTGGATCCATGACATCCAGATTTGGGAAAACATACAGTA
GG); and primer 2                                   (SEQ ID NO: 9)
(sequence: TTGAATTCCTAGCAATGTTCCAAATATTCAATCACTCTA
GA).
```

In the PCR reaction, Advantage 2 polymerase mix (Clontech Inc.) kit was used and according to the instructions in the kit, amplification was conducted with a temperature cycle:

(1) 94° C. for 1 min;
(2) 5 cycles of 94° C. for 10 sec and 72° C. for 2 min; and
(3) 25 cycles of 96° C. for 10 sec and 70° C. for 2 min, and then followed by elongation reaction being carried out at 72° C. for 5 min. After the reaction, the product of PCR amplification thus obtained was cloned to a plasmid vector pGEM-T easy (PROMEGA) in accordance with the instructions for pGEM-T easy (PROMEGA). It was transduced to *E. coli* DH5 a (Invitrogen) and using an ampicillin resistance gene in the plasmid vector pGEM-T easy, clones carrying the plasmid were selected in an LB agar medium containing ampicillin.

The plasmid carried by each of the selected clones was sequenced to obtain the sequence of the novel cDNA (SEQ. ID. No. 2) cloned therein. A novel protein comprising an amino acid sequence (SEQ. ID. No. 1) deduced from an ORF in the nucleotide sequence of the cDNA was designated as a human WAPL (hWAPL). A transformant carrying the full-length cDNA of the hWAPL, which was cloned in the plasmid, was designated as *Escherichia coli* DH5 pGEMhWAPL.

Example 2

Expression of an hWAPL Gene in a Human Cancerous Tissue

Under the consent of patients subjected to surgical excision of a cancerous tissue in Tokyo Medical College Hospital, the samples of surgically excised cancerous tissues were provided. The samples of surgically excised cancerous tissues were examined for the presence of hWAPL gene expression and the expression amount thereof by Northern blotting and real-time PCR.

In the Northern blotting, an mRNA expressed from the hWAPL gene was identified from total RNAs prepared, using a DNA having a nucleotide sequence complementary to the portion of nucleic acid Nos. 2511 to 2813 in the full-length sequence of the hWAPL of SEQ. ID. No. 2, as a detection probe. On the other hand, in the real-time PCR, a cDNA of the hWAPL was amplified, using an amplification kit SYBR Green I (TaKaRa Co. Ltd.) and as PCR primers, a pair of primers:

```
                                              (SEQ ID NO: 5)
    5'-GAATTCATAGGCACAGCGCTGAACTGTGTG-3'
    and (SEQ ID NO: 6).
    5'-TTGAATTCCTAGCAATGTTCCAAATATTCA-3'.
```

Furthermore, human β-actin was used as an intrinsic standard. PCR primers used for amplification of cDNA of human β-actin were a commercially available pair of primers (Clontech) of:

```
    5'-GGGAAATCGTGCGTGACATTAAG-3'  (SEQ ID NO: 10)
    and

5'-TGTGTTGGCGTACAGGTCTTTG3'    (SEQ ID NO: 11).
```

The temperature cycle condition selected for the real-time PCR was as follows:
(a) 95° C. for 30 sec;
(b) 40 cycles of 95° C. for 3 sec and 68° C. for 30 sec; and then
(c) 87° C. for 6 sec.

For the thermal cycle in the PCR reaction, Smart Cycler System (TaKaRa Co. Ltd.) was used. The amount of the double strand cDNA was detected by means of a fluorescent label therein to determine the amount of amplification product.

Figure 5:
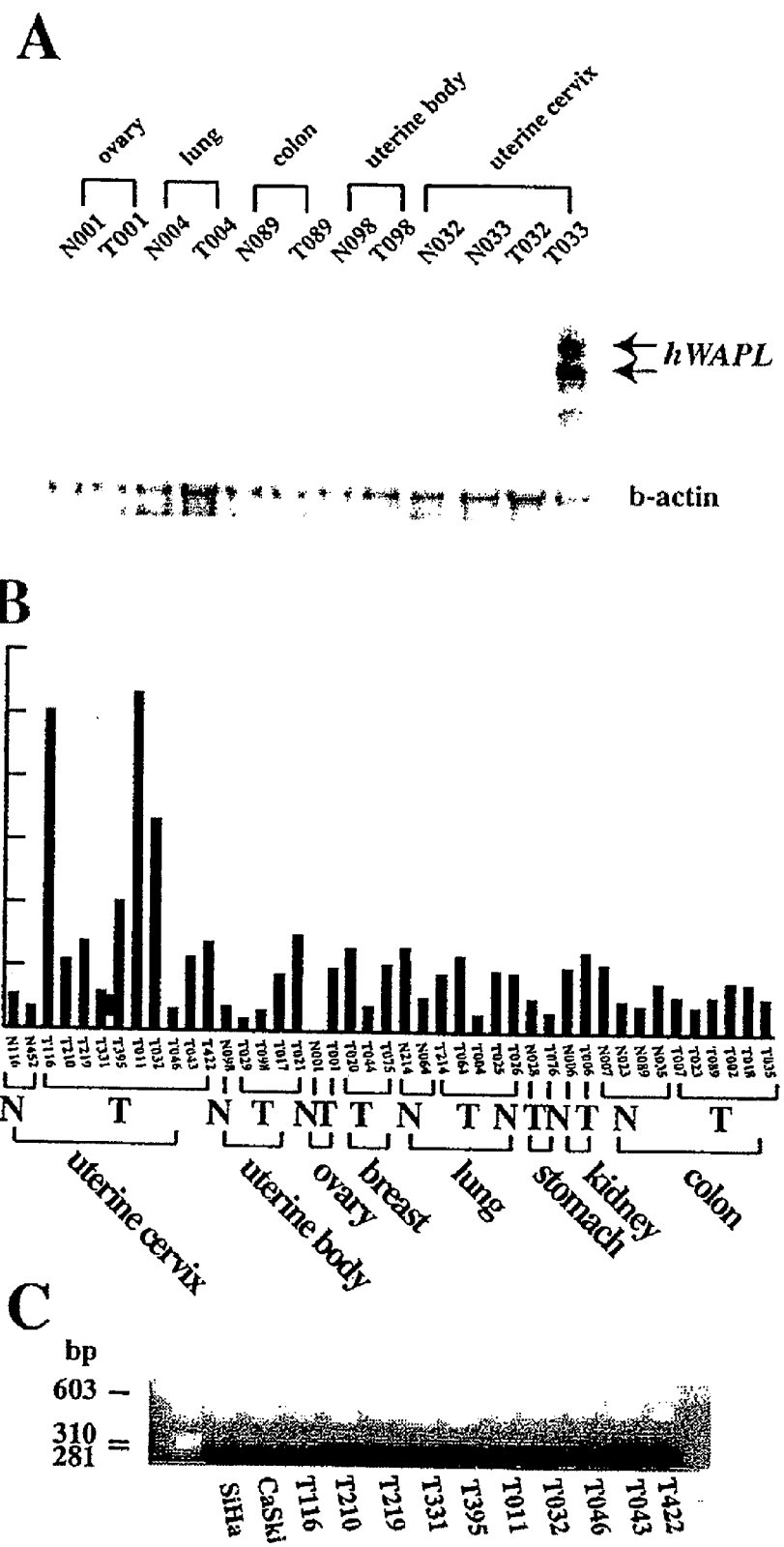
FIG. 5 shows (A): Northern blotting for evaluating an expression level of an hWAPL protein in carcinoma cells (T) of ovarian cancer, pulmonary cancer, colorectal carcinoma, corpus uteri cancer and cervical cancer in comparison with normal cells (N) corresponding thereto; (B): the results of real-time PCR for confirming expression of hWAPL gene in carcinoma cells (T) of cervical cancer, corpus uteri cancer, ovarian cancer, breast cancer, gastric cancer, renal cancer, colorectal carcinoma normal cells in comparison with (N) corresponding thereto; and (C): the results of RT-PCR detection of mRNA expression of E6/E7 gene derived from HPV in the carcinoma cells (T).

For the cancerous tissue samples mentioned above, comparative samples of total RNA were prepared from normal cells and carcinoma cells in the individual tissues in accordance with a known procedure (Oikawa et al., Cancer Res., 61, 5707-5709 (2001)). Among the carcinoma cells examined of cervical cancer, corpus uteri cancer, ovarian cancer, gastric cancer, renal cancer, pulmonary cancer, colorectal carcinoma and breast cancer, about 40% of carcinoma cell samples of cervical cancer demonstrated significant hWAPL gene expression (FIG. 5).

The carcinoma cell samples of cervical cancer were examined for the presence of HPV infection. Specifically, an mRNA region for the HPV-derived E6/E7 gene was detected by RT-PCR with corresponding primers therefor in accordance with a known procedure (Nakagawa et al., J. Med. Virol., 62, 251-258 (2000)), and in all the invasive carcinoma cell samples of cervical cancer, HPV infection and expression of the E6/E7 gene were confirmed. Exceptionally, some of gastric cancer samples also demonstrated high expression of the hWAPL gene.

Example 3

Induction of hWAPL Gene Expression by E6 and E7 from Hpv 16

An E6 gene from HPV 16 was amplified and isolated by RCR method using a pair of primers

```
16E6attB1:                            (SEQ ID NO: 12)
5'-AAAAAGCAGGCTCCACCATGTTTCAGGACCCACAGGAGCGACC
C-3', and 16E6attB2:(SEQ ID NO: 13)
5'-AGAAAGCTGGGTTACAGCTGGGTTTCTCTACGTG-3',
``` while an E7 gene from HPV 16 was amplified and isolated by RCR method using a pair of primers

```
    16E7attB1:                        (SEQ ID NO: 14)
    5'-AAAAAGCAGGCTCCACCATGCATGGAGATACACTACAT-3'
    and GE7attB2:                         (SEQ ID NO: 15)
    5'-AGAAAGCTGGGTTATGGTTTCTGAGAACAGATGGGG-3'.
```

Then, each of these genes were cloned into a retrovirus vector pCLXSN in accordance with a procedure of Naviaux et al. (Naviaux et al., J. Virol., 70, 5701-5705 (1996)), to generate retroviruses LXSN-16E6 and LXSN-16E7 for producing E6 and E7 recombinants, respectively. In addition, the retrovirus LXSN-16E6E7 for producing E6 and E7 recombinants simultaneously was produced.

It has been found that an product of E2 gene derived from HPV can be bound to a promoter region in the E6 and E7 genes to possess a function for inhibition of the transcription thereof, and that a product of E2 gene derived from a bovine papilloma virus (BPV) has a similar function for inhibiting the transcription. The BPV1 E2 gene fragment was obtained by nested PCR using pBPV-MII as a template. In the nested PCR, the pair of inner primers used was consisted of:

```
                                          (SEQ ID NO: 16)
    5'-AAAAAGCAGGCTCCACCATGGAGACAGCATGCGAAC-3'
    and (SEQ ID NO: 17)
    5'-AGAAAGCTGGGTCAGAAGTCCAAGCTGGCTGTAAAG-3',
``` while the pair of outer primers was consisted of:

```
                                        (SEQ ID NO: 18)
5'-GGGGACAAGTTTGTACAAAAAAGCAGGCT-3'
and

SEQ ID NO: 19)
5'-GGGGACAAGTTTGTACAAGAAAGCTGGGT-3'.
```

The BPV1 E2 gene fragment thus obtained was cloned into a retrovirus vector pCMSVpuro, which is based on a general-purpose virus vector pCMSCV (Clontech), to prepare a retrovirus MSCV-puro BPV1E2 for producing the E2 recombinant from BPV. The retrovirus vector pCMSVpuro comprises a puromycin resistance gene as a selection marker.

Human epidermal cells HDK1 (BioWhittaker) were infected with the retroviruses LXSN-16E6, LXSN-16E7 and LXSN-16E6E7 for producing HPV 16 derived E6 or E7 recombinants, respectively. As a negative control, a human epidermal cell HDK1 infected with a retrovirus vector pCLXSN was used. A cell line in which continued infection of the retrovirus vector was established was selected by culturing the cells on a medium containing G418 at 50 μg/mL for 3 days. After infection, expression of the hWAPL gene induced by a recombinant protein of the E6 or E7 from HPV 16 was determined by Western blotting using a specific antibody recognizing a region of partial amino acid sequence 50 to 66 (amino acid sequence: CNFKPDIQEIPKKPKVEE (SEQ ID NO: 20)) in the oncogenic protein hWAPL (FIG. 6).

At the same time, the amount of expression of p53 suppressor protein was also determined by Western blotting. Then, it was again confirmed that E6 product promoted a cleavage process of the p53 tumor suppressor protein, resulting in expression of the oncogenic protein hWAPL.

Furthermore, when the carcinoma cell lines of cervical cancer; CaSki, SiHa and C33A were infected with MSCV-puro BPV1E2, CaSki and SiHa cell lines producing E6 and E7 from HPV 16 demonstrated increase of the remained p53 tumor suppressor protein as a result of inhibiting transcription of E6 and E7 genes by the E2 from BPV. Concomitantly, expression of the oncogenic protein hWAPL was inhibited (FIG. 6). On the other hand, in the C33A cell line, in which cancerization was induced by mechanism other than such cancerization being originated by HPV infection, the amount of the remaining p53 tumor suppressor protein or the amount of expression of the oncogenic protein hWAPL was not affected. The results indicate that although the increased amount of expression of the oncogenic protein hWAPL is closely associated with cancerization, an independent mechanism causing increased expression of the oncogenic protein hWAPL may exist, which is different from the mechanism of increased expression of the oncogenic protein hWAPL due to E6 and E7 from HPV.

Example 4

Inhibition of Promoter Activity of the hWAPL Gene by a p53 Suppressor Protein

It was confirmed that the p53 suppressor protein has a function for inhibition of transcription of the hWAPL gene from its promoter, as follows.

A promoter of hWAPL gene was amplified and isolated by PCR method using a genomic DNA in DLD-1 cell as a template with use of a pair of primers:

```
primer 1
                                        (SEQ ID NO: 21)
(sequence: GTGCATCCCACCCACAGTGGAAGACATGG)
and primer 2
                                        (SEQ ID NO: 22)
(sequence: CCGCTTCCGCCGGTGAATGGTCAGTGCTGG).
```

A DNA fragment of the PCR product was first cloned to PGEMT-easy (PROMEGA), and sequentially, the fragment digested with a restriction enzyme EcoRI was then cloned to pBluescript (Stratagene). A region comprising a promoter portion of the hWAPL gene, which was inserted into the plasmid, was digested with SalI/XhoI and cloned into the pGL3-Basic vector (PROMEGA).

After purification with Qiagen Plasmid Maxi Kit (Qiagen), the vector obtained was co-transfected with a p53 expression vector, pHM6 (Roche) as for a control and a pGR3-tK vector for standardization of luciferase assay, using LipofectAmine-2000 (Invitrogen) in an HeLa cell. Dual Luciferase Kit (Promega) was used in the luciferase assay for determining the amount of labeled protein, luciferase, which was a reporter gene product transcribed and translated under control of the promoter of hWAPL gene.

As a result, it was confirmed that when transducing the p53 expression vector, increase in the amount of the expressed p53 suppressor protein reduced the amount of the labeled protein luciferase, which was transcribed and translated under control of the promoter of hWAPL gene, by 30% in comparison with the control. In other words, it is confirmed that the p53 suppressor protein has a function causing reduction in activity of the promoter of the hWAPL gene.

Example 5

Construction of an Expression Vector for Producing the hWAPL Recombinant Protein A HindIII and EcoRI restriction sites was transduced respectively at the ends of the region of base Nos. 1 to 3570 in the cDNA having the nucleotide sequence of SEQ. ID. No. 2 by site-specific mutagenesis using PCR. The PCR product thus obtained was digested with HindIII/EcoRI, and the corresponding DNA fragment was inserted into an HA-tagged mammalian expression vector, pHM6 (Roche Diagnostics) to construct an expression vector for producing a recombinant of the HA-tagged hWAPL protein, pHM6-hWAPL. The fragment was also inserted into an mammalian expression vector, phrGFP-N1 (Stratagene) for expressing a fused protein with an hrGFP fusion partner to construct an expression vector for producing a recombinant protein of a GFP fused hWAPL, phrGFP-hWAPL.

The expression vector for producing a recombinant was transfected to a host mammal cell using LipofectAmine 2000 (Invitrogen). After culturing for 2 days following the transfection, selection is conducted using EPICS ALYRA Hyper-Sort (Bechman Coulter) on the basis of the presence of expression of the hrGFP tag. After further culturing and additional selection, a transformed host cell line carrying the desired expression vector for producing the hWAPL recombinant protein.

Example 6

Generation of an Antibody Specific to the hWAPL Protein

For generating an antibody specific to the oncogenic protein hWAPL, a peptide chain (hWAPL$_{50-66}$) having a partial amino acid sequence 50 to 66: CNFKPDIQEIPKKPKVEE (SEQ ID NO: 20) that is located in the N-terminal region of the oncogenic protein hWAPL was prepared as an immunogen peptide by chemical synthesis. Furthermore, by recombination was produced a fused polypeptide tagged with 6×H His comprising a partial amino acid sequence 814-1037 lying in the C-terminal region of the oncogenic protein hWAPL.

According to conventional technique, these two immunogen peptides were used to separately immunize a rabbit to produce polyclonal antibodies specific to these antigen peptides, an anti-hWAPL-N antibody and an anti-hWAPL-C antibody. In Western blotting in Example 3 and so on, the oncogenic protein hWAPL was detected using the anti-hWAPL-N antibody specific to the hWAPL$_{50-66}$ antigen.

Example 7

Induction of Chromosome Instability by the hWAPL Protein

A HeLa cell is infected with the expression vector phrGFP-hWAPL for producing a recombinant protein of the hrGFP-fused hWAPL. The procedure described in Example 5 is conducted to select a GFP-hWAPL positive cell line producing the GFP-hWAPL-fused protein and a GFP-hWAPL negative cell line not producing the GFP-hWAPL-fused protein. After subculturing for five generations following the selection, the content of a chromosome gene DNA therein is assayed by Laser Scanning Cytomerty in accordance with Buse's procedure (J. Biol. Chem., 274, 7253-7263 (1999)).

The GFP-hWAPL negative cell line demonstrates a chromosome gene content equivalent to the host cell, HeLa cell, in which a half or more is comprised of a normal diploid and a content of a tetraploid is about a half of the diploid. On the other hand, in the GFP-hWAPL positive cell line, a normal diploid exists in a less amount, a major part demonstrates polyploidy, a content of a tetraploid is slightly more than that of a diploid, and an octoploid also exists at a content of 10.1%. Thus, it can be judged that over-expression of the hWAPL protein induces chromosome instability (FIG. 7).

Correspondingly, induction of nuclear atypia, in particular, of multi-nucleation is also originated from over-expression of the hWAPL protein. After three generation subculturing, ratios of observed multi-nucleation are only 5% and 4% in the GFP-hWAPL negative cell line and the HeLa cell infected with the phrGFP-N1 vector (control), respectively, while being 15.6% (three times or more) in the GFP-hWAPL positive cell line (FIG. 8).

Furthermore, in association with chromosomal abnormality such as nuclear atypia due to abnormal centromere division during a separation process by mitosis of a chromosome gene, induction of micronuclei formation is originated by over-expression of the hWAPL protein. A frequency of micronuclei formation in the GFP-hWAPL positive cell line is about two times as much as that in the GFP-hWAPL negative cell line (FIG. 7).

Example 8

Induction of Cancerization of an NIH 3T3 Fibroblast by the hWAPL Protein

An NIH 3T3 fibroblast is infected with the expression vector pHM6-hWAPL for producing a recombinant protein of the HA-tagged hWAPL to produce a recombinant cell line over-expressing the HA-tagged hWAPL protein, an HA-hWAPL 3T3 cell line. As a negative control, an HA-3T3 cell line infected with a pHM6 vector is produced. When culturing on a plate, the HA-3T3 cell line for negative control forms a homogenous confluent-like single cell layer as in the host cell, NIH 3T3 fibroblast, while the HA-hWAPL 3T3 cell line forms a focus structure.

To a nude mouse was subcutaneously injected the HA-hWAPL 3T3 cell line and the HA-3T3 cell line. Subsequent follow-up indicated that within 10 days, oncogenesis was induced in all the injection sites for the HA-hWAPL 3T3 cell line while no oncogenesis was induced in injection sites for the HA-3T3 cell line. By Western blotting using the anti-HA antibody and the anti-hWAPL-C antibody, it was confirmed that the HA-tagged hWAPL protein was actually over-expressed in the cancerized cell. In the cancerized cell, heterotypic mitosis was observed; for example, three pole division was also observed.

Example 9

Inhibition of Carcinoma Cell Growth by an siRNA Targeted to the hWAPL Gene

Using an siRNA targeted to the hWAPL gene, it was confirmed that inhibiting expression of the hWAPL protein can result in inhibition of growth of a carcinoma cell.

(1) In Vitro Inhibition of Carcinoma Cell Growth by an siRNA

Using the Silencer siRNA construction Kit (Ambion), siRNA were produced which are targeted to the following gene sequence (hWAPL AsiRNA) and to a control (negative control), respectively:

```
                                    (SEQ ID NO: 7)
    hWAPL AsiRNA:        CGGACTACCCTTAGCACAA (SEQ ID NO: 23)
    negative control:   ACTACAACTGGTCGCAACC.
```

Practically, two synthetic oligomers were prepared for each; specifically, for the hWAPL AsiRNA,

```
AACGGACTACCCTTAGCACAAcctgtctc       (SEQ ID NO: 24)
and

AATTGTGCTAAGGGTAGTCCGcctgtctc,      (SEQ ID NO: 25)
``` and, for the negative control,

```
AAACTACAACTGGTCGCAACCcctgtctc       (SEQ ID NO: 26)
and

AAGGTTGCGACCAGTTGTAGTcctgtctc.      (SEQ ID NO: 27)
```

Then, in each synthetic oligomer, a T7 promoter primer was hybridized at portion of ctgtctc and was treated with Klenow DNA polymerase to prepare completely a double strand DNA. Then, it was transcribed by T7 RNA polymerase, the RNAs of the antisense and sense chains prepared were hybridized each other, and then both cohesive ends were digested with Rnase to prepare a double strand siRNA with blunt ends.

To a SiHa cell derived from cervical cancer, in which hWAPL was highly expressing, was transduced the hWAPL AsiRNA and the negative control siRNA at a concentration of 1 nM for evaluating influence to cell growth.

Figure 10:
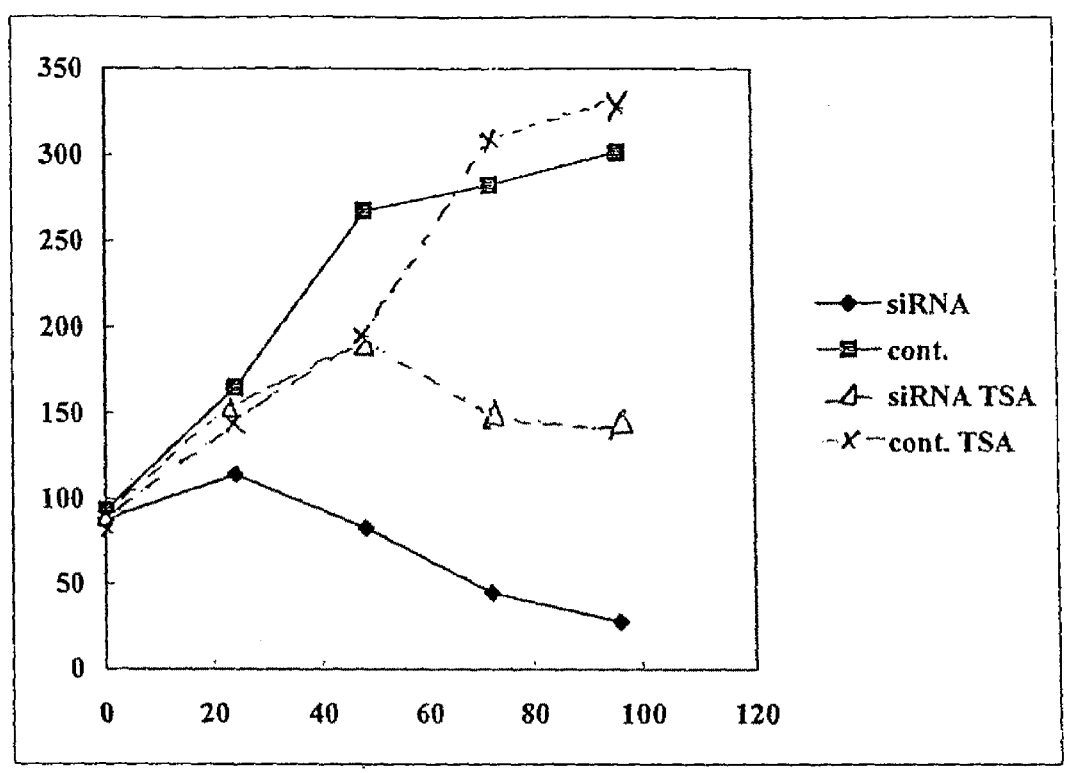
FIG. 10 shows the results of evaluating cell growth inhibiting effect by hWAPL siRNA in SiHa cell derived from HPV16 positive cervical cancer, displayed with a plot of the cell number ($\times 10^3$ in unit) (in ordinate) to a time from transduction of the siRNA (hour in unit) (in abscissa).

The siRNAs were transfected to the SiHa cell derived from an HPV16 positive cervical cancer, in which high expression of the hWAPL was observed. FIG. 10 shows the results of plotting the living cell number ($\times 10^3$) in the ordinate to a time from transduction of the siRNA (hour) in the abscissa. In the figure, "siRNA" for transfection of an siRNA targeting DIF-2, "cont" for transfection of a control siRNA, and "TSA" indicate the results obtained when adding a histone deacetylase inhibitor, Trichostatin A to a culture after transfection of the siRNA, respectively.

Until 20 hours after transfection of the hWAPL AsiRNA, increase in the living tumor cell number can be observed. During the period, comparison with the control may indicate inhibition of tumor growth. Subsequently, the cells to which the hWAPL AsiRNA was transduced show reduction in the living cell number and after 100 hours, a small number of cells were living. In contrast, when progress of deacetylation for acetylated lysines contained in a histon is inhibited by adding Trichostatin A, it attenuates effect of inhibition of cell growth by the hWAPL AsiRNA.

These results indicate that cell death by inhibition of an hWAPL is caused by inhibition of histon modification such as acetylation, and implies that the hWAPL itself may be involved in control of a histon code.

(2) In Vivo Inhibition Effect of Tumor Growth

To six-week old BALB3T3/nude mice were inoculated $2 \times 10^6$ of SiHa cells. From 10 days after inoculation, to the inoculated tumor cells were injected hWAPL AsiRNA and a negative control siRNA once two days and five times in total, respectively.

Variation of the inoculated tumor size was evaluated for 6 animals in the hWAPL AsiRNA injection group, 6 animals in the negative control siRNA injection group and 5 animals in the untreated group. The results indicated an average tumor size reduction of 33% in the hWAPL AsiRNA injection group in relation to the untreated group.

Furthermore, it was demonstrated that the nucleotide sequence of the cDNA for the hWAPL, which we cloned, was located in 10q23.31 to q23.32 on the human genome. The nucleotide sequence thereof is shown below, along with the nucleotide sequence of the 5'-untranslation region and promoter region in the elucidated hWAPL gene as well as the nucleotide sequence of cDNA for the above mouse WAPL. In the ORFs in the cDNAs, a region from the initiating codon ATG to the stop codon TAG is written by capitals, while in the promoter region, a region after a putative transcription initiating point is written by capitals on the basis of comparison with EST.

```
cDNA sequence of the hWAPL
                                        (SEQ ID NO: 28)
gcgagcggctgttggaggaaggaggtgggggccgggagcgcaaatggcgt tgagatggtycarggccctgttcaaactccagcactgaccattcaccggc ggaagcggcggcgcaggaggcggcggcggcccagcggggcacacagcag
```

```
                      -continued
gctctgttaccagctccagcagtggcggccagcgagagctaggcccgsgc ccggccggcggcgctcgaggcggggagggaagttgcggggccgccgctcc tgcccccccaaccgggcttcctatttaccgaaagcagagtccctcgcctc tctcggctctcacctgccggccctgctctcccgcgcgagggttccgcgcc cgcccgcgggccgtarggagcgggagaaggcggargcggccccgtggcca aagcacccgccaggcttccgaggagaatatgaaactggtgtcaaaATGAC

ATCCAGATTTGGGAAAACATACAGTAGGAAAGGTGGAAATGGCAGTTCAA

AATTCGATGAAGTCTTTTCCAACAAACGGACTACCCTTAGCACAAAATGG

GGAGAGACCACATTTATGGCTAAATTAGGGCAGAAGAGGCCCAATTTCAA

ACCAGATATCCAAGAAATTCCGAAGAAACCTAAAGTGGAAGAAGAAAGTA

CTGGAGATCCTTTTGGATTTGATAGTGATGATGAGTCTCTACCAGTTTCT

TCAAAGAATTTAGCCCAGGTTAAGTGTTCCTCTTATTCAGAATCTAGTGA

AGCTGCTCAGTTGGAAGAGGTCACTTCAGTACTTGAAGCTAATAGCAAAA

TTAGTCATGTGGTCGTTGAAGACACTGTCGTTTCTGATAAATGCTTCCCT

TTGGAGGACACTTTACTTGGGAAAGAAAAGAGCACAAACCGAATTGTAGA

AGATGATGCAAGCATAAGTAGCTGTAATAAATTAATAACTTCAGATAAAG

TGGAGAATTTTCATGAAGAACATGAAAAGAATAGTCACCATATTCACAAA

AATGCTGATGACAGTACTAAGAAACCCAATGCAGAAACTACAGTGGCTTC

TGAAATCAAGGAAACAAATGATACTTGGAACTCCCAGTTTGGGAAAAGGC

CAGAATCACCATCAGAAATATCTCCAATCAAGGGATCTGTTAGAACTGGT

TTGTTTGAATGGGATAATGATTTTGAAGATATCAGATCAGAAGACTGTAT

TTTAAGTTTGGATAGTGATCCCCTTTTGGAGATGAAGGATGACGATTTTA

AAAATCGATTGGAAAATCTGAATGAAGCCATTGAGGAAGATATTGTACAA

AGTGTTCTTAGGCCAACCAACTGTAGGACGTACTGTAGGGCCAATAAAAC

GAAATCCTCCCAAGGAGCATCAAATTTTGATAAGCTGATGGACGGCACCA

GTCAGGCCTTAGCCAAAGCAAACAGTGAATCGAGTAAAGATGGCCTGAAT

CAGGCAAAGAAAGGGGGTGTAAGTTGTGGGACCAGTTTTAGAGGGACAGT

TGGACGGACTAGAGATTACACTGTTTTACATCCATCTTGCTTGTCAGTTT

GTAATGTTACCATACAGGATACTATGGAACGCAGCATGGATGAGTTCACT

GCATCCACTCCTGCAGATTTGGGAGAAGCTGGTCGTCTCAGAAAAAAGGC

AGATATTGCAACTTCTAAGACTACTACTAGATTTCGACCTAGTAATACTA

AATCCAAAAAGGATGTTAAACTTGAATTTTTTGGTTTTGAAGATCATGAG

ACAGGAGGTGATGAAGGAGGTTCTGGAAGTTCTAATTACAAAATTAAGTA

TTTTGGCTTTGATGATCTCAGTGAAAGCGAAGATGATGAAGATGATGACT

GTCAAGTAGAAAGAAAGACAAGCAAAAAAAGAACTAAAACAGCTCCATCA

CCCTCCTTGCAGCCTCCCCCAGAAAGCAATGATAATTCCCAGGACAGTCA

GTCTGGTACTAACAATGCAGAAAACTTGGATTTTACAGAGGACTTGCCTG

GTGTGCCTGAAAGTGTGAAGAAGCCCATAAATAAACAAGGAGATAAATCA

AAGGAAATACCAGAAAGATTTTTAGTGGCCCCAAACGGTCACCCACAAA

AGCTGTATATAATGCCAGACATTGGAATCATCCAGATTCAGAAGAACTGC
```

-continued

```
CTGGGCCACCAGTAGTAAAACCTCAGAGTGTCACAGTGAGGCTGTCTTCA
AAGGAACCCAAATCAAAAAGATGATGGAGTTTTTAAGGCTCCTGCACCACC
ATCCAAAGTGATAAAAACTGTGACAATACCTACTCAGCCCTACCAAGATA
TAGTTACTGCACTGAAATGCAGACGAGAAGACAAAGAATTATATACTGTT
GTTCAGCACGTGAAGCACTTCAACGATGTTGTAGAATTTGGTGAAAATCA
AGAGTTCACTGATGACATTGAGTACTTGTTAAGTGGCTTAAAGAGCACTC
AGCCTCTAAACACACGTTGCCTTAGTGTTATTAGCTTGGCTACTAAATGT
GCCATGCCCAGTTTTCGAATGCACCTGAGAGCACATGGGATGGTAGCAAT
GGTCTTTAAAACCTTGGATGATTCCCAGCACCATCAGAATCTGTCCCTCT
GTACAGCTGCCCTCATGTATATACTGAGTAGAGATCGTTTGAACATGGAT
CTTGATAGAGCTAGCTTAGATCTAATGATTCGACTTTTGGAACTGGAACA
AGATGCTTCATCAGCCAAGCTACTGAATGAAAAGACATGAACAAAATTA
AAGAAAAAATCCGAAGGCTCTGTGAAACTGTACACAACAAGCATCTTGAT
CTAGAAAATATAACGACTGGGCATTTAGCTATGGAGACATTATTATCCCT
TACTTCTAAACGAGCAGGAGACTGGTTTAAAGAAGAACTCCGGCTTTTGG
GTGGTCTGGATCATATTGTAGATAAAGTAAAAGAATGTGTGGATCATTTA
AGTAGAGATGAGGATGAAGAGAAACTGGTAGCCTCACTATGGGGAGCAGA
GAGATGTTTACGAGTTTTAGAAAGTGTAACTGTGCATAATCCCGAAAATC
AAAGCTACTTGATAGCATATAAAGATTCCCAACTTATTGTTTCATCAGCT
AAAGCATTACAGCATTGTGAAGAACTGATTCAGCAGTACAACCGTGCTGA
GGACAGCATATGCTTAGCTGACAGTAAGCCTGTGCCTCACCAGAATGTAA
CTAACCATGTAGGCAAAGCAGTGGAGGACTGCATGAGGGCCATCATCGGG
GTGTTGCTTAATTTAACTAATGATAATGAGTGGGGCAGCACCAAAACAGG
AGAGCAGGACGGTCTCATAGGCACAGCGCTGAACTGTGTGCTTCAGGTTC
CAAAGTACCTACCTCAGGAGCAGAGATTTGATATTCGAGTGCTGGGCTTA
GGTCTGCTGATAAATCTAGTGGAGTATAGTGCTCGGAATCGGCACTGTCT
TGTCAACATGGAAACATCGTGCTCTTTTGATTCTTCCATCTGTAGTGGAG
AAGGGGATGATAGTTTAAGGATAGGTGGACAAGTTCATGCTGTCCAGGCT
TTAGTGCAGCTATTCCTTGAGCGAGAGCGGGCAGCCCAGCTAGCAGAAAG
TAAAACAGATGAGTTGATCAAAGATGCTCCCACCACTCAGCATGATAAGA
GTGGAGAGTGGCAAGAAACAAGTGGAGAAATACAGTGGGTGTCAACTGAA
AAGACTGATGGTACAGAAGAGAAACATAAGAAGGAGGAGGAGGATGAAGA
ACTTGACCTCAATAAAGCCCTTCAGCATGCCGGCAAACACATGGAGGATT
GCATTGTGGCCTCCTACACGGCACTACTTCTTGGGTGTCTCTGCCAGGAA
AGTCCAATCAATGTAACCACTGTGCGGGAATATCTGCCAGAAGGAGACTT
TTCAATAATGACAGAGATGCTCAAAAAATTTTTGAGTTTTATGAATCTCA
CTTGTGCTGTTGGAACAACTGGCCAGAAATCTATCTCTAGAGTGATTGAA
TATTTGGAACATTGCTAGctgctttacctttgcttcaggtgctcggtaat
gctggagctatccttagacaaagaaaagtcaagtcatgaagaagtcctt
gaagatataccaagaacattcatcagtatcattcgtgtttggatttttaa
```

-continued

```
ggccacctgatttcttcgtcatgcattcggcatttgctaaatgacagtta
ctacatcaatctgcaactatcaaaaatgaggggaaaaggttcaggctgtt
aacaattccatgcagtatttaaatacatttactttggcagagtttatacc
ctcccccttgttttcttgctttattctgggcaagtttgaaggggaaaattt
gtgctgctgttagtgcaactgctgtgtatgttgagccactgttgtcatgc
cagccaggtgcaaaggcagcttagctactgaggtagcgaatgttctgagg
acattctagacaacagcttagttcctttttcaggctcatttgcttttgct
ttttgttgaatgattccaatcgtaaataaagcttttaataattttgtga
atttttggttgttgttccctgaactactgtctatatttaaaattagatg
gaatccaaagatacacgggattaatagtatatttttttattcttgattag
gtttgggttattgaactattttttacttttgagaccacaaccatattcaa
tatcataccataatgtgtcatagctataggcacaagaaaaacaacagttt
gagagaatattatataagatgatgtgccctgttaaaggaggaggcaaaa
tagtcaaacccagggtagtttacacttaatgctagggaggctcttaaaac
attattagattttgaggaaagactctctagatatattttctaatgttcag
tacaataaaataaggaagctaaaacaccaatgtggaattcctgtttcca
gataacatgtatattcttctatagagtgacaggatcaattgcataagcgc
aaagccttaaaattgctggtttagagaagacccttttttcattcagattct
ttgttcgtagagcagttatttgaaaaacagttatggaacacaaaacattt
tatagatttaatatcataacattgcaaatttttcttgtattattgttcac
accactggtttatactttttttttttccttttttattgattgggcctgaata
caggcttctagagatcttttcattaatacttttaaatacctttcaggt
agttacatcatgtttcttcattggatttgtaaaacttgaagccataaaaa
tattagtttggtgtgtattggggaaaatagctaaaagtctaatttttacc
catttagactttgttatttccttgtataaagtgacaaatcggggctcttg
tatcagtgccagctgtaatgttttttaaatgcagtggctgccttctattgt
cttcctattttgataatgcagattgttgggaaatctgtaaggaagtaac
tgattccaggcaaattgttttcttccttctacccaccccaaccctaccc
atcaccttttaagaacatagtacgccagtgtaacgtgggaaccattgaga
ttgtatttgccctgagtattaaagctagcttagcaaaatacttttaaaa
catattggtaaatgatacccataaaattaaattagttatattttatttta
aaatgcaaaatacattgatatttattaatcattggatttaggggaaaggga
cagattttggtgaacctgacttgtggcagatggtaaggaatattataaa
acatttggatgagaacaatcagggcgaactgcattttttctgttacactgg
taatcatttgaaaattgatttacctcagtgttaacagtttttttgttttg
ttttgttttttaaataataactaattgtcgagcactgatagagatgcaga
ttttggtgggggggaggtggtggggagataatcacttcaccaactgcagt
gcatttgtgtgttttaaccctcagagaactctgcatttagggtacttg
aggctgacttaactaaaagttttaaagtaaccttttttccattgtaaata
tttctgtaaatactaccaattggaaattagaacagtagagtacttttctg
```

-continued aatccaatcctattttttattttatacagtatttctcagctgtgatctttg gagcaaaagccaacggcaggaaaaaatagtttgtaccagtttcatgaagt atgtctttgggttttttgtaaataattttaactcaaataaaattgctactt tcaatac Promoter region sequence of the hWAPLgene (SEQ ID NO: 29)

attttagtagagacgggtttcaccgtgttagccaggatggtctcgatc tcctgacctcatgatccgcctgcctcggcctctcaaagtgctaggattac aggcgtgagccaccgtgcctggccgctgaacacaatttaaagcttcaatt aatccaggtattcagtcaacaaatatttatagcacactttctgtgtgtga ggcactattctaggtgtgcttggcatataaaatgaacaaaagtcagccat cctcgtcctcatggagtttatattcttgtgaaacgaaatagataataaac aagttcatacacaaagcaaacgtaatgactatgttatggagaaaagcagc agggaaaaggagatacagggtgctggatgaccttaaatagcatggccaag gaaaacattactgagagacacacttgagcaaagacctgaaagcatgcagg gaatgagttgtgtgtgtctcttgaggactaacagagggaacaagtacgaa gagggcccacaggcaggagctggcttggcatgttctagtagtagacagag gcaggcccggcaaggtaggaagggataggagtactcaggggccagatcat gcagggccttttcaccgttaagaactttggattttagtattacaggagga cccttcagggtgtttgactaggcgggtatcatacagtattaagggtgagg atcctgaataaaaagggctgtttccaggacaagggtcaggaagccagac ttcttcgaggttgcttgtaccggtccttgtcaggcaatgtgctcctagag aatttcctttgctttgtgtttcatctacctagacagcagtgtattcccca gaggacgtcactatctccagagaacatattccaattatcctgggaaatat gataattgggattataacagtactcattttctcaattctcagaatgaaaa cctatccaaggcaagaacaaaagttctccagaaagcactcccctcccaat tgtgaaaacccagttaacatttttattagagctaccaggttatgtgaaact gttgatagttttatcactttcctttcaagatataggcaggggcagtggct catgcctgtaattccagcactttgggaggccaaggtaggtggatggcttg agcccagaagttcaagaccagcctgggcaacaaggtgaaaccctatctct accaaaaatacaaaaattagtggggcatgatagcatggacatgtagtccc agctacttgggaggctgaggtggaggatggcttgaaccctggaggtgga ggttgcagtgattggagatcgtgccactacattccagcctgggcgacaga gcaagactctgtcaccaaaaaaaaaaaaaaaaaaaaaaaaaaaatgtg gccaggcatggtagctcacacctgtaatcccagcactttgggaggctgag ccaggcggatcacaaggtcaagagatcgaaaccatcctggccaacatgca aaacaccatctctactaaaatacaaaaaatgagctgggtgtggtggtgtg cgcctgtagtcccagctactggggaggctgaggcaggggaatcgcttgaa ccaggggaggcagagattgcagtgagccgagatcgcgccactgcactccag cctggtgacagagcgagactccgtctaaaaaaaaaaaaaaaaaaaatatat atatatatatatataataatatgtatataattttacatgaaagaaggaaat aaatgggtgcttttattcaacaaatatttattgagcacctactcttgtgc caggcagtcttctaggtgctagggttgcagcagaaaacaagacaggcaga gatccctgccttcagagggagcacaacatttaagataaacatgcaaaatg cctgatatgttagatgggaagataaatgcccttaaagaaagtaaagcagg gacagtgacatttaggagtgaggatgttgcaacaatttaagataggttgg tcagggagattcattgaaaagtcccatctgagtgaaaacctagaggaga gaattgaagcaggctggtatctgggggagttgtaggcagagggaatagga aatacaaaggccctaaggtggggaaacagcaaggagtcaggtgtgggcag agcagaaagttggggctgcatgagcaaagggcagggcctggcccacatct cgtagagctttgtaatataaccacaacatgcaagtgtacaatttaacatt ttattccacatccgatggcaaagaaaaattgactgctaccaatatggtag tttctgacctgtagttccctaaatagaattctataagttgtaatacactt tactacacattatcagaaaaagactaaaagttctatttagtaactccaat tctgacagttctcatgtctgggctagaacaagggcatggcaatggcagaa cagatgtcttctattttctttgcaggattttctttttttcagaggaaagta caggtatgggcccactcaagtggagctccaggttagggggttctgtcctc acccaggcagcacacaggagggcagaggcccctcctaagggtactacaaa cttggctctgatccatgatttcagtttctgacaaacacaacattcagtgg gggaaagaaaatcaggtatctgagagcttgcacacaggcattctagcaaa accaaaagcacctactggctacttgatgttagtgtgaagattctcatgaa atggagacaaccattctaggggttgaggtggccaggggatggagcctga gctgagagaactaagaaaacaaaaacaatacaacaaaaagctgttcagcc atgtgttacccacactggagttctgtttgctcattctggtgtggaaccca gggccctggtaagggaatgaggggacttcagggcatttgcttgcctcagt ggaagcagggaggtaaggggttaaggtggtggtacagcctgcagggccag gagtctgaactccctccaggaggggcccgaggggtgtctttagtgtgagc cacacaagggtacagagcccagaagagctctgcttaatattcatatacta agcttccacagactaaatacacacacacacacacacacacacacacactc acacacactttacttctcaaatcatgtaccacttttctaccagattcaaga acaccaagaagtactaaagggtatccaaccgtcaagaaaaagtttgactc cctcattagttgtaacatacaagtcttcccattttccttacttgtaagata gagtaatggactgggaagcagacaaggcccctgaacagcctagcatctta cctgatgcataggaggttcttaatcatctcccttcctctccctcatccta acgaaaaatactagattgctgtcaaatgctatgggtatactttaaatcag tgcttgtcaaactttaatgtgcagcccaatcagctgggggaatcctgtta aaatgcaggttctgattcagtggagctggggtgagggataggaattatgc gttccttacaggcttccaggtgatgctacactgctgattggggatcattc tttgagtggcaagaatttgacactactaagtttcattacttaacacaacc -continued

```
atcacataaaagccctcaaaaggcaccagtctaaacaataagcccttcca
cttcagcctcatgcaggcactgaccctgccaagtgtccagcactagagag
gccaggcataatagacatatcctttggtcttgggaggatcacgacaccct
cctacaggaagatcttgcaattgtttcctcacctcttctggttttttgat
cttaccttttgcctctgatgataattacccttttaattaccacccaccacc
ttgtcatctaaataattatagtaagtgcagcctgcacctctgccagaaga
tctttaaacaaaatgataaaaacaagttcctaaactgccaattaaaaaaa
gagacaaaactgacccaaataaaacagtcatgtgcatcccacccacagtg
gaagacatggacttgttttcatataaactacagaagaagttgatttatt
ttgaaacaagaaaaagtactgattcagtatttaggaaattgtaaatgtca
gaatataaattctgcagtcaggtaggcaaaacaatccaaccacactaaaa
tccaccttaaattcctcttgggaagagctgcagggtctctgaactatttt
tcctttatttggagtttccccgattataccggagggagctggataacttc
tgggtgcattaaaagcaaattatccatttgtgggagaagggcggcttct
cactgaaagcaattagtagttttctaattcccaggtgggtctccattaa
ccgcctaacaaacaccaaggctgtcggagtccgacgaatcatgcacctct
cttaggggaactggttgcgctactctttagaacgctgttttcccatggt
agccttaaaaaaaacttaccaattttctgaattaggtaacacattgaatg
ggaaaaacctaagatagcacaaaaaggcgtacagcgaaaaattaagactc
cttcctcccgtcatccgccacctcactgtcctccctagaggcaatcgctg
gttcacttctttaaactttttattatggaaaatttcagatacacaagtaa
agagactgtatgatgagcacatatgctcgcatcacgcagcttcaacgatg
aaaaacgttctgccagcttgttttattcctctccccagttttcataggc
gtatttacagtcctgacaccagatcactctgtcaacacatcagtaggtc
ttaaaaaaaaaaaacaaaaaaccataaccacattaccgttaccacaccc
aacaaagttaatgataattgctcaataccatccaatattctcggggccac
tttcaatcggtgaggggcagacggacttagaggaaggactgcagggctgg
aggggcgcgaaaaagcgaggggcgacgctgctcgtggcctcgggtgtccg
gcgcctcgcggtccccgccatcgtcacctacgccgggccaggaccgacca
ggccaggtcgagggcggctcttgaccacgcgcccctgcctcccagctcc
cgggcggcggcctccgcaggcccggcacagctgcacagcccgcggtcccc
aggcaccggcgggtccctggaggggaagcgattgatacagctgcctgcac
tgcgccacccgcccggctgccatctccgtggcacctgcgtctcccggct
gggccgggagctagaagtggctgccgagaccgggagggcccggccagtcg
cccgctcccgctcccgcgcctggccctcggcccgcgacctcgcggacctg
gactacaactcccgtggggctccgacggccgggccaatggcgggcgccccg
gagcatgcggggcgcagcgcctgcgcggcggtttgagtaagcggctgcgc
gattggctgcgggtcgggcggccgcgcggggactgtgggaagcggagtg
acggaGCGAGCGGCTGTTGGAGGAAGGAGGTGGGGGCCGGGAGCGCAAAT
GGCGTTGAGATGGTTCAGGGCCCTGTTCAAACTCCAGCACTGACCATTCA
CCGGCGGAAGCG
``` cDNA sequence of the mouse WAPL (SEQ ID NO: 30)

```
ncggccgccagggaggcctaggccctgtccggccggcgcgcctgaggtgg
ggagggaagttgcggggccgccgctcaccccccaccccccctgtcgcccg
agcttcctatttaccgaagcggagccgcggactgtgacggcagcagagcc
cctcgcccctctcggtggcaccggtcggcactggtctctcgcgcggggct
cccgcgcccgcccgcgggccgttgggagccggagaggcggaggcggcccg
aggccaaagcacccgccaggcgccgagggaatatgaaacaggtgtcaaa
ATGACATCCAGATTTGGAAAAACTTACAGTAGGAAAGGAGGAAATGGCAG
TTCAAAATTTGATGAAGTTTTTTCCAACAAACGGACTACTCTTAGTACAA
AATGGGGTGAGACCACATTTATGGCTAAATTAGGGCAGAAGAGGCCCAAT
TTCAAACCAGATATTCAAGAAATTCCGAAGAAACCTAAAGTAGAAGAAGA
AGATACTGGAGATCCCTTTGGTTTTGATAGTGATGATGAGTCTCTACCTG
TTTCTTCAAAAAATTTAGCCCAGGGTAAGGGTTCATCTTACTCAGAATCT
AGTGAGGCTGCTCAGCTGGAAGAAGTCACTTCTGTATTTGAAGCTAATAG
CAAATGTAGTCATGTGGTGGGTGAAGACAGTTTTGCTTCCGACAGATGCT
TACTTGTGGAGGATACTTTAATTGGGAAAGAGAAGAGCATAaGTAGAATT
CCAGAAGACAACGCAAACAAAGTAGTTGCACTAAGTTGCTAACTTCAGA
TAAAGTGGAGAATTTTAGTGAAGAACATGAAAAAAATAGTCACCACTTTC
ACAAAAATGCTGAAGATAGTACTAAGAAACCCAATGCAGAAACCGCAGTG
GCTTCTGAATATAAAGCTGATGAAACTAAAGAAACAAATGATACTTGGAA
CTCCCAGTCTGGAAAAAGAACAGAGTCTCCATCTGAAAGTTGTCCAGTCA
AAGGATCTGTAAGAACTGGTTTATATGAATGGGATAATGATTTTGAAGAT
ATCAGGTCAGAAGACTGTATTTTAAGTTTGGATAATGAGTCTCTTTTGGA
GATGAAAGACGAGGATTTAAAAAATCGGATTGGAGGATTGGAAAATCTAA
ATGAAACCTTTGAAGAAGATATCATACAAAGTGTTCTTAGGCCAAGCAAC
TGTAGGACGTACTGTAGGGCCAATAAAGCGAGATCCTCACAGGGAGCATC
AAATTTTGATAAGCTAATGGATGGCACCAGTCAGTCCTTAGCCAAAGCAA
ACAGTGAATCAAGTAAAGATGGCCTGAATCAGGCAAAGAAAGGTAGTGCA
AGTTGTGGGACCAGTTTTCGAGGAACAGTTGGACGGACTAGAGATTACAC
TGTTTTACATCCATCTTGCTTGTCAGTGTGTAATGTTACCATCCAGGATA
CTATGGAACGGAGTATGGATGAGTTCACCGCATCCACTCCTGCAGATTTA
GGAGAGGCTGGCCGGCTCAGAAAAAAGGCAGATATTGCAACCTCCAAGAC
CACTACTAGATTTCGACCTAGTAATACTAAATCCAAAAAGGATGTTAAAC
TTGAATTTTTTGGTTTTGAAGATCATGATGAGACAGGAGGTGATGAAGGG
GGTTCTGGAAGTTCTAATTACAAAATTAAATATTTTGGCTTTGACGATCT
CAGCGAAAGTGAAGATCATGATCATGACCACTGTCAAGTGGAAAGAAAGA
AAGACAAAAAAGAACTAAAACAGCTCCATCACCTTCCCAGCAGCCTCCT
CCTGAAAGCAGCGACAATTCCCAGGATAGTCAGTCTAGTACTAATAATGC
```

-continued
```
AGAAAACTTGGATTTTACAGAGGACTTGCCTGGTGTGCCTGAGAGTGTGA

AGAAGCCCATAAGTAAACAAGGAGATAAATCCAAGGAAAATACCAGAAAG

ATTTTTAGTGGCCCCAAACGGTCACCTACAAAAGCTGTATATAATGCCAG

GCATTGGAACCATCCAGACTCGGAAGAATTGCCTGGACCACCAATAGCAA

AACCTCAGCGTGTCACAGTGAGGCTGTCTTCAAAGGAACCAAATCAAAAA

GATGATGGAGTTTTTAAGGCTCCTGCACCACCACTCAAAGTGATAAAAAC

TGTGACAATACCTACTCAGCCCTACCAAGAAATAGTTACTGCACTGAAAT

GCAGAAAAGAAGACAAAGAATTATATACGGTTGTTCAGCACGTGAAACAC

TTCAATGATGTGGTGGAATTTGGTGAAAATCAAGAGTTCACTGATGACAT

TGAATACTTGTTAAGTGGCTTAAAGAGTACTCAGCCTCTAAACACACGTT

GCCTTAGTGTTATCAGCTTAGCTACTAAATGTGCCATGCCCAGTTTTCGG

ATGCATCTGAGGGCACATGGGATGGTTGCAAtGGTCTTTAAAACTcTGGA

TGATTCCCAGCATCATCAGAATCTGTCCCTCTGTACAGCTGCTCTCATGT

ACATATTGAGTAGAGACCGtTTGAACATGGATCTTGATAGGGCCAGCCTA

GATCTCATGATTCGGCTTGTGGAGTTGGAACAAGATGCCTCTTCAGCTAA

GCTACTGAATGAAAAGACATGAACAAGATCAAAGAAAAGATCCGAACAC

TCTGTGAAACTGTGCACAACAAGCATCTTGATCTAGAAAACATAACGACT

GGTCATTTAGCTATGGAGACATTGCTGTCCCTCACTTCCAAACGAGCAGG

AGATTGGTTTAAAGAAGAGCTCCGACTTCTGGGTGGTCTGGATCATATTG

TAGATAAAGTAAAAGAGTGTGTGGATCATTTAAGTAGAGATGATGAGGAC

GAAGAGAAACTAGTAGCCTCATTATGGGGAGCAGAGAGATGTTTACGAGT

TTTAGAGAGTGTAACAGTGCATAATCCAGAGAATCAAAGCTACTTGATAG

CCTATAAAGATTCACAACTCATTATTTCATCAGCTAAAGCATTACAGCAT tGTGAAGACCTGAATCAGCAGTACAACCGTGCTGAGAACAGCATCTGTGT

AGCAGACAGTAACCCTCTGCCTTACCAGAATGTAACTAACCATGtgGGca

AAGCAGTGGAGGACTGCaTGAGGGCTATAATTGGAGTATTGCTCAATTTA

ACTAATGATAATGAGTGGGGCAGCACAAAGACAGGAGAACAAGAAGGACT

CATAGGCACAGCGATGAACTGTGTTCTTCAGGTTCCAAAGTACCTACCTC

AGGAGCAGAGATTTGATATTCGAGTGCTGGGATTGGGTCTACTCATAAAC

CTGGTGGAGTATAGTGcCCGGAATCGACACTGCCTTGTCAACATGCAAAC

ATCCTGTTCCTTTGATTCCTCCTTCTCTAGTGGAGAAGGCGATCATAGTT

TAAGGCTAGCCGGACAAGTTCATGCTGTTCAAGCTTTAGTGCAGCTATTT

CTCGAACGAGAGAGAGCAGCACAATTGGCAGAAAGTAAAACAGATGAATT

GATTAAAGATGCTCCTACCACTCAGCATGATAAGAGTGGAGAGTGGCAAG

AAACAAGTGGAGAAATACAGTGGGTATCAACTGAAAAGACTGATGGTGCA

GAGGAGAAGCAGAAGAAGGAGGAGGAGGATGAAGAACTTGACCTCAATAA

AGCCCTTCAGCATGCTGGCAAACACATGGAGGATTGCATCGTAGCCTCCT

ACACAGCCCTGCTTCTTGGGTGTCTCTGCCAGGAAAGTCCAATCAATGTA

ACTACAGTAAGGGAATATCTTCCAGAAGGAGATTTCTCCATAATGACAGA

GATGCTTAAAAAGTTCTTAAGCTTCATGAATCTTACGTGTGCTGTTGGAA
```

-continued
```
CAACAGGCCAGAAGTCTATCTCTAGAGTGATTGAATATTTGGAACATTGC

TAGctgctttacctttgcttcaggtgcttggtaatgctgaagctatcctt agacaaagaaaattggatttttatgatcaccgatttcttcatcatgcat tctgcgtttgctaaatgacagttactacatcaatctgcagctatcaaaaa tgagggaaaaggttcaggctgttaacaatcccatgcagtatttaaataca cttac
```

In the description and the drawings, when abbreviating nucleotides and/or amino acids, the abbreviations are those in accordance with IUPAC-IUB Commission on Biochemical Nomenclature or conventional abbreviations in the art. Examples are listed below. When optical isomers exist in an amino acid, an L-isomer is indicated unless specifically indicated.

DNA: deoxyribonucleic acid;
cDNA: complementary deoxyribonucleic acid;
A: adenine;
T: thymine;
G: guanine;
C: cytosine;
I: inosine;
R: adenine (A) or guanine (G);
Y: thymine (T) or cytosine (C);
M: adenine (A) or cytosine (C);
K: guanine (G) or thymine (T);
S: guanine (G) or cytosine (C);
W: adenine (A) or thymine (T);
B: guanine (G), guanine (G) or thymine (T);
D: adenine (A), guanine (G) or thymine (T);
V: adenine (A), guanine (G) or cytosine (C);
N: adenine (A), guanine (G), cytosine (C) or thymine (T) or unknown or another base;
RNA: ribonucleic acid;
mRNA: messenger ribonucleic acid;
dATP: deoxyadenosine triphosphate;
dTTP: deoxythymidine triphosphate;
dGTP: deoxyguanosine triphosphate;
dCTP: deoxycytidine triphosphate;
ATP: adenosine triphosphate;
EDTA: ethylenediaminetetraacetic acid;
SDS: sodium dodecyl sulfate;
BHA: benzhydrylamine;
pMBHA: p-methylbenzhydrylamine;
Tos: p-toluenesulfonyl;
Bzl: benzyl;
Bom: benzyloxymethyl;
Boc: t-butyloxycarbonyl;
DCM: dichloromethane;
HOBt: 1-hydroxybenzotriazole;
DCC: N,N'-dicyclohexylcarbodiimide;
TFA: trifluoroacetic acid;
DIEA: diisopropylethylamine;
Gly or G: glycine;
Ala or A: alanine;
Val or V: valine;
Leu or L: leucine;
Ile or I: isoleucine;
Ser or S: serine;
Thr or T: threonine;

Cys or C: cysteine;
Met or M: methionine;
Glu or E: glutamic acid;
Asp or D: aspartic acid;
Lys or K: lysine;
Arg or R: arginine;
H is or H: histidine;
Phe or F: phenylalanine;
Tyr or Y: tyrosine;
Trp or W: tryptophan;
Pro or P: proline;
Asn or N: asparagine;
Gln or Q: glutamine;
pGlu: pyroglutamic acid;
Tyr(I): 3-iodotyrosine;
DMF: N,N-dimethylformamide;
Fmoc: N-9-fluorenylmethoxycarbonyl;
Trt: trityl;
Pbf: 2,2,4,6,7-pentamethyldihydrobenzofuran-5-sulfonyl;
Clt: 2-chlorotrityl;
Bu$^t$: t-butyl; and
Met(O): methionine sulfoxide.

INDUSTRIAL APPLICABILITY

The full-length nucleotide sequence of an hWAPL oncogene according to the present invention allows for producing a recombinant of an hWAPL oncogenic protein encoded by the hWAPL oncogene, and investigating a cancerization mechanism induced by over-expression of the hWAPL oncogenic protein in a cell strain derived from any of various epithelial cells. Furthermore, in the present invention, a promoter region in the identified hWAPL oncogene may provide a new target in studying cancer prevention or therapy on the basis of a mechanism of inhibition of the cancerization mechanism induced by over-expression of the nWAPL oncogene, by inhibiting transcription of the oncogene. Furthermore, production of a recombinant of the full-length nucleotide sequence of the hWAPL oncogene according to the present invention, the hWAPL oncogenic protein, allows for preparation of a nucleic acid probe or PCR primer for detecting mRNA expression by transcription of the hWAPL oncogene or a specific antibody for detecting a translated hWAPL oncogenic protein peptide. Thus, it allows for using various diagnosis kits which detect over-expression of the hWAPL oncogene directly involved in onset of a cancer.

The invention claimed is:

1. A double stranded short-chain interfering RNA (siRNA) capable of inhibiting expression of a target mRNA in a cervical cancer cell, wherein the nucleotide sequence of one strand of the siRNA is the nucleotide sequence CGGACUAC-CCUUAGCACAA (SEQ ID NO: 31).

2. A pharmaceutical composition for inhibiting expression of a target mRNA in a cervical cancer cell to arrest growth of said cell, comprising the siRNA of claim 1.

* * * * *

UNITED STATES PATENT AND TRADEMARK OFFICE
CERTIFICATE OF CORRECTION

PATENT NO. : 7,893,246 B2
APPLICATION NO. : 12/207298
DATED : February 22, 2011
INVENTOR(S) : Akira Saito and Masahiko Kuroda It is certified that error appears in the above-identified patent and that said Letters Patent is hereby corrected as shown below:

In the Specifications:

Column 12, Line 60: delete ""Neo"," and insert -- "Neor", --
Column 13, Line 47: delete "army worm" and insert -- armyworm --
Column 13, Line 62: after "to" insert -- as --
Column 14, Line 66: delete "medium[the" and insert -- medium [the --
Column 19, Line 4: delete "a" and insert -- an --
Column 27, Line 29: delete "10A," and insert -- IIA, --
Column 29, Line 64: delete "An on-human" and insert -- A non-human --
Column 34, Line 23: delete "Hpv 16" and insert -- HPV 16 --
Column 34, Line 40: delete
" 5'-AAAAAGCAGGCTCCACCATGCATGGAGATACACTACAT-3'" and insert
-- 5'-AAAAAGCAGGCTCCACCATGCATGGAGATACACCTACAT-3' --

Column 34, Line 43: delete " GE7attB2:" and insert -- 16E7attB2: --

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 31

<210> SEQ ID NO 1
<211> LENGTH: 1190
<212> TYPE: PRT
<213> ORGANISM: Homo sapiens

<400> SEQUENCE: 1

```
Met Thr Ser Arg Phe Gly Lys Thr Tyr Ser Arg Lys Gly Gly Asn Gly
1               5                   10                  15

Ser Ser Lys Phe Asp Glu Val Phe Ser Asn Lys Arg Thr Thr Leu Ser
            20                  25                  30

Thr Lys Trp Gly Glu Thr Thr Phe Met Ala Lys Leu Gly Gln Lys Arg
        35                  40                  45

Pro Asn Phe Lys Pro Asp Ile Gln Glu Ile Pro Lys Lys Pro Lys Val
    50                  55                  60

Glu Glu Glu Ser Thr Gly Asp Pro Phe Gly Phe Asp Ser Asp Asp Glu
65                  70                  75                  80

Ser Leu Pro Val Ser Ser Lys Asn Leu Ala Gln Val Lys Cys Ser Ser
            85                  90                  95

Tyr Ser Glu Ser Ser Glu Ala Ala Gln Leu Glu Glu Val Thr Ser Val
            100                 105                 110

Leu Glu Ala Asn Ser Lys Ile Ser His Val Val Val Glu Asp Thr Val
        115                 120                 125

Val Ser Asp Lys Cys Phe Pro Leu Glu Asp Thr Leu Leu Gly Lys Glu
130                 135                 140

Lys Ser Thr Asn Arg Ile Val Glu Asp Ala Ser Ile Ser Ser Cys
145                 150                 155                 160

Asn Lys Leu Ile Thr Ser Asp Lys Val Glu Asn Phe His Glu Glu His
                165                 170                 175

Glu Lys Asn Ser His His Ile His Lys Asn Ala Asp Asp Ser Thr Lys
            180                 185                 190
```

-continued

```
Lys Pro Asn Ala Glu Thr Thr Val Ala Ser Glu Ile Lys Glu Thr Asn
        195                 200                 205

Asp Thr Trp Asn Ser Gln Phe Gly Lys Arg Pro Glu Ser Pro Ser Glu
210                 215                 220

Ile Ser Pro Ile Lys Gly Ser Val Arg Thr Gly Leu Phe Glu Trp Asp
225                 230                 235                 240

Asn Asp Phe Glu Asp Ile Arg Ser Glu Asp Cys Ile Leu Ser Leu Asp
                245                 250                 255

Ser Asp Pro Leu Leu Glu Met Lys Asp Asp Phe Lys Asn Arg Leu
                260                 265                 270

Glu Asn Leu Asn Glu Ala Ile Glu Glu Asp Ile Val Gln Ser Val Leu
            275                 280                 285

Arg Pro Thr Asn Cys Arg Thr Tyr Cys Arg Ala Asn Lys Thr Lys Ser
        290                 295                 300

Ser Gln Gly Ala Ser Asn Phe Asp Lys Leu Met Asp Gly Thr Ser Gln
305                 310                 315                 320

Ala Leu Ala Lys Ala Asn Ser Glu Ser Ser Lys Asp Gly Leu Asn Gln
                325                 330                 335

Ala Lys Lys Gly Gly Val Ser Cys Gly Thr Ser Phe Arg Gly Thr Val
                340                 345                 350

Gly Arg Thr Arg Asp Tyr Thr Val Leu His Pro Ser Cys Leu Ser Val
            355                 360                 365

Cys Asn Val Thr Ile Gln Asp Thr Met Glu Arg Ser Met Asp Glu Phe
        370                 375                 380

Thr Ala Ser Thr Pro Ala Asp Leu Gly Glu Ala Gly Arg Leu Arg Lys
385                 390                 395                 400

Lys Ala Asp Ile Ala Thr Ser Lys Thr Thr Arg Phe Arg Pro Ser
                405                 410                 415

Asn Thr Lys Ser Lys Lys Asp Val Lys Leu Glu Phe Phe Gly Phe Glu
            420                 425                 430

Asp His Glu Thr Gly Gly Asp Glu Gly Gly Ser Gly Ser Ser Asn Tyr
        435                 440                 445

Lys Ile Lys Tyr Phe Gly Phe Asp Asp Leu Ser Glu Ser Glu Asp Asp
        450                 455                 460

Glu Asp Asp Asp Cys Gln Val Glu Arg Lys Thr Ser Lys Lys Arg Thr
465                 470                 475                 480

Lys Thr Ala Pro Ser Pro Ser Leu Gln Pro Pro Glu Ser Asn Asp
                485                 490                 495

Asn Ser Gln Asp Ser Gln Ser Gly Thr Asn Asn Ala Glu Asn Leu Asp
                500                 505                 510

Phe Thr Glu Asp Leu Pro Gly Val Pro Glu Ser Val Lys Lys Pro Ile
            515                 520                 525

Asn Lys Gln Gly Asp Lys Ser Lys Glu Asn Thr Arg Lys Ile Phe Ser
        530                 535                 540

Gly Pro Lys Arg Ser Pro Thr Lys Ala Val Tyr Asn Ala Arg His Trp
545                 550                 555                 560

Asn His Pro Asp Ser Glu Glu Leu Pro Gly Pro Val Val Lys Pro
                565                 570                 575

Gln Ser Val Thr Val Arg Leu Ser Ser Lys Glu Pro Asn Gln Lys Asp
            580                 585                 590

Asp Gly Val Phe Lys Ala Pro Ala Pro Pro Ser Lys Val Ile Lys Thr
            595                 600                 605
```

-continued

```
Val Thr Ile Pro Thr Gln Pro Tyr Gln Asp Ile Val Thr Ala Leu Lys
    610                 615                 620

Cys Arg Arg Glu Asp Lys Glu Leu Tyr Thr Val Val Gln His Val Lys
625                 630                 635                 640

His Phe Asn Asp Val Val Glu Phe Gly Glu Asn Gln Glu Phe Thr Asp
                    645                 650                 655

Asp Ile Glu Tyr Leu Leu Ser Gly Leu Lys Ser Thr Gln Pro Leu Asn
                660                 665                 670

Thr Arg Cys Leu Ser Val Ile Ser Leu Ala Thr Lys Cys Ala Met Pro
            675                 680                 685

Ser Phe Arg Met His Leu Arg Ala His Gly Met Val Ala Met Val Phe
    690                 695                 700

Lys Thr Leu Asp Asp Ser Gln His His Gln Asn Leu Ser Leu Cys Thr
705                 710                 715                 720

Ala Ala Leu Met Tyr Ile Leu Ser Arg Asp Arg Leu Asn Met Asp Leu
                    725                 730                 735

Asp Arg Ala Ser Leu Asp Leu Met Ile Arg Leu Leu Glu Leu Glu Gln
                740                 745                 750

Asp Ala Ser Ser Ala Lys Leu Leu Asn Glu Lys Asp Met Asn Lys Ile
            755                 760                 765

Lys Glu Lys Ile Arg Arg Leu Cys Glu Thr Val His Asn Lys His Leu
    770                 775                 780

Asp Leu Glu Asn Ile Thr Thr Gly His Leu Ala Met Glu Thr Leu Leu
785                 790                 795                 800

Ser Leu Thr Ser Lys Arg Ala Gly Asp Trp Phe Lys Glu Glu Leu Arg
                    805                 810                 815

Leu Leu Gly Gly Leu Asp His Ile Val Asp Lys Val Lys Glu Cys Val
                820                 825                 830

Asp His Leu Ser Arg Asp Glu Asp Glu Lys Leu Val Ala Ser Leu
            835                 840                 845

Trp Gly Ala Glu Arg Cys Leu Arg Val Leu Glu Ser Val Thr Val His
    850                 855                 860

Asn Pro Glu Asn Gln Ser Tyr Leu Ile Ala Tyr Lys Asp Ser Gln Leu
865                 870                 875                 880

Ile Val Ser Ser Ala Lys Ala Leu Gln His Cys Glu Glu Leu Ile Gln
                    885                 890                 895

Gln Tyr Asn Arg Ala Glu Asp Ser Ile Cys Leu Ala Asp Ser Lys Pro
                900                 905                 910

Leu Pro His Gln Asn Val Thr Asn His Val Gly Lys Ala Val Glu Asp
            915                 920                 925

Cys Met Arg Ala Ile Ile Gly Val Leu Leu Asn Leu Thr Asn Asp Asn
    930                 935                 940

Glu Trp Gly Ser Thr Lys Thr Gly Glu Gln Asp Gly Leu Ile Gly Thr
945                 950                 955                 960

Ala Leu Asn Cys Val Leu Gln Val Pro Lys Tyr Leu Pro Gln Glu Gln
                    965                 970                 975

Arg Phe Asp Ile Arg Val Leu Gly Leu Gly Leu Ile Asn Leu Val
                980                 985                 990

Glu Tyr Ser Ala Arg Asn Arg His Cys Leu Val Asn Met Glu Thr Ser
            995                 1000                1005

Cys Ser  Phe Asp Ser Ser Ile  Cys Ser Gly Glu Gly  Asp Asp Ser
    1010                1015                1020

Leu Arg  Ile Gly Gly Gln Val  His Ala Val Gln Ala  Leu Val Gln
```

```
                 1025                1030                1035

Leu Phe Leu Glu Arg Glu Arg Ala Ala Gln Leu Ala Glu Ser Lys
    1040                1045                1050

Thr Asp Glu Leu Ile Lys Asp Ala Pro Thr Thr Gln His Asp Lys
    1055                1060                1065

Ser Gly Glu Trp Gln Glu Thr Ser Gly Glu Ile Gln Trp Val Ser
    1070                1075                1080

Thr Glu Lys Thr Asp Gly Thr Glu Glu Lys His Lys Lys Glu Glu
    1085                1090                1095

Glu Asp Glu Glu Leu Asp Leu Asn Lys Ala Leu Gln His Ala Gly
    1100                1105                1110

Lys His Met Glu Asp Cys Ile Val Ala Ser Tyr Thr Ala Leu Leu
    1115                1120                1125

Leu Gly Cys Leu Cys Gln Glu Ser Pro Ile Asn Val Thr Thr Val
    1130                1135                1140

Arg Glu Tyr Leu Pro Glu Gly Asp Phe Ser Ile Met Thr Glu Met
    1145                1150                1155

Leu Lys Lys Phe Leu Ser Phe Met Asn Leu Thr Cys Ala Val Gly
    1160                1165                1170

Thr Thr Gly Gln Lys Ser Ile Ser Arg Val Ile Glu Tyr Leu Glu
    1175                1180                1185

His Cys
    1190

<210> SEQ ID NO 2
<211> LENGTH: 3570
<212> TYPE: DNA
<213> ORGANISM: Homo sapiens

<400> SEQUENCE: 2 atgcatcca gatttgggaa acatacagt aggaaaggtg gaaatggcag ttcaaaattc      60
gatgaagtct tttccaacaa acggactacc cttagcacaa atggggaga gaccacattt    120 atggctaaat tagggcagaa gaggcccaat ttcaaaccag atatccaaga aattccgaag    180
aaacctaaag tggaagaaga aagtactgga gatccttttg gatttgatag tgatgatgag    240
tctctaccga tttcttcaaa gaatttagcc caggttaagt gttcctctta ttcagaatct    300
agtgaagctg ctcagttgga agaggtcact tcagtacttg aagctaatag caaaattagt    360
catgtggtcg ttgaagacac tgtcgtttct gataaatgct tcccctttgga ggacacttta    420 cttgggaaag aaaagagcac aaaccgaatt gtagaagatg atgcaagcat aagtagctgt    480
aataaattaa taacttcaga taagtggag aattttcatg aagaacatga aaagaatagt    540
caccatattc acaaaaatgc tgatgacagt actaagaaac ccaatgcaga aactacagtg    600
gcttctgaaa tcaaggaaac aaatgatact tggaactccc agtttgggaa aaggccagaa    660
tcaccatcag aaatatctcc aatcaaggga tctgttagaa ctggtttgtt tgaatgggat    720
aatgattttg aagatatcag atcagaagac tgtattttaa gtttggatag tgatcccctt    780
ttggagatga aggatgacga ttttaaaaat cgattggaaa atctgaatga agccattgag    840
gaagatattg tacaaagtgt tcttaggcca ccaactgta ggacgtactg tagggccaat    900
aaaacgaaat cctcccaagg agcatcaaat tttgataagc tgatggacgg caccagtcag    960
gccttagcca aagcaaacag tgaatcgagt aaagatggcc tgaatcaggc aaagaaaggg   1020
ggtgtaagtt gtgggaccag ttttagaggg acagttggac ggactagaga ttacactgtt   1080
```

```
ttacatccat cttgcttgtc agtttgtaat gttaccatac aggatactat ggaacgcagc   1140
atggatgagt tcactgcatc cactcctgca gatttgggag aagctggtcg tctcagaaaa   1200
aaggcagata ttgcaacttc taagactact actagatttc gacctagtaa tactaaatcc   1260
aaaaaggatg ttaaacttga attttttggt tttgaagatc atgagacagg aggtgatgaa   1320
ggaggttctg gaagttctaa ttacaaaatt aagtattttg ctttgatga tctcagtgaa     1380 agcgaagatg atgaagatga tgactgtcaa gtagaaagaa agacaagcaa aaaagaact     1440 aaaacagctc catcaccctc cttgcagcct cccccagaaa gcaatgataa ttcccaggac   1500
agtcagtctg gtactaacaa tgcagaaaac ttggatttta cagaggactt gcctggtgtg   1560
cctgaaagtg tgaagaagcc cataaataaa caaggagata atcaaagga aataccaga     1620 aagattttta gtggccccaa acggtcaccc acaaaagctg tatataatgc cagacattgg   1680
aatcatccag attcagaaga actgcctggg ccaccagtag taaaacctca gagtgtcaca   1740
gtgaggctgt cttcaaagga accaaatcaa aagatgatg gagtttttaa ggctcctgca    1800
ccaccatcca aagtgataaa aactgtgaca atacctactc agccctacca agatatagtt   1860
actgcactga aatgcagacg agaagacaaa gaattatata ctgttgttca gcacgtgaag   1920
cacttcaacg atgttgtaga atttggtgaa aatcaagagt tcactgatga cattgagtac   1980
ttgttaagtg gctaaagag cactcagcct ctaaacacac gttgcttag tgttattagc     2040 ttggctacta aatgtgccat gcccagtttt cgaatgcacc tgagagcaca tgggatggta   2100
gcaatggtct ttaaaacctt ggatgattcc cagcaccatc agaatctgtc cctctgtaca   2160
gctgccctca tgtatatact gagtagagat cgtttgaaca tggatcttga tagagctagc   2220
ttagatctaa tgattcgact tttgaactg gaacaagatg cttcatcagc caagctactg    2280
aatgaaaaag acatgaacaa aattaaagaa aaaatccgaa ggctctgtga aactgtacac   2340
aacaagcatc ttgatctaga aaatataacg actgggcatt tagctatgga gacattatta   2400
tcccttactt ctaaacgagc aggagactgg tttaaagaag aactccggct tttgggtggt   2460
ctggatcata ttgtagataa agtaaaagaa tgtgtggatc atttaagtag agatgaggat   2520
gaagagaaac tggtagcctc actatgggga gcagagagat gtttacgagt tttagaaagt   2580
gtaactgtgc ataatcccga aaatcaaagc tacttgatag catataaaga ttcccaactt   2640
attgtttcat cagctaaagc attacagcat tgtgaagaac tgattcagca gtacaaccgt   2700
gctgaggaca gcatatgctt agctgacagt aagcctctgc ctcaccagaa tgtaactaac   2760
catgtaggca aagcagtgga ggactgcatg agggccatca tcgggtgtt gcttaattta    2820 actaatgata atgagtgggg cagcaccaaa acaggagagc aggacggtct cataggcaca   2880
gcgctgaact gtgtgcttca ggttccaaag tacctacctc aggagcagag atttgatatt   2940
cgagtgctgg gcttaggtct gctgataaat ctagtggagt atagtgctcg gaatcggcac   3000
tgtcttgtca acatggaaac atcgtgctct tttgattctt ccatctgtag tggagaaggg   3060
gatgatagtt taaggatagg tggacaagtt catgctgtcc aggctttagt gcagctattc   3120
cttgagcgag agcgggcagc ccagctagca gaaagtaaaa cagatgagtt gatcaaagat   3180
gctcccacca ctcagcatga taagagtgga gagtggcaag aaacaagtgg agaaatacag   3240
tgggtgtcaa ctgaaaagac tgatggtaca aagagaaac ataagaagga ggaggaggat    3300
gaagaacttg acctcaataa agcccttcag catgccggca acacatgga ggattgcatt    3360 gtggcctcct acacggcact acttcttggg tgtctctgcc aggaaagtcc aatcaatgta   3420
accactgtgc gggaatatct gccagaagga gacttttcaa taatgacaga gatgctcaaa   3480
```

```
aaattttttga gttttatgaa tctcacttgt gctgttggaa caactggcca gaaatctatc   3540
tctagagtga ttgaatattt ggaacattgc                                     3570

<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
ttggatccat gacatccaga tttgggaaaa catacagtag g                         41

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
ttgaattcct agcaatgttc caaatattca atcactctag a                         41

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gaattcatag gcacagcgct gaactgtgtg                                      30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ttgaattcct agcaatgttc caaatattca                                      30

<210> SEQ ID NO 7
<211> LENGTH: 19
<212> TYPE: DNA
<213> ORGANISM: Artificial Sequence
<220> FEATURE:
<223> OTHER INFORMATION: short interfering nucleotide sequence

<400> SEQUENCE: 7
cggactaccc ttagcacaa                                                  19

<210> SEQ ID NO 8
<211> LENGTH: 41
<212> TYPE: DNA
<213> ORGANISM: Artificial Sequence
<220> FEATURE:
<223> OTHER INFORMATION: Primer

<400> SEQUENCE: 8
ttggatccat gacatccaga tttgggaaaa catacagtag g                         41

<210> SEQ ID NO 9
```

```
<211> LENGTH: 41
<212> TYPE: DNA
<213> ORGANISM: Artificial Sequence
<220> FEATURE:
<223> OTHER INFORMATION: Primer

<400> SEQUENCE: 9
ttgaattcct agcaatgttc caaatattca atcactctag a                              41

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gggaaatcgt gcgtgacatt aag                                                  23

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tgtgttggcg tacaggtctt tg                                                   22

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
aaaaagcagg ctccaccatg tttcaggacc cacaggagcg accc                           44

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
agaaagctgg gttacagctg ggtttctcta cgtg                                      34

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
aaaaagcagg ctccaccatg catggagata cacctacat                                 39

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
```

```
agaaagctgg gttatggttt ctgagaacag atgggg                              36

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
aaaaagcagg ctccaccatg gagacagcat gcgaac                              36

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
agaaagctgg gtcagaagtc caagctggct gtaaag                              36

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
ggggacaagt ttgtacaaaa aagcaggct                                      29

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
ggggacaagt ttgtacaaga aagctgggt                                      29

<210> SEQ ID NO 20
<211> LENGTH: 18
<212> TYPE: PRT
<213> ORGANISM: Homo sapiens

<400> SEQUENCE: 20

Cys Asn Phe Lys Pro Asp Ile Gln Glu Ile Pro Lys Lys Pro Lys Val
1               5                   10                  15

Glu Glu

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
gtgcatccca cccacagtgg aagacatgg                                      29

<210> SEQ ID NO 22
<211> LENGTH: 30
```

```
<212> TYPE: DNA
<213> ORGANISM: Artificial Sequence
<220> FEATURE:
<223> OTHER INFORMATION: Primer

<400> SEQUENCE: 22
ccgcttccgc cggtgaatgg tcagtgctgg                                    30

<210> SEQ ID NO 23
<211> LENGTH: 19
<212> TYPE: DNA
<213> ORGANISM: Artificial Sequence
<220> FEATURE:
<223> OTHER INFORMATION: Synthetic control oligonucleotide

<400> SEQUENCE: 23
actacaactg gtcgcaacc                                                19

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 24
aacggactac ccttagcaca acctgtctc                                     29

<210> SEQ ID NO 25
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 25
aattgtgcta agggtagtcc gcctgtctc                                     29

<210> SEQ ID NO 26
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 26
aaactacaac tggtcgcaac ccctgtctc                                     29

<210> SEQ ID NO 27
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 27
aaggttgcga ccagttgtag tcctgtctc                                     29

<210> SEQ ID NO 28
<211> LENGTH: 6307
<212> TYPE: DNA
<213> ORGANISM: Homo sapiens

<400> SEQUENCE: 28
gcgagcggct gttggaggaa ggaggtgggg gccgggagcg caaatggcgt tgagatggty    60
```

```
carggccctg ttcaaactcc agcactgacc attcaccggc ggaagcggcg gcgcaggagg    120
cggcggcggc ccagcggggg cacacagcag gctctgttac cagctccagc agtggcggcc    180
agcgagagct aggcccgsgc ccggccggcg gcgctcgagg cggggaggga agttgcgggg    240
ccgccgctcc tgccccccca accgggcttc ctatttaccg aaagcagagt ccctcgcctc    300
tctcggctct cacctgccgg ccctgctctc ccgcgcgagg gttccgcgcc cgcccgcggg    360
ccgtarggag cgggagaagg cggargcggc cccgtggcca agcacccgc caggcttccg     420 aggagaatat gaaactggtg tcaaaatgac atccagattt gggaaaacat acagtaggaa    480
aggtggaaat ggcagttcaa aattcgatga agtcttttcc aacaaacgga ctacccttag    540
cacaaaatgg ggagagacca catttatggc taaattaggg cagaagaggc ccaatttcaa    600
accagatatc caagaaattc cgaagaaacc taaagtggaa gaagaaagta ctggagatcc    660
ttttggattt gatagtgatg atgagtctct accagtttct tcaaagaatt tagcccaggt    720
taagtgttcc tcttattcag aatcagtgat agctgctcag ttggaagagg tcacttcagt    780
acttgaagct aatagcaaaa ttagtcatgt ggtcgttgaa gacactgtcg tttctgataa    840
atgcttccct ttggaggaca ctttacttgg gaaagaaaag agcacaaacc gaattgtaga    900
agatgatgca agcataagta gctgtaataa attaataact tcagataaag tggagaattt    960
tcatgaagaa catgaaaaga atagtcacca tattcacaaa aatgctgatg acagtactaa   1020
gaaacccaat gcagaaacta cagtggcttc tgaaatcaag gaaacaaatg atacttggaa   1080
ctcccagttt gggaaaaggc cagaatcacc atcagaaata tctccaatca gggatctgt    1140 tagaactggt ttgtttgaat gggataatga ttttgaagat atcagatcag aagactgtat   1200
tttaagtttg gatagtgatc ccttttggga gatgaaggat gacgatttta aaaatcgatt   1260
ggaaaatctg aatgaagcca ttgaggaaga tattgtacaa agtgttctta ggccaaccaa   1320
ctgtaggacg tactgtaggg ccaataaaac gaaatcctcc caaggagcat caaattttga   1380
taagctgatg gacggcacca gtcaggcctt agccaaagca acagtgaat cgagtaaaga    1440 tggcctgaat caggcaaaga aaggggtgt aagttgtggg accagttta gagggacagt     1500 tggacggact agagattaca ctgttttaca tccatcttgc ttgtcagttt gtaatgttac   1560
catacaggat actatggaac gcagcatgga tgagttcact gcatccactc ctgcagattt   1620
gggagaagct ggtcgtctca gaaaaaaggc agatattgca acttctaaga ctactactag   1680
atttcgacct agtaatacta aatccaaaaa ggatgttaaa cttgaatttt ttggttttga   1740
agatcatgag acaggaggtg atgaaggagg ttctggaagt tctaattaca aaattaagta   1800
ttttggcttt gatgatctca gtgaaagcga agatgatgaa gatgatgact gtcaagtaga   1860
aagaaagaca agcaaaaaaa gaactaaaac agctccatca ccctccttgc agcctccccc   1920
agaaagcaat gataattccc aggacagtca gtctggtact aacaatgcag aaaacttgga   1980
ttttacagag gacttgcctg tgtgcctga agtgtgaag aagcccataa ataaacaagg     2040
agataaatca aggaaaata ccagaaagat ttttagtggc cccaaacggt cacccacaaa    2100
agctgtatat aatgccagac attggaatca tccagattca gaagaactgc ctgggccacc   2160
agtagtaaaa cctcagagtg tcacagtgag gctgtcttca aaggaaccaa atcaaaaaga   2220
tgatggagtt tttaaggctc ctgcaccacc atccaaagtg ataaaaactg tgacaatacc   2280
tactcagccc taccaagata tagttactgc actgaaatgc agacgagaag acaaagaatt   2340
atatactgtt gttcagcacg tgaagcactt caacgatgtt gtagaatttg gtgaaaatca   2400
agagttcact gatgacattg agtacttgtt aagtggctta aagagcactc agcctctaaa   2460
```

```
cacacgttgc cttagtgtta ttagcttggc tactaaatgt gccatgccca gttttcgaat    2520
gcacctgaga gcacatggga tggtagcaat ggtcttaaa accttggatg attcccagca    2580
ccatcagaat ctgtccctct gtacagctgc cctcatgtat atactgagta gagatcgttt    2640
gaacatggat cttgatagag ctagcttaga tctaatgatt cgacttttgg aactggaaca    2700
agatgcttca tcagccaagc tactgaatga aaaagacatg aacaaaatta agaaaaaat     2760 ccgaaggctc tgtgaaactg tacacaacaa gcatcttgat ctagaaaata taacgactgg    2820
gcatttagct atggagacat tattatccct tacttctaaa cgagcaggag actggtttaa    2880
agaagaactc cggcttttgg gtggtctgga tcatattgta gataaagtaa agaatgtgt     2940 ggatcattta agtagagatg aggatgaaga gaaactggta gcctcactat ggggagcaga    3000
gagatgttta cgagttttag aaagtgtaac tgtgcataat cccgaaaatc aaagctactt    3060
gatagcatat aaagattccc aacttattgt ttcatcagct aaagcattac agcattgtga    3120
agaactgatt cagcagtaca accgtgctga ggacagcata tgcttagctg acagtaagcc    3180
tctgcctcac cagaatgtaa ctaaccatgt aggcaaagca gtggaggact gcatgagggc    3240
catcatcggg gtgttgctta atttaactaa tgataatgag tggggcagca ccaaaacagg    3300
agagcaggac ggtctcatag gcacagcgct gaactgtgtg cttcaggttc caaagtacct    3360
acctcaggag cagagatttg atattcgagt gctgggctta ggtctgctga taaatctagt    3420
ggagtatagt gctcggaatc ggcactgtct tgtcaacatg gaaacatcgt gctcttttga    3480
ttcttccatc tgtagtggag aagggggatga tagtttaagg ataggtggac aagttcatgc    3540
tgtccaggct ttagtgcagc tattccttga gcgagagcgg gcagcccagc tagcagaaag    3600
taaaacagat gagttgatca agatgctcc caccactcag catgataaga gtggagagtg    3660
gcaagaaaca agtggagaaa tacagtgggt gtcaactgaa aagactgatg gtacagaaga    3720
gaaacataag aaggaggagg aggatgaaga acttgacctc aataaagccc ttcagcatgc    3780
cggcaaacac atggaggatt gcattgtggc ctcctacacg gcactacttc ttgggtgtct    3840
ctgccaggaa agtccaatca atgtaaccac tgtgcgggaa tatctgccag aaggagactt    3900
ttcaataatg acagagatgc tcaaaaaatt tttgagtttt atgaatctca cttgtgctgt    3960
tggaacaact ggccagaaat ctatctctag agtgattgaa tatttggaac attgctagct    4020
gctttacctt tgcttcaggt gctcggtaat gctggagcta tccttagaca agaaaaagtc    4080
aagtcatgaa agaagtcctt gaagatatac caagaacatt catcagtatc attcgtgttt    4140 ggattttaa ggccacctga tttcttcgtc atgcattcgg catttgctaa atgacagtta     4200
ctacatcaat ctgcaactat caaaaatgag gggaaaaggt tcaggctgtt aacaattcca    4260
tgcagtattt aaatacattt actttggcag agtttatacc ctcccttgt tttcttgctt     4320 tattctgggc aagtttgaag gggaaaattt gtgctgctgt tagtgcaact gctgtgtatg    4380
ttgagccact gttgtcatgc cagccaggtg caaaggcagc ttagctactg aggtagcgaa    4440
tgttctgagg acattctaga caacagctta gttccttttt caggctcatt tgcttttgct    4500
tttttgttga atgattccaa tcgtaaataa agcttttaat aattttgtga attttttggt    4560
tgttgttccc tgaactactg tctatattta aaattagatg gaatccaaag atacacggga    4620
ttaatagtat atttttttat tcttgattag gtttgggtta ttgaactatt ttttactttt    4680
gagaccacaa ccatattcaa tatcatacca taatgtgtca tagctatagg cacaagaaaa    4740
acaacagttt gagagaatat tatataagat gatgtgccct gttaaaagga ggaggcaaaa    4800
```

```
tagtcaaacc cagggtagtt tacacttaat gctagggagg ctcttaaaac attattagat    4860
tttgaggaaa gactctctag atatattttc taatgttcag tacaataaat ataaggaagc    4920
taaaacacca atgtggaatt cctgtttcca gataacatgt atattcttct atagagtgac    4980
aggatcaatt gcataagcgc aaagccttaa attgctggtt tagagaagac ccttttttca    5040
ttcagattct ttgttcgtag agcagttatt tgaaaaacag ttatggaaca caaaacattt    5100
tatagattta atatcataac attgcaaatt tttcttgtat tattgttcac accactggtt    5160 atacttttt ttttccttt ttattgattg ggcctgaata caggctttct agagatcttt    5220
ttcattaata cttttaaata cctttcaggt agttacatca tgtttcttca ttggatttgt    5280
aaaacttgaa gccataaaaa tattagtttg gtgtgtattg gggaaaatag ctaaaagtct    5340 aattttacc catttagact ttgttattc cttgtataaa gtgacaaatc ggggctcttg    5400
tatcagtgcc agctgtaatg tttttaaatg cagtggctgc cttctattgt cttcctattt    5460
ttgataatgc agattgttgg gaaatctgta aggaagtaac tgattccagg caaattgttt    5520
tcttccttct acccacccca accctaccc atcaccttt aagaacatag tacgccagtg    5580
taacgtggga accattgaga ttgtatttgc cctgagtatt aaagctagct tagcaaaata    5640
cttttaaaaa catattggta aatgatacc ataaaattaa attagttata ttttatttta    5700
aaatgcaaaa tacattgata tttattaatc attggattta gggaaaggga cagattttg    5760 gtgaacctga cttgtggcag atggtaagga atattataaa acatttggat gagaacaatc    5820
agggcgaact gcatttttct gttacactgg taatcatttg aaaattgatt tacctcagtg    5880
tttaacagtt ttttgttttg ttttgttttt taaataataa ctaattgtcg agcactgata    5940
gagatgcaga ttttggtggg ggggggtggt gggggagata atcacttcac caactgcagt    6000
gcatttgtgt gttttaacc ctcagagaac tctgcatttt agggtacttg aggctgactt    6060
aactaaaagt tttaaagtaa ccttttttcc attgtaaata tttctgtaaa tactaccaat    6120
tggaaattag aacagtagag tacttttctg aatccaatcc tattttatt ttatacagta    6180 tttctcagct gtgatctttg gagcaaaagc caacggcagg aaaaaatagt ttgtaccagt    6240
ttcatgaagt atgtctttgg gttttgtaa ataatttaa ctcaaataaa attgctactt    6300
tcaatac                                                              6307
```

<210> SEQ ID NO 29
<211> LENGTH: 5662
<212> TYPE: DNA
<213> ORGANISM: Homo sapiens

<400> SEQUENCE: 29

```
atttttagta gagacggggt ttcaccgtgt tagccaggat ggtctcgatc tcctgacctc      60
atgatccgcc tgcctcggcc tctcaaagtg ctaggattac aggcgtgagc caccgtgcct     120
ggccgctgaa cacaatttaa agcttcaatt aatccaggta ttcagtcaac aaatatttat     180
agcacacttt ctgtgtgtga ggcactattc taggtgtgct tggcatataa aatgaacaaa     240
agtcagccat cctcgtcctc atggagttta tattcttgtg aaacgaaata gataataaac     300
aagttcatac acaaagcaaa cgtaatgact atgttatgga gaaagcagc agggaaaagg     360 agatacaggt tgctggatga cctaaatag catggccaag gaaaacatta ctgagagaca     420
cacttgagca aagacctgaa agcatgcagg gaatgagttg tgtgtgtctc ttgaggacta     480
acagagggaa caagtacgaa gagggcccac aggcaggagc tggcttggca tgttctagta     540
gtagacagag gcaggcccgg caaggtagga agggatagga gtactcaggg gccagatcat     600
```

```
gcagggcctt ttcaccgtta agaactttgg attttagtat tacaggagga cccttcaggg    660
tgtttgacta ggcgggtatc atacagtatt aagggtgagg atcctgaata aaaaagggct    720
gtttccagga caagggtcag gaagccagac ttcttcgagg ttgcttgtac cggtccttgt    780
caggcaatgt gctcctagag aatttccttt gctttgtgtt tcatctacct agacagcagt    840
gtattcccca gaggacgtca ctatctccag agaacatatt ccaattatcc tgggaaatat    900
gataattggg attataacag tactcatttt ctcaattctc agaatgaaaa cctatccaag    960
gcaagaacaa aagttctcca gaaagcactc ccctcccaat tgtgaaaacc cagttaacat   1020
tttattagag ctaccaggtt atgtgaaact gttgatagtt ttatcacttt cctttcaaga   1080
tataggcagg ggcagtggct catgcctgta attccagcac tttgggaggc caaggtaggt   1140
ggatggcttg agcccagaag ttcaagacca gcctgggcaa caaggtgaaa ccctatctct   1200
accaaaaata caaaaattag tggggcatga tagcatggac atgtagtccc agctacttgg   1260
gaggctgagg tgggaggatg gcttgaaccc tggaggtgga ggttgcagtg attggagatc   1320
gtgccactac attccagcct gggcgacaga gcaagactct gtcaccaaaa aaaaaaaaaa   1380
aaaaaaaaaa aaaaatgtg ccaggcatg gtagctcaca cctgtaatcc cagcactttg   1440
ggaggctgag ccaggcggat cacaaggtca agagatcgaa accatcctgg ccaacatgca   1500
aaacaccatc tctactaaaa tacaaaaaat gagctgggtg tggtggtgtg cgcctgtagt   1560
cccagctact ggggaggctg aggcagggga atcgcttgaa ccaggaggc agagattgca   1620 gtgagccgag atcgcgccac tgcactccag cctggtgaca gagcgagact ccgtctaaaa   1680
aaaaaaaaaa aaaatatat atatatatat ataaatata tgtatataat tttacatgaa   1740
agaaggaaat aaatgggtgc ttttattcaa caaatattta ttgagcacct actcttgtgc   1800
caggcagtct tctaggtgct agggttgcag cagaaaacaa gacaggcaga gatccctgcc   1860
ttcagaggga gcacaacatt taagataaac atgcaaaatg cctgatatgt tagatgggaa   1920
gataaatgcc cttaaagaaa gtaaagcagg gacagtgaca tttaggagtg aggatgttgc   1980
aacaatttaa gataggttgg tcaggggaga ttcattgaaa agtcccatct gagtgaaaac   2040
ctagaggaga gaattgaagc aggctggtat ctggggagt tgtaggcaga gggaatagga   2100
aatacaaagg ccctaaggtg gggaaacagc aaggagtcag gtgtgggcag agcagaaagt   2160
tggggctgca tgagcaaagg gcagggcctg gcccacatct cgtagagctt tgtaatataa   2220
ccacaacatg caagtgtaca atttaacatt ttattccaca tccgatggca agaaaaatt   2280 gactgctacc aatatggtag tttctgacct gtagttccct aaatagaatt ctataagttg   2340
taatacactt tactacacat tatcagaaaa agactaaaag ttctatttag taactccaat   2400
tctgacagtt ctcatgtctg ggctagaaca agggcatggc aatggcagaa cagatgtctt   2460
ctattttctt tgcaggattt ctttttttca gaggaaagta caggtatggg cccactcaag   2520
tggagctcca ggttagggg ttctgtcctc acccaggcag cacacaggag ggcagaggcc   2580
cctcctaagg gtactacaaa cttggctctg atccatgatt tcagtttctg acaaacacaa   2640
cattcagtgg gggaaagaaa atcaggtatc tgagagcttg cacacaggca ttctagcaaa   2700
accaaaagca cctactggct acttgatgtt agtgtgaaga ttctcatgaa atggagacaa   2760
ccattctagg ggttgaggtg gccaggggga tggagcctga gctgagagaa ctaagaaaac   2820
aaaaacaata caacaaaaag ctgttcagcc atgtgttacc cacactggag ttctgtttgc   2880
tcattctggt gtggaaccca gggccctggt aagggaatga ggggacttca gggcatttgc   2940
```

```
ttgcctcagt ggaagcaggg aggtaagggg ttaaggtggt ggtacagcct gcagggccag    3000
gagtctgaac tccctccagg aggggcccga ggggtgtctt tagtgtgagc cacacaaggg    3060
tacagagccc agaagagctc tgcttaatat tcatatacta agcttccaca gactaaatac    3120
acacacacac acacacacac acacacactc acacacactt tacttctcaa atcatgtacc    3180
actttctacc agattcaaga acaccaagaa gtactaaagg gtatccaacc gtcaagaaaa    3240
agtttgactc cctcattagt tgtaacatac aagtcttccc atttccttac ttgtaagata    3300
gagtaatgga ctgggaagca gacaaggccc ctgaacagcc tagcatctta cctgatgcat    3360
aggaggttct taatcatctc ccttcctctc cctcatccta acgaaaaata ctagattgct    3420
gtcaaatgct atgggtatac tttaaatcag tgcttgtcaa actttaatgt gcagcccaat    3480
cagctggggg aatcctgtta aaatgcaggt tctgattcag tggagctggg gtgagggata    3540
ggaattatgc gttccttaca ggcttccagg tgatgctaca ctgctgattg gggatcattc    3600
tttgagtggc aagaatttga cactactaag tttcattact taacacaacc atcacataaa    3660
agccctcaaa aggcaccagt ctaaacaata agcccttcca cttcagcctc atgcaggcac    3720
tgaccctgcc aagtgtccag cactagagag gccaggcata atagacatat cctttggtct    3780
tgggaggatc acgacaccct cctacaggaa gatcttgcaa ttgtttcctc acctcttctg    3840
gttttttgat cttaccttt gcctctgatg ataattaccc tttaattacc acccaccacc    3900
ttgtcatcta ataattata gtaagtgcag cctgcacctc tgccagaaga tctttaaaca    3960
aaatgataaa aacaagttcc taaactgcca attaaaaaaa gagacaaaac tgacccaaat    4020
aaaacagtca tgtgcatccc acccacagtg gaagacatgg acttgttttt catataaact    4080
acagaagaag ttgatttatt ttgaaacaag aaaaagtact gattcagtat ttaggaaatt    4140
gtaaatgtca gaatataaat tctgcagtca ggtaggcaaa acaatccaac cacactaaaa    4200
tccaccttaa attcctcttg ggaagagctg cagggtctct gaactatttt tcctttattt    4260
ggagtttccc cgattatacc ggagggagct ggataacttc tgggtgcatt aaaagcaaat    4320
tatccatttg tgggagaagg gcgggcttct cactgaaagc aattagtagt tttctaattt    4380
cccaggtggg tctccattaa ccgcctaaca aacaccaagg ctgtcggagt ccgacgaatc    4440
atgcacctct cttaggggga actggttgcg ctactcttta gaacgctgtt ttcccatggt    4500
agccttaaaa aaaacttacc aattttctga attaggtaac acattgaatg ggaaaaacct    4560
aagatagcac aaaaaggcgt acagcgaaaa attaagactc cttcctcccg tcatccgcca    4620
cctcactgtc ctccctagag gcaatcgctg gttcacttct ttaaactttt tattatggaa    4680
aatttcagat acacaagtaa agagactgta tgatgagcac atatgctcgc atcacgcagc    4740
ttcaacgatg aaaaacgttc tgccagcttg ttttattcct ctcccccagt tttcataggc    4800
gtattttaca gtcctgacac cagatcactc tgtcaacaca tcagtaggtc ttaaaaaaaa    4860
aaaaacaaaa aaccataacc acattaccgt taccacaccc aacaaagtta atgataattg    4920
ctcaatacca tccaatattc tcggggccac tttcaatcgg tgaggggcag acggacttag    4980
aggaaggact gcagggctgg aggggcgcga aaaagcgagg ggcgacgctg ctcgtggcct    5040
cgggtgtccg gcgcctcgcg gtccccgcca tcgtcaccta cgccgggcca ggaccgacca    5100
ggccaggtcg agggcggctc ttgaccacgc gccccctgcc tccagctccc gggcggcgg    5160 cctccgcagg cccggcacag ctgcacagcc cgcggtcccc aggcaccggc gggtccctgg    5220
aggggaagcg attgatacag ctgcctgcac tgcgccaccc gcccggctgc ccatctccgt    5280
ggcacctgcg tctcccggct gggccgggag ctagaagtgg ctgccgagac cgggagggcc    5340
```

```
cggccagtcg cccgctcccg ctcccgcgcc tggccctcgg cccgcgacct cgcggacctg    5400
gactacaact cccgtggggc tccgacggcc gggccaatgg cgggcgcccg gagcatgcgg    5460
ggcgcagcgc ctgcgcggcg gtttgagtaa gcggctgcgc gattggctgc ggggtcgggc    5520
ggccgcgcgg ggactgtggg aagcggagtg acggagcgag cggctgttgg aggaaggagg    5580
tgggggccgg gagcgcaaat ggcgttgaga tggttcaggg ccctgttcaa actccagcac    5640
tgaccattca ccggcggaag cg                                             5662

<210> SEQ ID NO 30
<211> LENGTH: 4105
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t

<400> SEQUENCE: 30
ncggccgcca gggaggccta ggccctgtcc ggccggcgcg cctgaggtgg ggagggaagt      60
tgcggggccg ccgctcaccc cccaccccccc ctgtcgcccg agcttcctat ttaccgaagc    120
ggagccgcgg actgtgacgg cagcagagcc cctcgcccct ctcggtggca ccggtcggca    180
ctggtctctc gcgcggggct cccgcgcccg cccgcgggcc gttgggagcc ggagaggcgg    240
aggcggcccg aggccaaagc acccgccagg cgccgagggg aatatgaaac aggtgtcaaa    300
atgacatcca gatttggaaa aacttacagt aggaaaggag gaaatggcag ttcaaaattt    360
gatgaagttt tttccaacaa acggactact cttagtacaa atggggtga gaccacattt    420 atggctaaat tagggcagaa gaggcccaat ttcaaaccag atattcaaga aattccgaag    480
aaacctaaag tagaagaaga agatactgga gatccctttg gttttgatag tgatgatgag    540
tctctacctg tttcttcaaa aaatttagcc cagggtaagg gttcatctta ctcagaatct    600
agtgaggctg ctcagctgga agaagtcact tctgtatttg aagctaatag caaatgtagt    660
catgtggtgg gtgaagacag ttttgcttcc gacagatgct tacttgtgga ggatacttta    720
attgggaaag agaagagcat aagtagaatt ccagaagaca acgcaaacaa agtagttgc    780 actaagttgc taacttcaga taaagtggag aattttagtg aagaacatga aaaaaatagt    840
caccactttc acaaaaatgc tgaagatagt actaagaaac ccaatgcaga aaccgcagtg    900
gcttctgaat ataaagctga tgaaactaaa gaaacaaatg atacttggaa ctcccagtct    960
ggaaaaagaa cagagtctcc atctgaaagt tgtccagtca aaggatctgt aagaactggt   1020
ttatatgaat gggataatga ttttgaagat atcaggtcag aagactgtat ttaagtttg    1080 gataatgagt ctcttttgga gatgaaagac gaggatttaa aaaatcggat tggaggattg   1140
gaaaatctaa atgaaacctt tgaagaagat atcatacaaa gtgttcttag gccaagcaac   1200
tgtaggacgt actgtagggc caataaagcg agatcctcac agggagcatc aaattttgat   1260
aagctaatgg atggcaccag tcagtcctta gccaaagcaa acagtgaatc aagtaaagat   1320
ggcctgaatc aggcaaagaa aggtagtgca agttgtggga ccagttttcg aggaacagtt   1380
ggacggacta gagattacac tgttttacat ccatcttgct tgtcagtgtg taatgttacc   1440
atccaggata ctatggaacg gagtatggat gagttcaccg catccactcc tgcagattta   1500
ggagaggctg gccggctcag aaaaaaggca gatattgcaa cctccaagac cactactaga   1560
tttcgaccta gtaatactaa atccaaaaag gatgttaaac ttgaattttt tggttttgaa   1620
```

```
gatcatgatg agacaggagg tgatgaaggg ggttctggaa gttctaatta caaaattaaa   1680
tattttggct ttgacgatct cagcgaaagt gaagatgatg atgatgacga ctgtcaagtg   1740
gaaagaaaga aagacaaaaa aagaactaaa acagctccat caccttccca gcagcctcct   1800
cctgaaagca gcgacaattc ccaggatagt cagtctagta ctaataatgc agaaaacttg   1860
gattttacag aggacttgcc tggtgtgcct gagagtgtga agaagcccat aagtaaacaa   1920
ggagataaat ccaaggaaaa taccagaaag atttttagtg gccccaaacg gtcacctaca   1980
aaagctgtat ataatgccag gcattggaac catccagact cggaagaatt gcctggacca   2040
ccaatagcaa aacctcagcg tgtcacagtg aggctgtctt caaaggaacc aaatcaaaaa   2100
gatgatggag tttttaaggc tcctgcacca ccactcaaag tgataaaaac tgtgacaata   2160
cctactcagc cctaccaaga aatagttact gcactgaaat gcagaaaaga agacaaagaa   2220
ttatatacgg ttgttcagca cgtgaaacac ttcaatgatg tggtggaatt tggtgaaaat   2280
caagagttca ctgatgacat tgaatacttg ttaagtggct aaagagtac tcagcctcta   2340 aacacacgtt gccttagtgt tatcagctta gctactaaat gtgccatgcc cagttttcgg   2400
atgcatctga gggcacatgg gatggttgca atggtcttta aaactctgga tgattcccag   2460
catcatcaga atctgtccct ctgtacagct gctctcatgt acatattgag tagagaccgt   2520
ttgaacatgg atcttgatag ggccagccta gatctcatga ttcggcttgt ggagttggaa   2580
caagatgcct cttcagctaa gctactgaat gaaaaagaca tgaacaagat caagaaaag   2640 atccgaagac tctgtgaaac tgtgcacaac aagcatcttg atctagaaaa cataacgact   2700
ggtcatttag ctatggagac attgctgtcc ctcacttcca aacgagcagg agattggttt   2760
aaagaagagc tccgacttct gggtggtctg atcatattg tagataaagt aaaagagtgt   2820
gtggatcatt aagtagaga tgatgaggac gaagagaaac tagtagcctc attatgggga   2880
gcagagagat gtttacgagt tttagagagt gtaacagtgc ataatccaga gaatcaaagc   2940
tacttgatag cctataaaga ttcacaactc attatttcat cagctaaagc attacagcat   3000
tgtgaagacc tgaatcagca gtacaaccgt gctgagaaca gcatctgtgt agcagacagt   3060
aaccctctgc cttaccagaa tgtaactaac catgtgggca aagcagtgga ggactgcatg   3120
agggctataa ttggagtatt gctcaattta actaatgata atgagtgggg cagcacaaag   3180
acaggagaac aagaaggact cataggcaca gcgatgaact gtgttcttca ggttccaaag   3240
tacctacctc aggagcagag atttgatatt cgagtgctgg gattgggtct actcataaac   3300
ctggtggagt atagtgcccg gaatcgacac tgccttgtca acatgcaaac atcctgttcc   3360
tttgattcct ccttctctag tggagaaggc gatcatagtt taaggctagc cggacaagtt   3420
catgctgttc aagctttagt gcagctattt ctcgaacgag agagcagc acaattggca   3480 gaaagtaaaa cagatgaatt gattaaagat gctcctacca ctcagcatga taagagtgga   3540
gagtggcaag aaacaagtgg agaaatacag tgggtatcaa ctgaaagac tgatggtgca   3600 gaggagaagc agaagaagga ggaggaggat gaagaacttg acctcaataa agcccttcag   3660
catgctggca aacacatgga ggattgcatc gtagcctcct acacagccct gcttcttggg   3720
tgtctctgcc aggaaagtcc aatcaatgta actacagtaa gggaatatct tccagaagga   3780
gatttctcca taatgacaga gatgcttaaa aagttcttaa gcttcatgaa tcttacgtgt   3840
gctgttggaa caacaggcca gaagtctatc tctagagtga ttgaatattt ggaacattgc   3900
tagctgcttt acctttgctt caggtgcttg gtaatgctga agctatcctt agacaaagaa   3960
aattggattt ttatgatcac ccgatttctt catcatgcat tctgcgtttg ctaaatgaca   4020
```

```
gttactacat caatctgcag ctatcaaaaa tgagggaaaa ggttcaggct gttaacaatc    4080
ccatgcagta tttaaataca cttac                                         4105

<210> SEQ ID NO 31
<211> LENGTH: 19
<212> TYPE: RNA
<213> ORGANISM: Artificial Sequence
<220> FEATURE:
<223> OTHER INFORMATION: short interfering nucleotide sequence

<400> SEQUENCE: 31
cggacuaccc uuagcacaa                                                  19
```